United States Patent [19]

Ohshima et al.

[11] Patent Number: 5,478,840
[45] Date of Patent: Dec. 26, 1995

[54] TRICYCLIC COMPOUNDS

[75] Inventors: Etsuo Ohshima; Fumihiko Kanai; Hideyuki Sato; Hiroyuki Obase; Toshiaki Kumazawa, all of Shizuoka; Shiho Takahara, Kanagawa; Tetsuji Ohno, Shizuoka; Tomoko Ishikawa, Shizuoka; Koji Yamada, Shizuoka, all of Japan

[73] Assignee: Kyowa Hakko Kogyo Co., Ltd., Tokyo, Japan

[21] Appl. No.: 294,978

[22] Filed: Aug. 24, 1994

Related U.S. Application Data

[60] Division of Ser. No. 65,916, May 25, 1993, Pat. No. 5,378,701, which is a continuation-in-part of Ser. No. 996,694, Dec. 24, 1992, abandoned.

[30] Foreign Application Priority Data

Dec. 27, 1991 [JP] Japan ................. 3-347294

[51] Int. Cl.⁶ ............... A61K 31/44; C07D 471/04
[52] U.S. Cl. ............................ 514/303; 546/118
[58] Field of Search ................... 514/303; 546/118

[56] References Cited

U.S. PATENT DOCUMENTS 4,122,186  10/1978  Lafon ............................. 424/315
5,128,356  7/1992  Naka et al. ..................... 514/381

FOREIGN PATENT DOCUMENTS 0400974  12/1990  European Pat. Off. .
0443983  8/1991  European Pat. Off. .

OTHER PUBLICATIONS

Da Re P, Valenti P, Primofiore G, Scarselli L, Cima L. Chiar. Ther. (1973), 8(1) 53–6.
Journal Medical Chemistry, vol. 34 (1991) 2919–22.

*Primary Examiner*—C. Warren Ivy
*Assistant Examiner*—Evelyn Huang
*Attorney, Agent, or Firm*—Fitzpatrick, Cella, Harper & Scinto

[57] ABSTRACT

A tricyclic compound represented by the following formula (I):

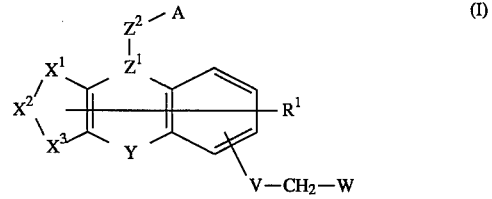

wherein $R^1$ represents hydrogen, halogen or lower alkyl; A represents cyano, carboxyl, tetrazolyl, cyano-substituted phenyl, carboxyl-substituted phenyl or tetrazolyl-substituted phenyl; V represents $—(CH_2)_m—$ (wherein m is an integer of 0 to 2); W represents

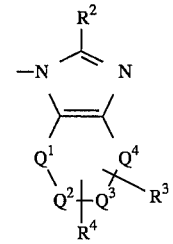

(wherein $R^2$, $R^3$ and $R^4$ independently represent hydrogen, halogen, lower alkyl, cycloalkyl, halogenated lower alkyl, hydroxy, lower alkoxy, amino, lower alkylamino, carboxyl or lower alkoxycarbonyl; and $Q^1—Q^2—Q^3—Q^4$ represents $N=CH—CH=CH$; $X^1—X^2—X^3$ represents $CH=CH—CH=CH$, $S—CH=CH$ or $CH=CH—S$; Y represents a single bond, $CH_2$, O, S, $CH_2O$, $OCH_2$, $CH_2S$, $SCH_2$, $CH_2CH_2$ or $CH=CH$; and $Z^1—Z^2$ represents $C=CH$, $CH—CH_2$ or $CH—CH(COOH)—$ or a pharmaceutically acceptable salt thereof. The compound of the present invention exhibits antagonism to angiotensin II receptors.

12 Claims, No Drawings

TRICYCLIC COMPOUNDS

This application is a division of application Ser. No. 08/065,916 filed May 25, 1993 now U.S. Pat. No. 5,378,701, which is a continuation-in-part of prior application Ser. No. 07/996,694 filed on Dec. 24, 1992 now abandoned.

BACKGROUND OF THE INVENTION

The present invention relates to tricyclic compounds exhibiting antagonism against angiotensin II (hereinafter referred to as AII) receptors and which are useful for the treatment of hypertension, congestive heart failure, renal failure and glaucoma.

Various peptide analogs are known as competitive inhibitors against AII receptors which are hypertensive peptide hormones. Further, as non-peptide inhibitors, there are known compounds wherein a fused heteroring such as benzimidazole and a biphenylmethane derivative are bonded [J. Med. Chem., 34, 2919 (1991); and U.S. Pat. No. 5,128, 356] and compounds wherein an amino acid derivative and a biphenylmethane derivative are bonded (EP-A-443983). However, no compound in which a fused heteroring or an amino acid derivative is bonded to a tricyclic compound related to the present invention in place of a biphenylmethane derivative is known.

A need exists for novel and useful AII receptor antagonists, which are expected to exhibit a preventive or therapeutic effect against a wide variety of diseases. An object of the present invention is to provide novel tricyclic compounds which inhibit the physiological activities of AII by means of their AII receptor antagonistic action.

SUMMARY OF THE INVENTION

The present invention relates to tricyclic compounds represented by the following formula (I)

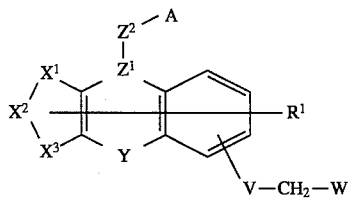

wherein $R^1$ represents hydrogen, halogen or lower alkyl; A represents cyano, carboxyl, tetrazolyl, cyano-substituted phenyl, carboxyl-substituted phenyl or tetrazolyl-substituted phenyl; V represents —$(CH_2)_m$— (wherein m is an integer of 0 to 2); W represents

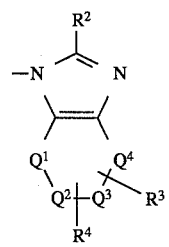

(wherein $R^2$, $R^3$ and $R^4$ independently represent hydrogen, halogen, lower alkyl, cycloalkyl, halogenated lower alkyl, hydroxy, lower alkoxy, amino, lower alkylamino, carboxyl or lower alkoxycarbonyl; and $Q^1$—$Q^2$—$Q^3$—$Q^4$ represents N=CH—CH=CH, CH=CH—CH=CH or $CH_2$—$CH_2$—$CH_2$—$CH_2$),

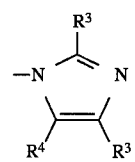

(wherein $R^2$, $R^3$ and $R^4$ have the same meanings as defined above),

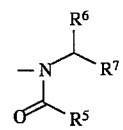

(wherein $R^5$ and $R^6$ independently represent hydrogen, lower alkyl or cycloalkyl; and $R^7$ represents carboxyl, lower alkoxycarbonyl, carbamoyl or hydroxymethyl) or

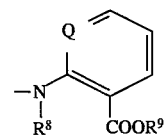

(wherein $R^8$ and $R^9$ independently represent hydrogen or lower alkyl; and Q represents N or CH); $X^1$—$X^2$—$X^3$ represents CH=CH—CH=CH, S—CH=CH or CH=CH—S; Y represents a single bond, $CH_2$, O, S, $CH_2O$, $OCH_2$, $CH_2S$, $SCH_2$, $CH_2CH_2$ or CH=CH; and $Z^1$—$Z^2$ represents C=CH, CH—$CH_2$, CH—CH(COOH)— or N—$(CH_2)_n$—(wherein n is an integer of 1 to 3) [hereinafter referred to as Compounds (I); the same applies to the compounds of other formula numbers] and pharmaceutically acceptable salts thereof.

DETAILED DESCRIPTION OF THE INVENTION

In the definitions of the groups in formula (I), the lower alkyl and the alkyl moiety in the halogenated lower alkyl, the lower alkoxy, the lower alkylamino and the lower alkoxycarbonyl mean a straight-chain or branched alkyl group having 1 to 6 carbon atoms such as methyl, ethyl, propyl, isopropyl, butyl, isobutyl, sec-butyl, tert-butyl, pentyl and hexyl, and the cycloalkyl means a cycloalkyl group having 3 to 6 carbon atoms such as cyclopropyl, cyclobutyl, cyclopentyl and cyclohexyl. The halogen includes, for example, fluorine, chlorine, bromine and iodine atoms.

The pharmaceutically acceptable salts of Compounds (I) include pharmaceutically acceptable acid addition salts, metal salts, ammonium salts, and organic amine addition salts.

Examples of the pharmaceutically acceptable acid addition salts of Compounds (I) are inorganic acid addition salts such as hydrochloride, sulfate, nitrate and phosphate, and organic acid addition salts such as acetate, maleate, fumarate and citrate; examples of the pharmaceutically acceptable metal salts are alkali metal salts such as sodium salt and potassium salt, alkaline earth metal salts such as magnesium salt and calcium salt, aluminum salt, and zinc salt; examples of the ammonium salts are ammonium salt and tetramethylammonium salt; and examples of the pharmaceutically acceptable organic amine addition salts are salts with morpholine and piperidine.

The processes for producing Compounds (I) are described below.

Process 1

Compound (I-1) [Compound (I) wherein $Z^1$—$Z^2$ is C=CH]

1-a: Process for preparing Compound (I-1a) which is Compound (I-1) wherein A is carboxyl and Compound (I-1d) which is Compound (I-1) wherein A is cyano Compound (I-1a) and Compound (I-1d) can be prepared by the following reaction steps.

Examples of the base applicable are sodium hydroxide, potassium hydroxide, sodium methoxide, potassium ethoxide, sodium hydride, potassium hydride, butyl lithium, lithium diisopropylamide (LDA), potassium tert-butoxide, triethylamine, diisopropylethylamine, tributylamine, dicyclohexylmethylamine, N—methylmorpholine, N-methylpiperidine, diazabicycloundecene (DBU) and diazabicyclononene (DBN).

Examples of the inert solvent are tetrahydrofuran (THF), dimethylformamide (DMF) and dimethylsulfoxide (DMSO).

(Step 2)

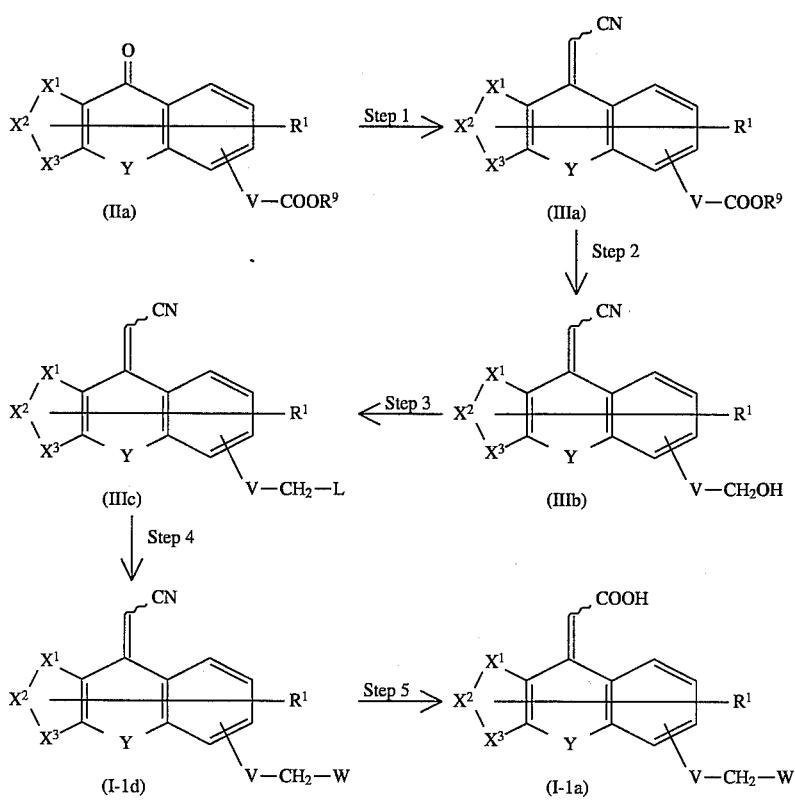

(In the formulae, L represents chlorine, bromine, methanesulfonyloxy or p-toluenesulfonyloxy; and $R^1$, $R^9$, $X^1$—$X^2$—$X^3$, Y, V and W have the same meanings as defined above.)

The starting Compound (IIa) can be obtained by known methods [J. Med. Chem., 19, 941(1976); ibid., 20, 66(1977); ibid., 20, 1499(1977); ibid., 21, 633(1978); ibid., 21, 1035(1978); ibid., 22, 1357(1979); ibid., 27, 372(1984); ibid., 29, 2347(1986); ibid; 35, 2074(1992); and Japanese Published Unexamined Patent Application No. 21679/83] or a method similar thereto.

(Step 1)

Compound (IIIa) can be obtained by reacting Compound (IIa) with 2 to 10 equivalents of a phosphorous acid diester [e.g. diethyl (cyanomethyl) phosphonate, and dimethyl (cyanomethyl)phosphonate] or an organosilicon compound (e.g. trimethylsilylacetonitrile) in the presence of 2 to 20 equivalents of a base in an inert solvent at a temperature of 0° C. to the boiling point of the solvent used for 0.1 to 48 hours.

Compound (IIIb) can be obtained by treating Compound (IIIa) with 1 to 50 equivalents of a suitable reducing agent such as lithium aluminum hydride, lithium borohydride, sodium borohydride or diborane in an inert solvent such as THF, in the presence of iodine, boron trifluoride ether complex, or the like if necessary, at a temperature of –100° C. to the boiling point of the solvent used for 0.1 to 48 hours.

(Step 3)

Compound (IIIca) which is Compound (IIIc) wherein L is chlorine or bromine can be obtained by reacting Compound (IIIb) with carbon tetrachloride or carbon tetrabromide in the presence of triphenylphosphine, and if necessary in the presence of 2,6-lutidine or 2,6-collidine, or with an equivalent to a large excess of a halogenating agent (e.g. thionyl chloride and phosphorus tribromide), in an inert solvent (e.g. dichloromethane and dichloroethane) at a temperature of –50° C. to the boiling point of the solvent used for 0.1 to 48 hours. Alternatively, Compound (IIIca) may be prepared by reacting Compound (IIIb) with methanesulfonyl chloride in the presence of collidine and lithium chloride in DMF at a temperature of −50° C to the boiling point of the solvent used for 0.1 to 48 hours.

Compound (IIIcb) which is Compound (IIIc) wherein L is methanesulfonyloxy or p-toluenesulfonyloxy can be obtained by reacting Compound (IIIb) with a sulfonylating agent (e.g. methanesulfonyl chloride and p-toluenesulfonyl chloride) in an inert solvent (e.g. dichloromethane and dichloroethane), in the presence of 2,6-lutidine or 2,6-collidine if necessary, at a temperature of −50° C. to the boiling point of the solvent used for 0.1 to 48 hours.
(Step 4)

treating Compound (I-1d) with an aqueous solution of sulfuric acid, hydrochloric acid, acetic acid, or the like, or a mixture comprising such acids, which also serve as a solvent, at a temperature of room temperature to the boiling point of the solvent used for one hour to three days, so that the nitrile group is hydrolyzed.

Alternatively, Compound (I-1a) can be prepared by the following reaction steps.

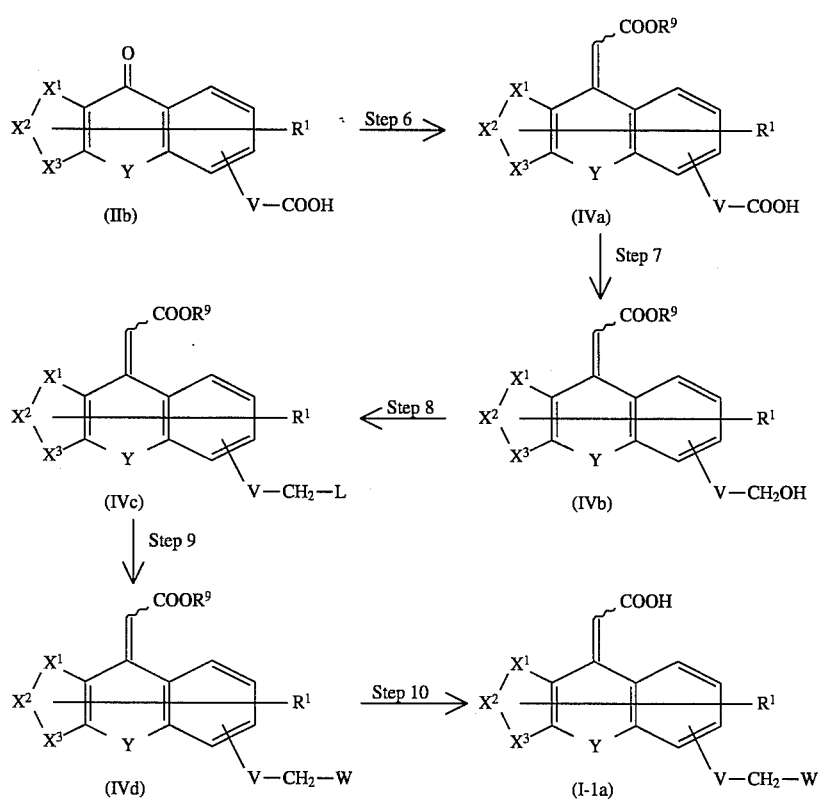

(In the formulae, $R^1$, $R^9$, $X^1$—$X^2$—$X^3$, Y, V, W and L have the same meanings as defined above.)

The starting compound (IIb) can be obtained according to the method for preparing Compound (IIa) described above.
(Step 6)

Compound (IVa) can be obtained from Compound (IIb) according to the method of Step 1 using ethyl diethylphosphonoacetate or methyl dimethylphosphonoacetate as the phosphorous acid diester or ethyl trimethylsilylacetate as the organosilicon compound.
(Step 7)

Compound (IVb) can be obtained from Compound (IVa) according to the method of Step 2.
(Step 8)

Compound (IVc) can be obtained from Compound (IVb) according to the method of Step 3.
(Step 9)

Compound (IVd) can be obtained from Compound (IVc) according to the method of Step 4.

Compound (I-1d) can be obtained by reacting Compound (IIIc) with an equivalent to a large excess of a compound represented by the formula H—W wherein W has the same meaning as defined above, in the presence of a suitable base [e.g. sodium hydride, potassium hydride, butyl lithium, LDA, potassium tert-butoxide, lithium bis(trimethylsilyl)amide, sodium bis(trimethylsilyl)amide and Proton Sponge (registered trademark)] if necessary, in an inert solvent [e.g. dichloromethane, DMF, THF, benzene, toluene, hexamethylphosphoric triamide (HMPA) and dimethylpropyleneurea] at a temperature of 0° C. to the boiling point of the solvent used for 0.1 to 48 hours.

The compound represented by the formula H—W can be obtained by known methods (Japanese Published Unexamined Patent Application No. 9518/91; and WO 92/04343) or a method similar thereto.
(Step 5)

Compound (I-1a) can be obtained by treating Compound (I-1d) with a base (e.g. lithium hydroxide, sodium hydroxide and potassium hydroxide) in a suitable aqueous solvent (e.g. ethyleneglycol, diethyleneglycol, glyme, dioxane and ethanol) at a temperature of room temperature to the boiling point of the solvent used for one hour to three days or by (Step 10)

Compound (I-1a) can be obtained by hydrolysis of Compound (IVd) in the presence of a suitable base (e.g. lithium hydroxide, sodium hydroxide and potassium hydroxide) in a suitable aqueous solvent (e.g. methanol, ethanol, THF and dioxane) at a temperature of room temperature to the boiling point of the solvent used for 0.1 to 48 hours.

Compound (I-1aa) which is Compound (I-1a) wherein m in V is 0 may also be prepared by the following reaction steps.

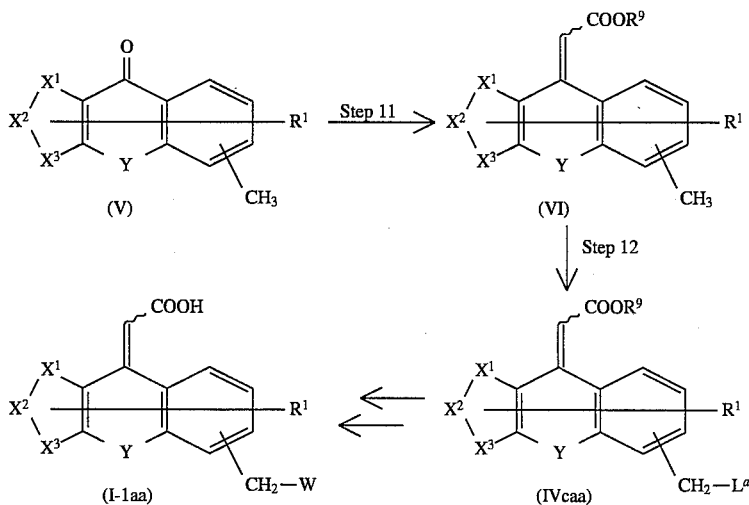

(In the formulae, $L^a$ represents chlorine or bromine; and $R^1$, $R^9$, $X^1$—$X^2$—$X^3$, Y and W have the same meanings as defined above.)

The starting compound (V) can be obtained by a known method [Helv. Chim. Acta, 73, 1197(1990)] or a method similar thereto.

(Step 11)

Compound (VI) can be obtained from Compound (V) according to the method of Step 6.

(Step 12)

Compound (IVcaa) can be obtained by heating Compound (VI) under reflux with 1 to 5 equivalents of N-chlorosuccinimide (NCS) or N-bromosuccinimide (NBS), in the presence of a radical initiator such as benzoyl peroxide or azobisisobutyronitrile (AIBN) if necessary, in an inert solvent such as carbon tetrachloride for 0.1 to 48 hours.

Subsequently, Compound (I-1aa) can be obtained according to the methods of the above Steps 9 and 10.

1-b: Process for preparing Compound (I-1b) which is Compound (I-1) wherein A is carboxyl-substituted phenyl Compound (I-1b) can be prepared by the following reaction steps.

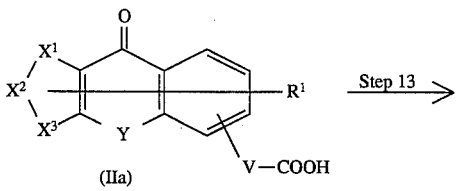

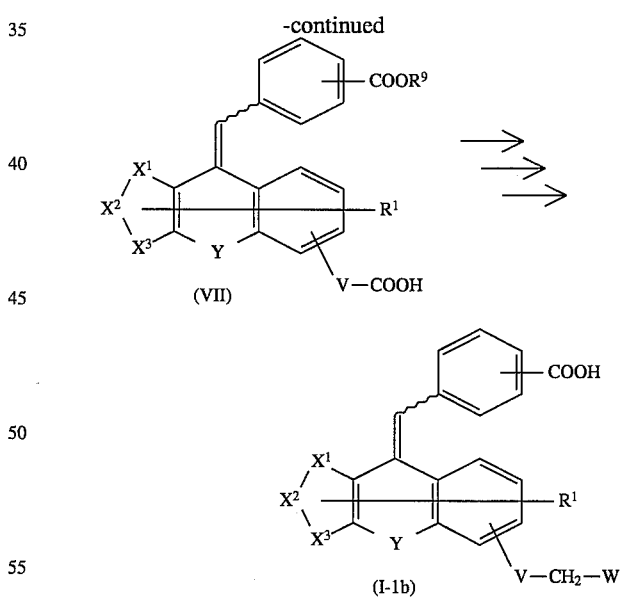

(In the formulae, $R^1$, $R^9$, $X^1$—$X^2$—$X^3$, Y, V and W have the same meanings as defined above.)

(Step 13)

Compound (VII) can be obtained from Compound (IIa) according to the method of Step 1 using diethyl [2-(ethoxycarbonyl)phenyl]methyl phosphonate or dimethyl [2-(methoxycarbonyl)phenyl]methyl phosphonate as the phosphorous acid diester or ethyl 2-[(trimethylsilyl)methyl]benzoate as the organosilicon compound.

Subsequently, Compound (I-1b) can be obtained according to the methods of Steps 2 to 4 and 10.

I-c: Process for preparing Compound (I-1c) which is Compound (I-1) wherein A is tetrazolyl Compound (I-1c) can be prepared by the following reaction steps.

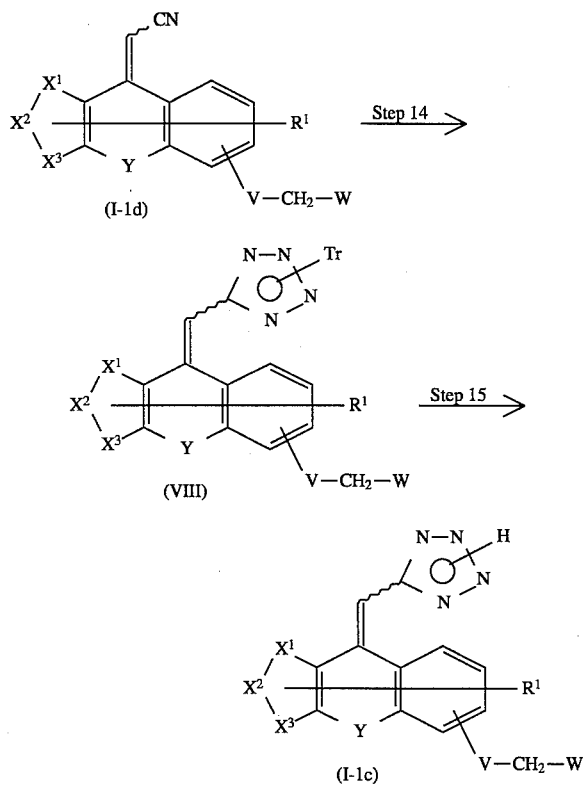

(In the formulae, Tr represents trityl; and $R^1$, $X^1$—$X^2$—$X^3$, Y, V and W have the same meanings as defined above.)

(Step 14)

Compound (I-1d) is reacted with 1 to 30 equivalents of sodium azide in the presence of ammonium chloride in DMF at a temperature of room temperature to 130° C. for one hour to 20 days to give the crude tetrazole compound.

Alternatively, Compound (I-1d) is reacted with 3 to 4 equivalents of sodium azide in the presence of 3 to 4 equivalents of tri-n-butyltin chloride or trimethyltin chloride in toluene at a temperature of 60° C. to the boiling point of the solvent used for 0.5 to 24 days to give the crude tetrazole compound [J. Org. Chem., 56, 2395(1991)].

Compound (VIII) can be obtained by reacting the resulting crude tetrazole compound with 1 to 10 equivalents of trityl chloride in the presence of a suitable base (e.g. triethylamine and pyridine) in an inert solvent such as dichloromethane or DMF, or using the base per se as a solvent, at a temperature of 0° C. to the boiling point of the solvent used for 0.1 to 48 hours.

(Step 15)

Compound (I-1c) can be obtained by treating Compound (VIII) with a suitable acid (e.g. hydrochloric acid, sulfuric acid and p-toluenesulfonic acid) or a suitable base (e.g. lithium hydroxide, sodium hydroxide and potassium hydroxide) in an inert solvent such as a lower alcohol (e.g. methanol and ethanol), THF or dioxane at a temperature of room temperature to the boiling point of the solvent used for 0.1 to 48 hours.

Compound (I-1ca) which is Compound (I-1c) wherein m in V is 0 may also be prepared by the following reaction steps.

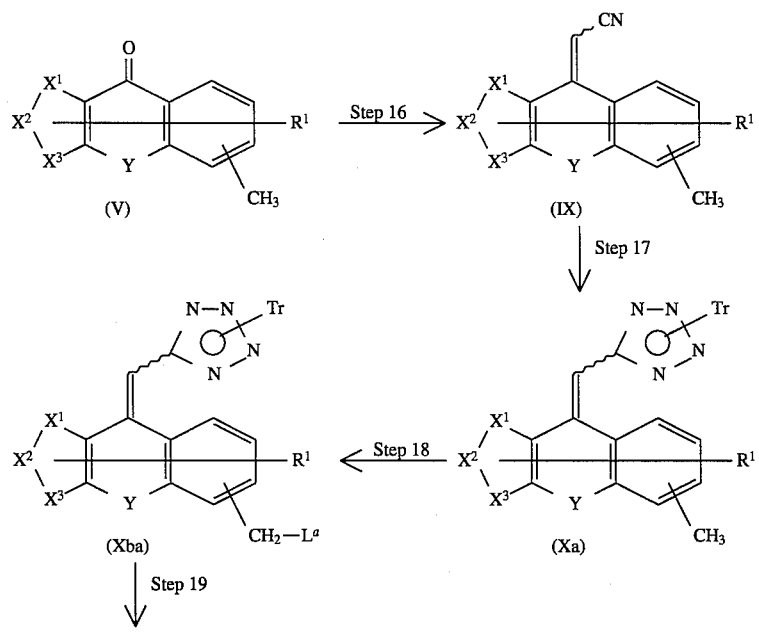

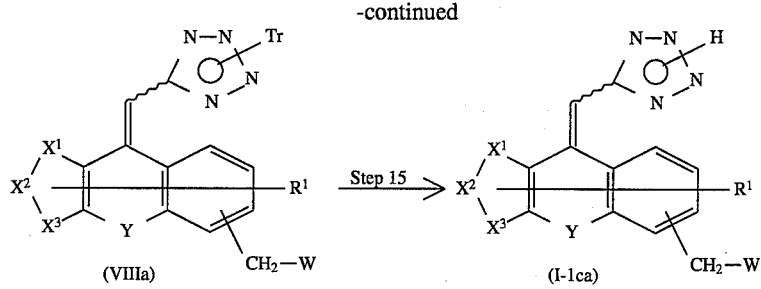

(In the formulae, $R^1$, $X^1$—$X^2$—$X^3$, Y, W, $L^a$ and Tr have the same meanings as defined above.)

(Step 16)

Compound (IX) can be obtained from Compound (V) according to the method of Step 1.

(Step 17)

Compound (Xa) can be obtained from Compound (IX) according to the method of Step 14.

(Step 18)

Compound (Xba) can be obtained from Compound (Xa) according to the method of Step 12.

(Step 19)

Compound (VIIIa) can be obtained from Compound (Xba) according to the method of Step 4.

Subsequently, Compound (I-1ca) can be obtained according to the method of the above Step 15.

Alternatively, Compound (I-1c) may be prepared by the following reaction steps.

(In the formulae, $R^{10}$ represents a protective group for a hydroxyl group; and $R^1$, $X^1$—$X^2$—$X^3$, Y, V, W, L and Tr have the same meanings as defined above.)

Examples of the protective group for a hydroxyl group represented by $R^{10}$ include alkanoyl (e.g. acetyl) and aroyl (e.g. benzoyl) (both will be hereinafter referred to as acyl) as well as methoxymethyl, benzyl, (tert-butyl)dimethylsilyl, and tetrahydropyranyl.
(Step 20)

Compound (IIIe) can be obtained by protecting the hydroxyl group of Compound (IIIb).

In cases where the protective group is acyl, Compound (IIIe) can be obtained by reacting Compound (IIIb) with an equivalent to a large excess of an acid anhydride (e.g. acetic anhydride) or an acid halide (e.g. benzoyl chloride) in the presence of a base (e.g. pyridine, lutidine, collidine, imidazole and triethylamine) in an inert solvent (e.g. dichloromethane and DMF), or using the base per se as a solvent, at a temperature of 0° C. to the boiling point of the solvent used for 0.1 to 24 hours.

In cases where the protective group is methoxymethyl, benzyl or (tert-butyl)dimethylsilyl, the same reaction as in the above acylation is carried out using the corresponding chloromethyl methyl ether, benzyl bromide or (tert-butyl)dimethylsilyl chloride.

In cases where the protective group is tetrahydropyranyl, Compound (IIIe) can be obtained by reacting Compound (IIIb) with an equivalent to a large excess of dihydropyran in the presence of an acid [e.g. p-toluenesulfonic acid and pyridinium p-toluenesulfonate (PPTS)] in an inert solvent (e.g. dichloromethane and THF) at a temperature of 0° C. to the boiling point of the solvent used for 0.1 to 24 hours.
(Step 21)

Compound (Xc) can be obtained from Compound (IIIe) according to the method of Step 14.
(Step 22)

Compound (Xd) can be obtained by removing the protective group for the hydroxyl group in Compound (Xc).

In cases where the protective group is acyl, Compound (Xd) can be obtained by treating Compound (Xc) with a suitable base (e.g. sodium methoxide, sodium hydroxide and potassium hydroxide) in an inert solvent (e.g. THF, methanol, ethanol and dioxane) at a temperature of 0° C. to the boiling point of the solvent used for 0.1 to 24 hours or by treating Compound (Xc) with 0.1 equivalent to a large excess of metal hydride (e.g. lithium aluminum hydride) in an inert solvent (e.g. THF and ether) at a temperature of −78° C. to the boiling point of the solvent used for 0.01 to 48 hours.

In cases where the protective group is methoxymethyl or tetrahydropyranyl, elimination of the protective group is carried out according to the method of the above deacylation in the presence of an acid such as p-toluenesulfonic acid, PPTS, acetic acid, hydrochloric acid or sulfuric acid; and in the case of (tert-butyl)dimethylsilyl, the same reaction is carried out in the presence of tetrabutylammonium fluoride, sodium fluoride, cesium fluoride, or the like.

In cases where the protective group is benzyl, Compound (Xd) can be obtained by subjecting Compound (Xc) to reaction in the presence of a transition metal catalyst used for catalytic hydrogenation (e.g. palladium carbon and platinum) in a hydrogen atmosphere of atmospheric pressure to 100 atm. in an inert solvent (e.g. ethanol, dioxane and acetic acid) at a temperature of 0° to 250° C. for 0.1 to 48 hours.
(Step 23)

Compound (Xb) can be obtained from Compound (Xd) according to the method of Step 3.

Subsequently, Compound (I-1c) can be obtained according to the methods of the above Steps 19 and 15.
Process 2
Compound (I-2) [Compound (I) wherein $Z^1$—$Z^2$ is CH—CH(COOH)— and A is carboxyl]

Compound (I-2) can be prepared by the following reaction steps.

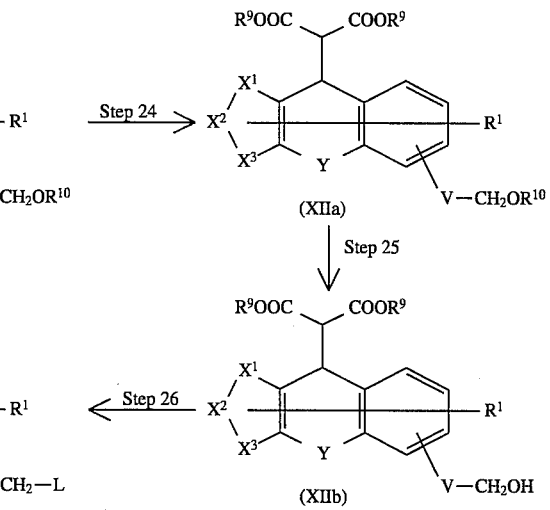

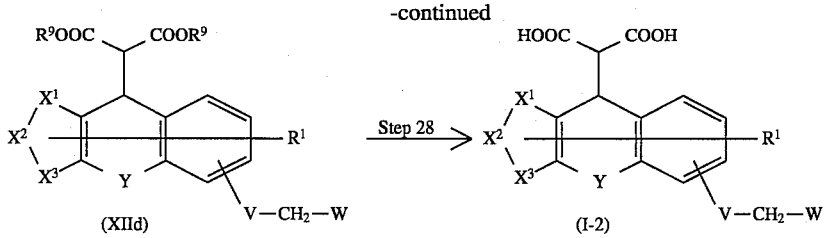

(In the formulae, $R^1$, $R^9$, $R^{10}$, $X^1$—$X^2$—$X^3$, Y, V, W and L have the same meanings as defined above.)

The starting compound (XI) can be obtained by a known method (Japanese Published Unexamined Patent Application No. 250/90) or a method similar thereto.

(Step 24)

Compound (XIIa) can be obtained by reacting Compound (XI) with an equivalent to a large excess of a malonate in the presence of a catalytic amount to a large excess of a Lewis acid, a protonic acid or an acid anhydride, and if necessary, in the presence of an equivalent to a large excess of an amine, in an inert solvent (e.g. dichloromethane, dichloroethane, benzene and toluene), or using the malonate per se as a solvent, at a temperature of –100° C. to the boiling point of the solvent used for 0.1 to 100 hours.

Examples of the Lewis acid, protonic acid and acid anhydride applicable are titanium tetrachloride, tin tetrachloride, aluminum chloride, zinc chloride, boron trifluoride, trimethylsilyl triflate, trimethylsilyl iodide, trimethylsilyl bromide, trimethylsilyl chloride, titanium tetraisopropoxide, silica gel, alumina, Nafion (registered trademark), sulfuric acid, hydrochloric acid, trifluoroacetic acid, methanesulfonic acid, trifluoromethanesulfonic acid, trichloroacetic acid, polyphosphoric acid, p-toluenesulfonic acid, trifluoroacetic anhydride, trichloroacetic anhydride, acetic anhydride and trifluoromethanesulfonic anhydride.

Examples of the amine are triethylamine, diisopropylethylamine, tributylamine, dicyclohexylmethylamine, N-methylmorpholine, N-methylpiperidine and Proton Sponge (registered trademark).

(Step 25)

Compound (XIIb) can be obtained from Compound (XIIa) according to the method of Step 22.

(Step 26)

Compound (XIIc) can be obtained from Compound (XIIb) according to the method of Step 3.

(Step 27)

Compound (XIId) can be obtained from Compound (XIIc) according to the method of Step 4.

(Step 28)

Compound (I-2) can be obtained by hydrolysis of Compound (XIId). The hydrolysis is carried out by treating Compound (XIId) with a suitable base (e.g. lithium hydroxide, sodium hydroxide and potassium hydroxide) in a suitable aqueous solvent (e.g. methanol, ethanol, THF and dioxane) at a temperature of room temperature to the boiling point of the solvent used for 0.1 to 48 hours.

Process 3

Compound (I-3) [Compound (I) wherein $Z^1$—$Z^2$ is CH—$CH_2$]

3-a: Process for preparing Compound (I-3a) which is Compound (I-3) wherein A is carboxyl Compound (I-3a) can be prepared by the following reaction step.

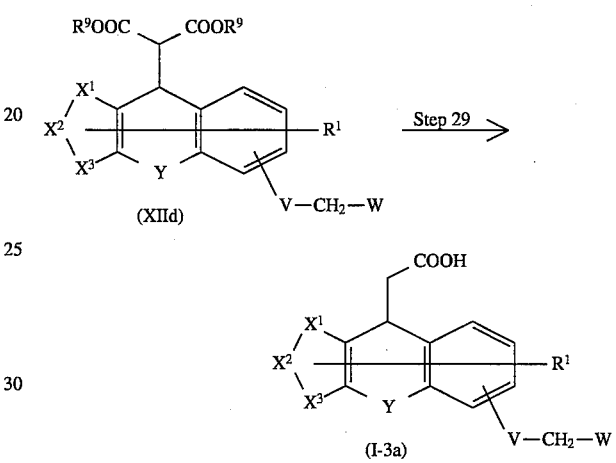

(In the formulae, $R^1$, $R^9$, $X^1$—$X^2$—$X^3$, Y, V and W have the same meanings as defined above.)

(Step 29)

Compound (I-3a) can be obtained by hydrolysis of Compound (XIId). The hydrolysis is carried out by treating Compound (XIId) with a suitable base (e.g. lithium hydroxide, sodium hydroxide and potassium hydroxide) in a suitable aqueous solvent (e.g. methanol, ethanol, THF and dioxane) at a temperature of room temperature to the boiling point of the solvent used for 0.1 to 48 hours.

In cases where the reaction ceases after the hydrolysis and does not proceed to decarboxylation, the obtained intermediate is further subjected to reaction in the presence of piperidine in pyridine at a temperature of 50° C. to the boiling point of the solvent used for 0.1 to 48 hours, whereby the desired compound is obtained.

3-b: Process for preparing Compound (I-3b) which is Compound (I-3) wherein A is carboxy -substituted phenyl Compound (I-3b) can be prepared by the following reaction steps.

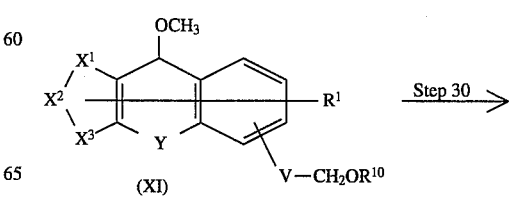

-continued

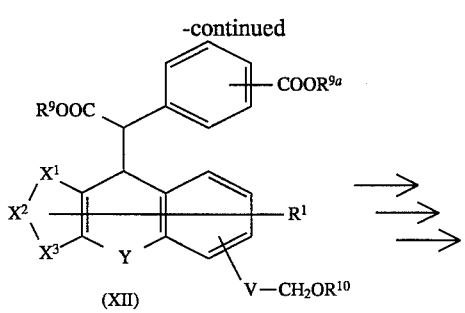

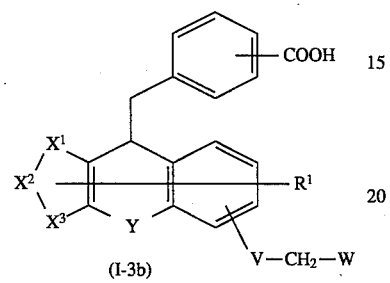

(In the formulae, $R^{9a}$ has the same meaning as $R^9$; and $R^1$, $R^9$, $R^{10}$, $X^1$—$X^2$—$X^3$, Y, V and W have the same meanings as defined above.)
(Step 30)

Compound (XIII) can be obtained from Compound (XI) according to the method of Step 24 using a benzoate such as ethyl 2-[(ethoxycarbonyl)methyl]benzoate in place of the malonate.

Subsequently, Compound (I-3b) can be obtained according to the methods of Steps 25 to 27 and 29.

3-c: Process for preparing Compound (I-3c) which is Compound (I-3) wherein A is tetrazolyl and Compound (I-3d) which is Compound (I-3) wherein A is cyano Compound (I-3c) and Compound (I-3d) can be prepared by the following reaction steps.

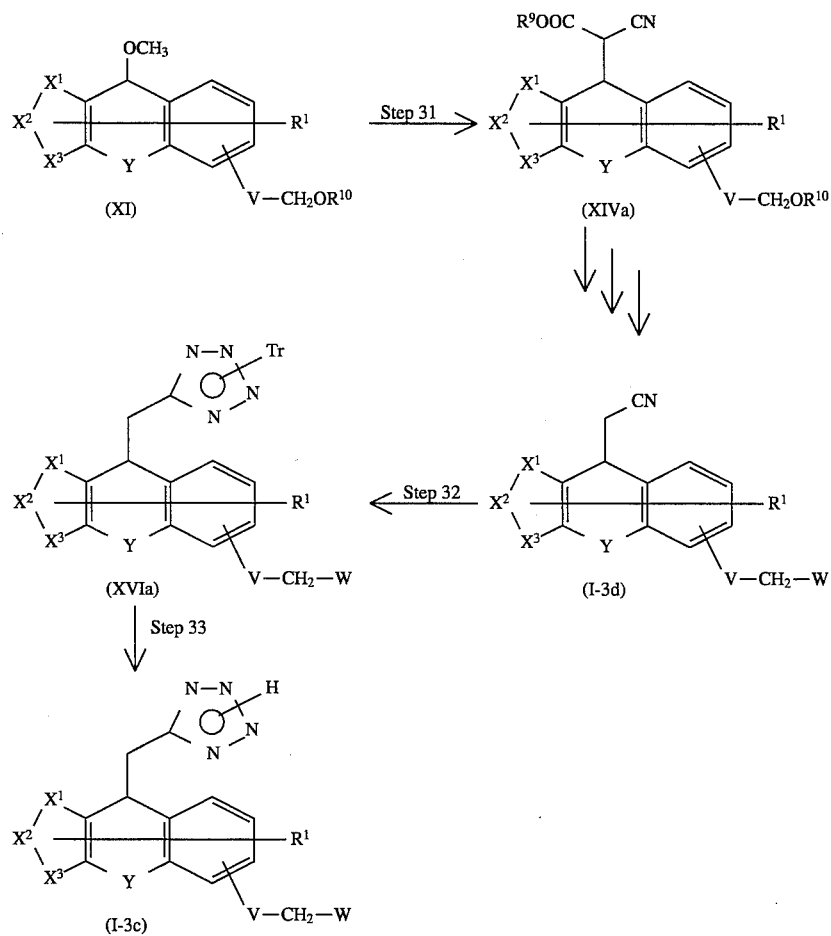

(In the formulae, $R^1$, $R^9$, $R^{10}$, $X^1$—$X^2$—$X^3$, Y, V, W and Tr have the same meanings as defined above.)

(Step 31)

Compound (XIVa) can be obtained from Compound (XI) according to the method of Step 24 using a cyanoacetate in place of the malonate.

Subsequently, Compound (I-3d) can be obtained according to the methods of Steps 25 to 27 and 29.

(Step 32)

Compound (XVIa) can be obtained from Compound (I-3d) according to the method of Step 14.

(Step 33)

Compound (I-3c) can be obtained from Compound (XVIa) according to the method of Step 15.

Alternatively, Compound (I-3c) can be prepared by the following reaction steps.

(In the formulae, $R^1$, $R^9$, $R^{9a}$, $X^1$—$X^2$—$X^3$, Y, V, W and Tr have the same meanings as defined above.)

The starting compound (XVII) can be obtained by a known method (Japanese Published Unexamined Patent Application No. 250/90) or a method similar thereto.

(Step 34)

Compound (XVII) is reacted with an equivalent to a large excess of thionyl chloride, in the presence of an inert solvent (e.g. dichloromethane and dichloroethane) if necessary, at a temperature of −50° C. to the boiling point of the solvent used for 0.1 to 48 hours to give a compound wherein OH is replaced by Cl.

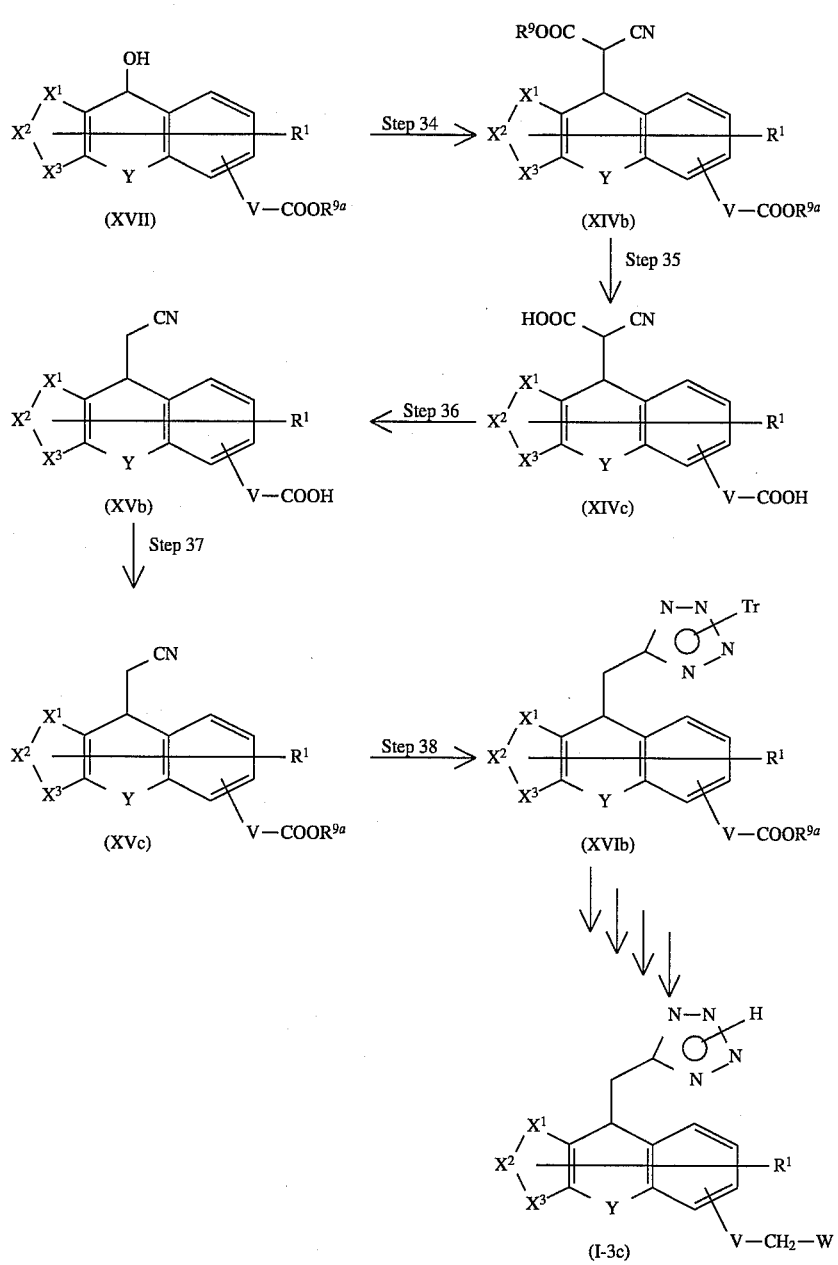

Compound (XIVb) can be obtained by reacting the above compound with an equivalent to a large excess of a cyanoacetate in the presence of a suitable base (e.g. sodium hydride, potassium hydride, butyl lithium, LDA and potassium tert-butoxide) in an inert solvent (e.g. dichloromethane, DMF, THF and toluene) at a temperature of 0° C. to the boiling point of the solvent used for 0.1 to 48 hours.
(Step 35)

Compound (XIVc) can be obtained from Compound (XIVb) according to the method of Step 10.
(Step 36)

Compound (XVb) can be obtained by subjecting Compound (XIVc) to reaction in the presence of piperidine in pyridine at a temperature of 50° C. to the boiling point of the solvent used for 0.1 to 48 hours.
(Step 37)

Compound (XVc) can be obtained by reacting Compound (XVb) with a lower alcohol (e.g. methanol and ethanol) in the presence of a catalytic amount of an acid (e.g. sulfuric acid) using the lower alcohol per se as a solvent at a temperature of 0° C. to the boiling point of the solvent used for 0.1 to 48 hours.
(Step 38)

Compound (XVIb) can be obtained from Compound (XVc) according to the method of Step 14.

Subsequently, Compound (I-3c) can be obtained according to the methods of Steps 2 to 4 and 15.

Process 4

Compound (I-4) [Compound (I) wherein $Z^1$—$Z^2$ is N—$CH_2$]

4-a: Process for preparing Compound (I-4a) which is Compound (I-4) wherein A is cyano and m in V is 0

Compound (I-4a) can be prepared by the following reaction steps.

(In the formulae, $R^{11}$ represents hydrogen or benzyl; and $R^1$, $R^{10}$, $X^1$—$X^2$—$X^3$, Y and W have the same meanings as defined above.)

The starting compound (XVIII) can be obtained by a known method [Chem. Absts., 72, 43496v (1970); ibid., 60, 2916a (1964); and Heterocyclic Compounds, 43, Part I, 392(1984)] or a method similar thereto.
(Step 39)

Compound (XIXa) can be obtained by treating Compound (XVIII) with 1 to 10 equivalents of a reducing agent (e.g. sodium borohydride and lithium aluminum hydride) in an inert solvent (e.g. THF and methanol) at a temperature of −50° C. to the boiling point of the solvent used for 0.1 to 10 hours.
(Step 40)

Compound (XIXb) can be obtained from Compound (XIXa) according to the method of Step 20.
(Step 41)

Compound (Xvd) can be obtained by reacting Compound (XIXb) with a nitrile compound (e.g. iodoacetonitrile, bromoacetonitrile and chloroacetonitrile) in the presence of a suitable base (e.g. sodium hydride, potassium hydride, butyl lithium, LDA, potassium tert-butoxide and sodium amide), and if necessary, in the presence of sodium iodide or potassium iodide, in an inert solvent (e.g. benzene, toluene, dioxane, THF, DMF and DMSO) at a temperature of −100° C. to the boiling point of the solvent used for 0.1 to 48 hours.

Alternatively, Compound (XVd) can be obtained by reacting Compound (XIXb) with an equivalent to a large excess of formalin or paraformaldehyde, and a prussiate (e.g. sodium cyanide and potassium cyanide) in the presence of acetic acid and/or trifluoroacetic acid in an inert solvent (e.g. dichloroethane, dioxane, THF and ethanol), or using acetic acid and/or trifluoroacetic acid per se as a solvent, at a

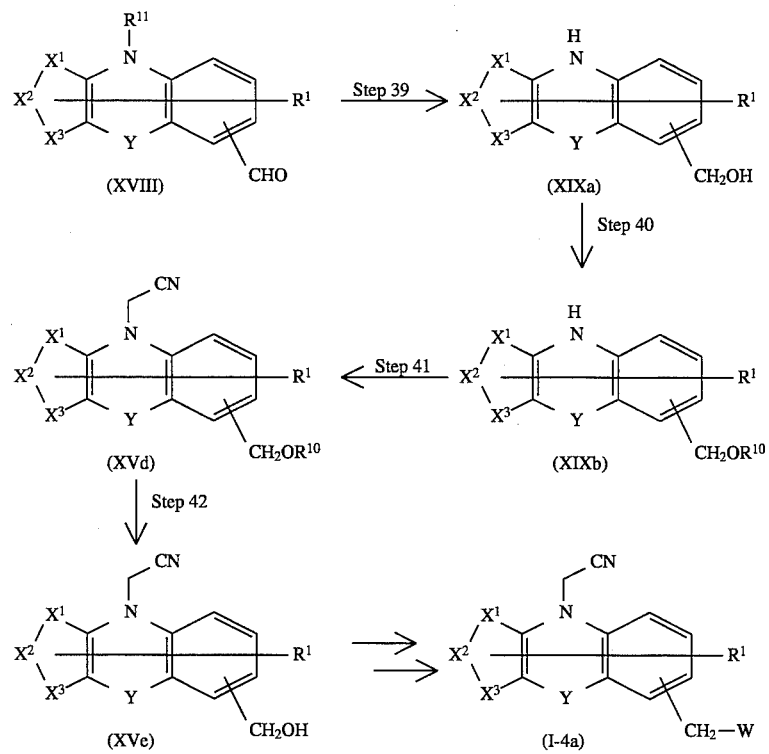

temperature of 0° C. to the boiling point of the solvent used for 0.1 to 48 hours.
(Step 42)

Compound (XVe) can be obtained from Compound (XVd) according to the method of Step 22.

Subsequently, Compound (I-4a) can be obtained according to the methods of Steps 3 and 4.

Compound (I-4aa) which is Compound (I-4a) wherein V is oriented at the para-position from the N atom in the tricyclic system may also be prepared by the following reaction steps.

(Step 44)

Compound (XXI) can be obtained by reacting Compound (XIXc) with a mixed acid anhydride prepared from acetic acid and formic acid in dichloroethane at room temperature for about one day.
(Step 45)

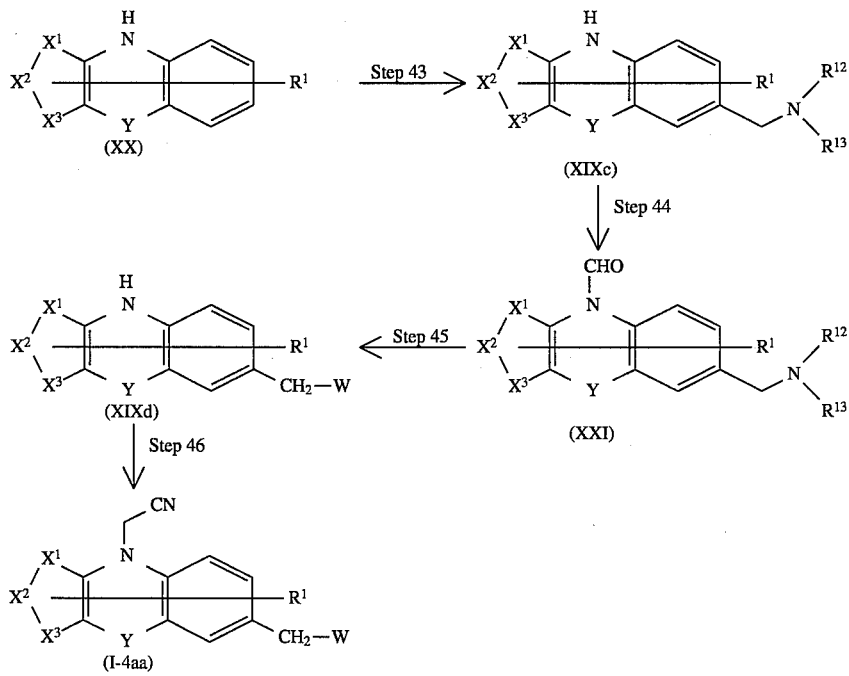

{In the formulae, $R^{12}$ and $R^{13}$ independently represent lower alkyl or are combined together to represent —$(CH_2)_2$—P—$(CH_2)_l$— [wherein P is CH, O, S or $NR^{14}$ (wherein $R^{14}$ is lower alkyl) and l is 2 or 3] as —$R^{12}$—$R^{13}$—; and $R^1$, $X^1$—$X^2$—$X^3$, Y and W have the same meanings as defined above.}

The lower alkyl represented by $R^{12}$, $R^{13}$ and $R^{14}$ has the same meaning as defined above.

The starting compound (XX) can be obtained according to a known method [Bull. Soc. Chim. Fr., 185(1981)].
(Step 43)

Compound (XIXc) can be obtained by reacting Compound (XX) with an equivalent to a large excess of formalin or paraformaldehyde, and a secondary amine (e.g. N-methylpiperazine, piperidine and dialkylamine) in the presence of acetic acid and/or trifluoroacetic acid in an inert solvent (e.g. dichloroethane, dioxane, THF and ethanol), or using acetic acid and/or trifluoroacetic acid per se as a solvent, at a temperature of 0° C. to the boiling point of the solvent used for 1 to 48 hours.

Compound (XXI) is reacted with an equivalent to a large excess of a chloroformate (e.g. ethyl chloroformate and isobutyl chloroformate) in an inert solvent (e.g. dichloromethane, dichloroethane and ethyl acetate) at a temperature of –50° C. to the boiling point of the solvent used for 0.1 to 24 hours to give a compound wherein —$NR^{12}R^{13}$ is replaced by Cl. Subsequently, Compound (XIXd) can be obtained according to the method of Step 4.

In cases where the reaction does not proceed to deformylation, the obtained intermediate is treated with a base (e.g. sodium methoxide and sodium ethoxide) in an inert solvent (e.g. dioxane) at a temperature of 0° C. to the boiling point of the solvent used for 0.1 to 48 hours, whereby the desired compound is obtained.
(Step 46)

Compound (I-4aa) can be obtained from Compound (XIXd) according to the method of Step 41.

Alternatively, Compound (I-4aa) can be prepared by the following reaction steps.

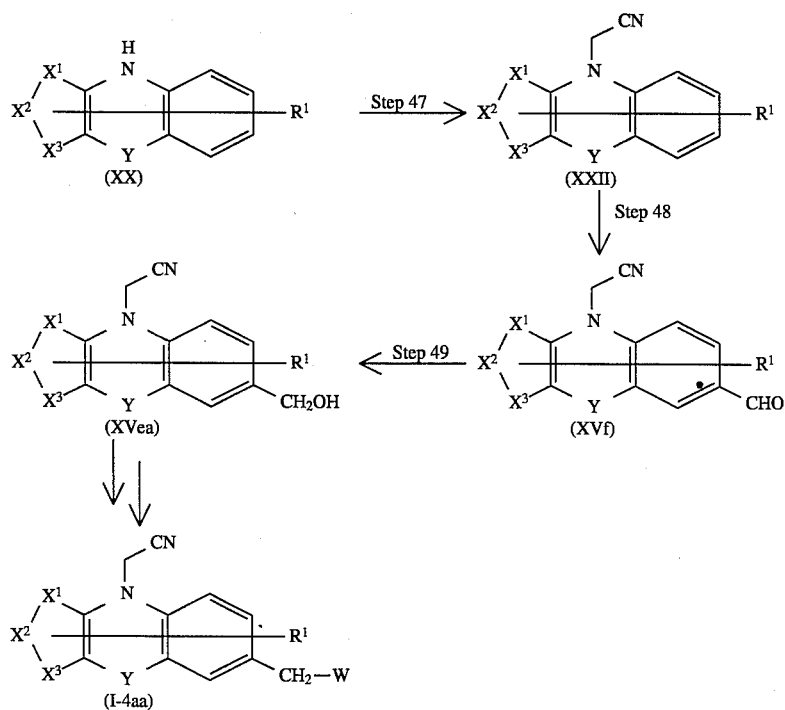

(In the formulae, $R^1$, $X^1$—$X^2$—$X^3$, Y and W have the same meanings as defined above.)

(Step 47)

Compound (XXII) can be obtained from Compound (XX) according to the method of Step 41.

(Step 48)

Compound (XVf) can be obtained by reacting Compound (XXII) with phosphorous oxychloride and DMF or methylformanilide, in the presence of an inert solvent such as dichloroethane if necessary, at a temperature of room temperature to 100° C. for 1 to 24 hours. Preferably, the reaction is carried out using 3 equivalents of phosphorous oxychloride and 3 equivalents of methylformanilide in the presence of dichloroethane at a temperature of 70° to 90° C. for 5 to 15 hours.

(Step 49)

Compound (XVea) can be obtained from Compound (XVf) according to the method of Step 39.

Subsequently, Compound (I-4aa) can be obtained according to the methods of Steps 3 and 4.

Further, Compound (I-4aa) can also be prepared by the following reaction steps.

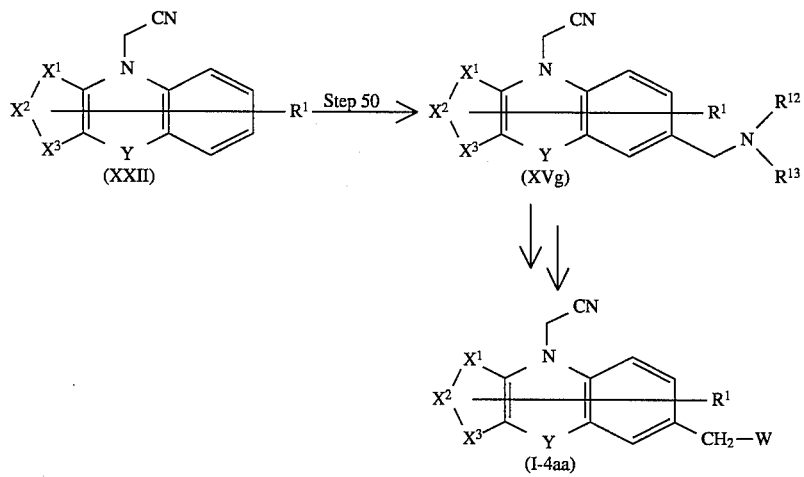

(In the formulae, $R^1$, $R^{12}$, $R^{13}$, $X^1$—$X^2$—$X^3$, Y and W have the same meanings as defined above.)

(Step 50)

Compound (XVg) can be obtained from Compound (XXII) according to the method of Step 43.

Subsequently, Compound (I-4aa) can be obtained according to the method of Step 45.

4-b: Process for preparing Compound (I-4b) which is Compound (I-4) wherein A is carboxyl and m in V is 0

Compound (I-4b) can be prepared by the following reaction step.

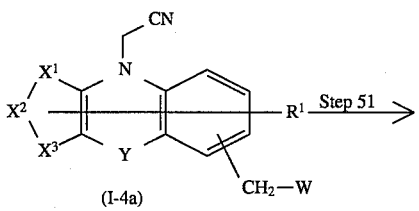

(I-4a)

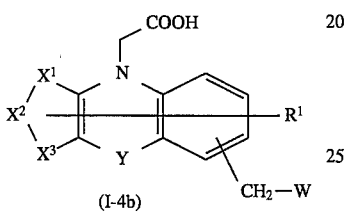

(I-4b)

(In the formulae, $R^1$, $X^1$—$X^2$—$X^3$, Y and W have the same meanings as defined above.)

(Step 51)

Compound (I-4b) can be obtained from Compound (I-4a) according to the method of Step 5.

4-c: Process for preparing Compound (I-4c) which is Compound (I-4) wherein A is carboxyl-substituted phenyl, m in V is 0 and V is oriented at the para-position from the N atom in the tricyclic system Compound (I-4c) can be prepared by the following reaction steps.

(Step 52)

Compound (XXIIIa) can be obtained from Compound (XX) according to the method of Step 41 using a benzoate [e.g. ethyl 2-(chloromethyl)benzoate] in place of the nitrile compound.

(Step 53)

Compound (XXIIIb) can be obtained from Compound (XXIIIa) according to the method of Step 48.

Subsequently, Compound (I-4c) can be obtained according to the methods of Steps 39, 3, 4 and 10.

4-d: Process for preparing Compound (I-4d) which is Compound (I-4) wherein A is tetrazolyl and m in V is 0

Compound (I-4d) can be prepared by the following reaction steps.

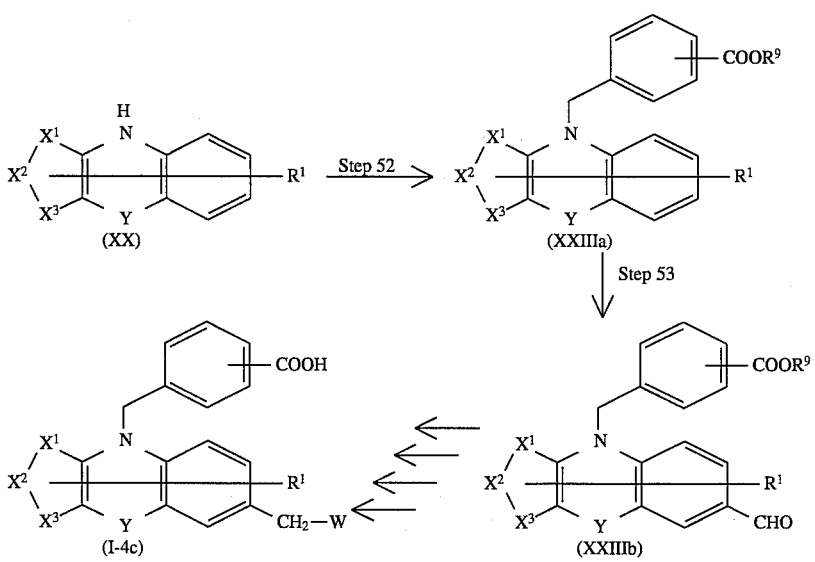

(In the formulae, $R^1$, $R^9$, $X^1$—$X^2$—$X^3$, Y and W have the same meanings as defined above.)

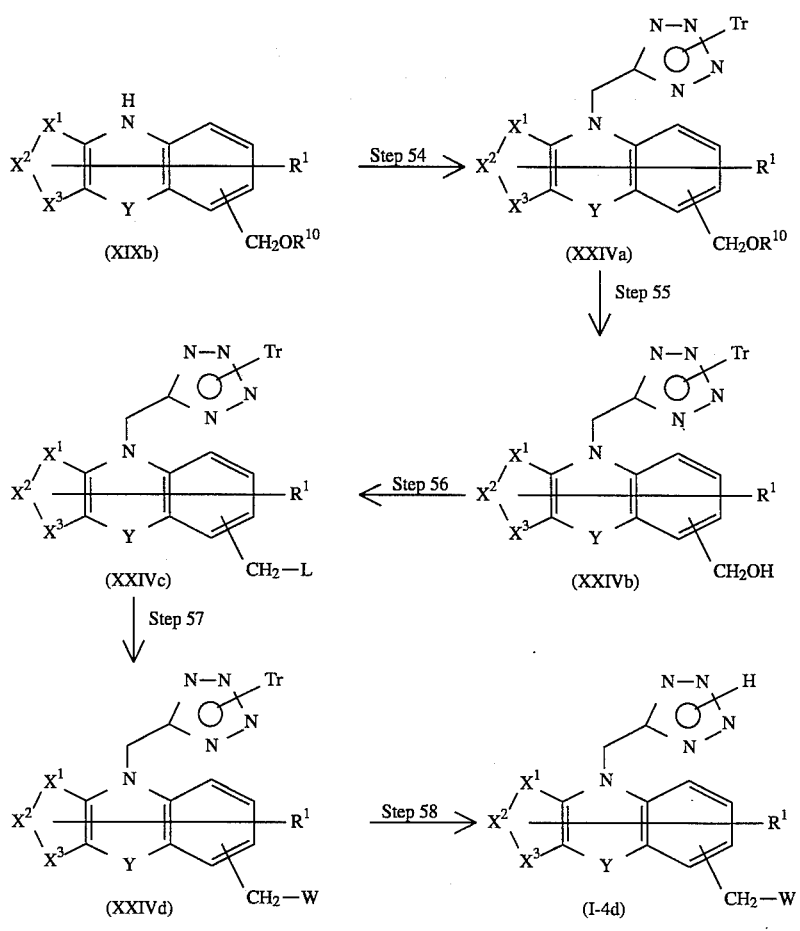

(In the formulae, $R^1$, $R^{10}$, $X^1$—$X^2$—$X^3$, Y, L, W and Tr have the same meanings as defined above.)

(Step 54)

Compound (XXIVa) can be obtained from Compound (XIXb) according to the method of Step 41 using N-tritylchloromethyltetrazole in place of the nitrile compound.

(Step 55)

Compound (XXIVb) can be obtained from Compound (XXIVa) according to the method of Step 22.

(Step 56)

Compound (XXIVc) can be obtained from Compound (XXIVb) according to the method of Step 3.

(Step 57)

Compound (XXIVd) can be obtained from Compound (XXIVc) according to the method of Step 4.

(Step 58)

Compound (I-4d) can be obtained from Compound (XXIVd) according to the method of Step 15.

Alternatively, Compound (I-4d) can be prepared by the following reaction steps.

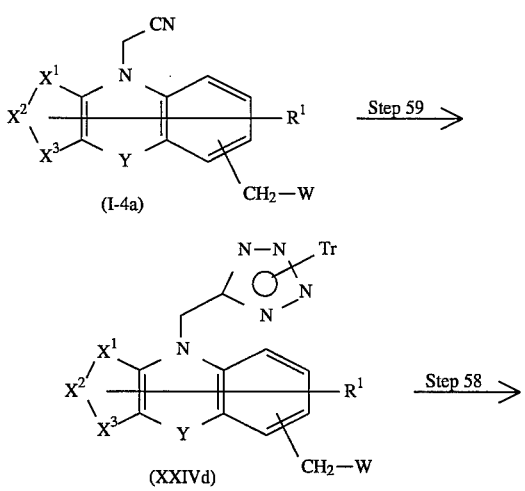

-continued

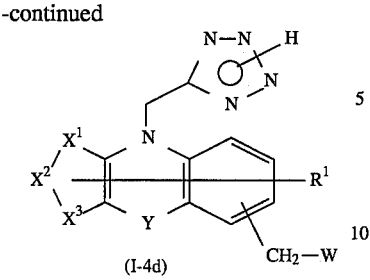

(I-4d)

(In the formulae, $R^1$, $X^1$—$X^2$—$X^3$, Y, W and Tr have the same meanings as defined above.)

(Step 59)

Compound (XXIVd) can be obtained from Compound (I-4a) according to the method of Step 14.

Subsequently, Compound (I-4d) can be obtained according to the method of the above Step 58.

Compound (I-4aaa) and Compound (I-4da) which are respectively Compound (I-4a) and Compound (I-4d) wherein W represents

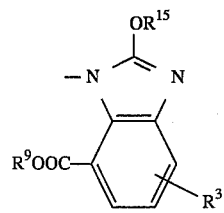

(wherein $R^{15}$ is lower alkyl; and $R^3$ and $R^9$ have the same meanings as defined above) and V is oriented at the para-position from the N atom in the tricyclic system may also be prepared by the following reaction steps.

The lower alkyl represented by $R^{15}$ has the same meaning as defined above.

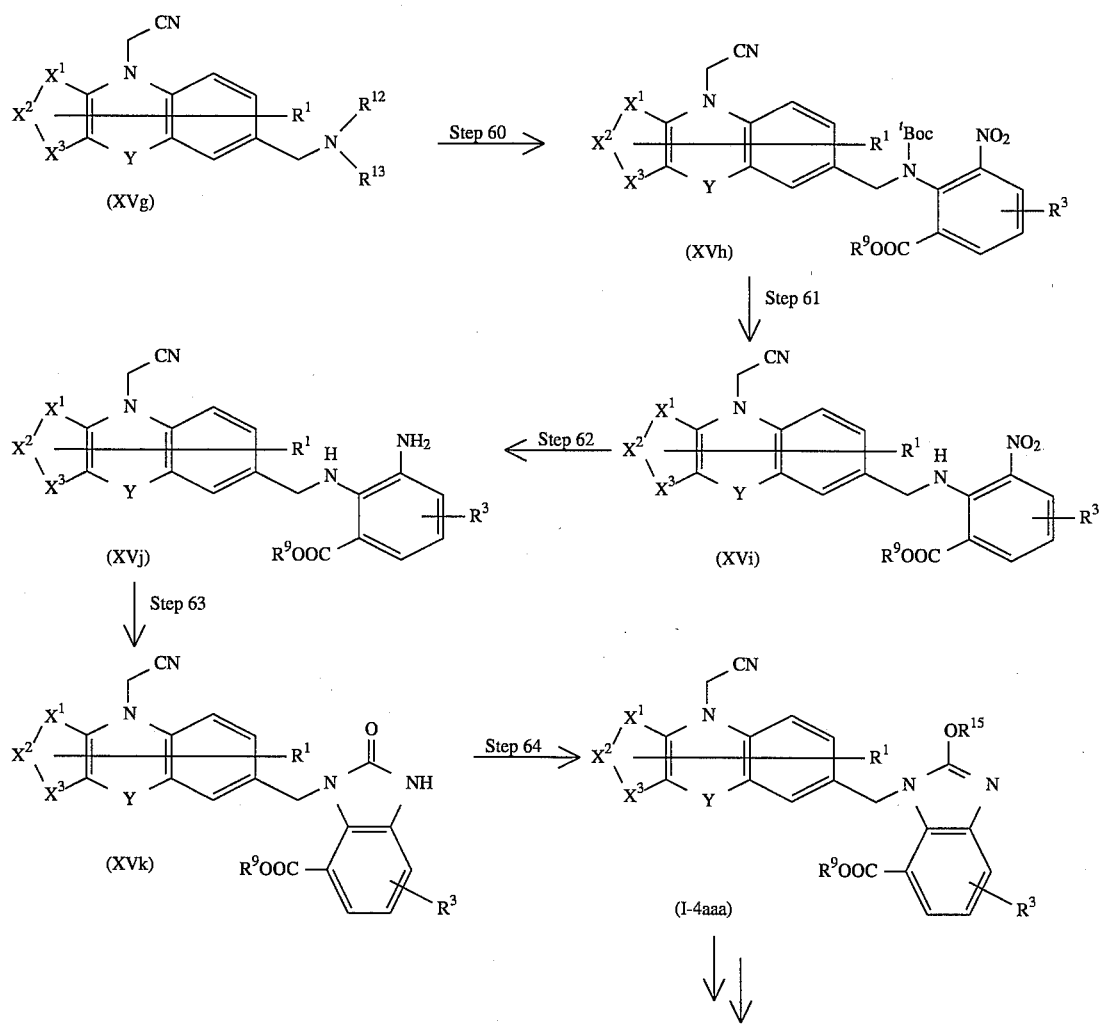

-continued

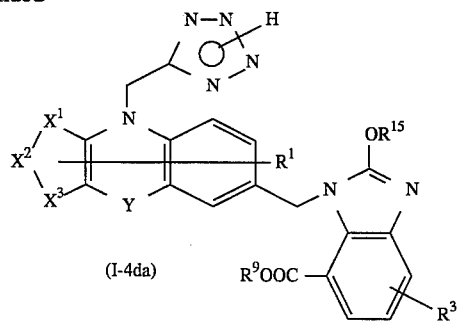

(In the formulae, 'Boc is t-butoxycarbonyl; and $R^1$, $R^3$, $R^9$, $R^{12}$, $R^{13}$, $R^{15}$, $X^1$—$X^2$—$X^3$ and Y have the same meanings as defined above.)

(Step 60)

Compound (XVh) can be obtained from Compound (XVg) according to the method of Step 45 using a compound represented by the formula

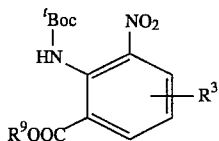

(wherein 'Boc, $R^3$ and $R^9$ have the same meanings as defined above), which can be obtained according to the method described in Japanese Published Unexamined Patent Application No. 9373/92, in place of the compound represented by the formula H—W.

(Step 61)

Compound (XVi) can be obtained by treating Compound (XVh) with trifluoroacetic acid in an inert solvent (e.g. dichloroethane, dioxane, THF and ethanol), or using trifluoroacetic acid per se as a solvent, at a temperature of 0° C. to the boiling point of the solvent used for 0.1 to 48 hours.

(Step 62)

Compound (XVj) can be obtained by subjecting Compound (XVi) to reaction in the presence of a transition metal catalyst used for catalytic hydrogenation (e.g. palladium carbon and platinum) in a hydrogen atmosphere of atmospheric pressure to 100 atm. in an inert solvent (e.g. ethanol, dioxane and acetic acid) at a temperature of 0 to 250° C. for 0.1 to 48 hours, or by subjecting Compound (XVi) to reaction in the presence of excess iron, tin, zinc, or the like in an inert solvent (e.g. hydrochloric acid and acetic acid) at a temperature of 0° C. to the boiling point of the solvent used for 0.1 to 24 hours.

(Step 63)

Compound (XVk) can be obtained by reacting Compound (XVj) with an equivalent to a large excess of a chloroformate (e.g. ethyl chloroformate and isobutyl chloroformate) in the presence of a base (e.g. pyridine and triethylamine) in an inert solvent (e.g. dichloromethane, dichloroethane and ethyl acetate), or using pyridine per se as a solvent, at a temperature of 0° C. to room temperature for 0.1 to 24 hours, and then treating the obtained intermediate with a base (e.g. sodium methoxide and sodium ethoxide) in a lower alcohol (e.g. methanol and ethanol) at a temperature of 0° C. to the boiling point of the alcohol used for 0.1 to 48 hours.

(Step 64)

Compound (I-4aaa) can be obtained by reacting Compound (XVk) with phosphorous oxychloride at a temperature of room temperature to 100° C. for 0.5 to 24 hours, and then treating the obtained intermediate with a base (e.g. sodium methoxide and sodium ethoxide) in a lower alcohol (e.g. methanol and ethanol) at a temperature of room temperature to the boiling point of the alcohol used for 0.1 to 48 hours.

Subsequently, Compound (I-4da) can be obtained according to the methods of Steps 14 and 15.

4-e: Process for preparing Compound (I-4e) which is Compound (I-4) wherein A is cyano-substituted phenyl, m in v is 0 and V is oriented at the para-position from the N atom in the tricyclic system and Compound (I-4f) which is Compound (I-4) wherein A is tetrazolyl-substituted phenyl, m in V is 0 and V is oriented at the para-position from the N atom in the tricyclic system Compound (I-4e) and Compound (I-4f) can be prepared by the following reaction steps.

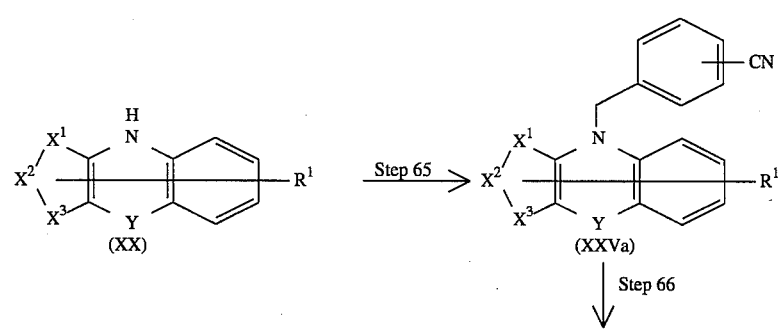

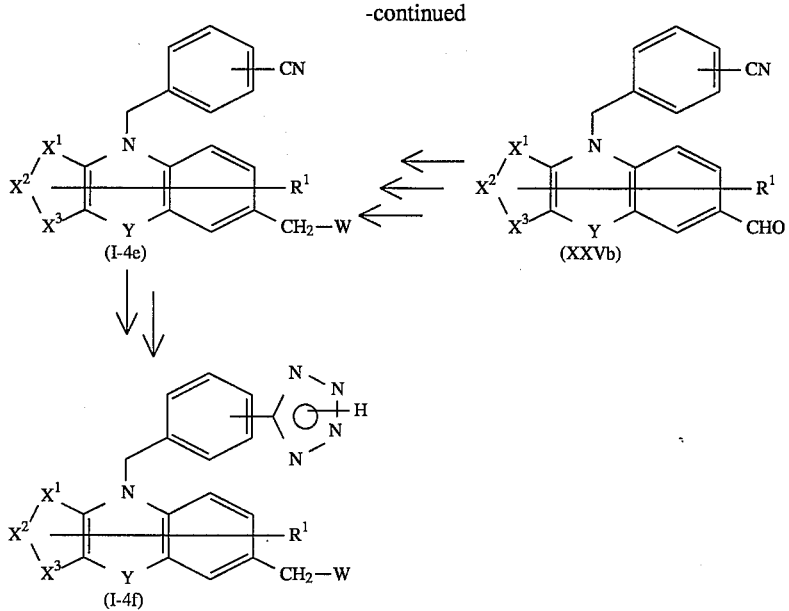

(In the formulae, $R^1$, $X^1$—$X^2$—$X^3$, Y and W have the same meanings as defined above.)

(Step 65)

Compound (XXVa) can be obtained from Compound (XX) according to the method of Step 41 using a benzyl halide (e.g. 2-cyanobenzylbromide) in place of the nitrile compound.

(Step 66)

Compound (XXVb) can be obtained from Compound (XXVa) according to the method of Step 48.

Subsequently, Compound (I-4e) can be obtained according to the methods of Steps 39, 3 and 4, and Compound (I-4f) can be obtained from Compound (I-4e) according to the methods of Steps 14 and 15.

Process 5

Compound (I-5) [Compound (I) wherein $Z^1$—$Z^2$ is N—$CH_2CH_2$]

5: Process for preparing Compound (I-5a) which is Compound (I-5) wherein A is cyano, m in V is 0 and V is oriented at the para-position from the N atom in the tricyclic system and Compound (I-5b) which is Compound (I-5) wherein A is tetrazolyl, m in V is 0 and V is oriented at the para-position from the N atom in the tricyclic system Compound (I-5a) and Compound (I-5b) can be prepared by the following reaction steps.

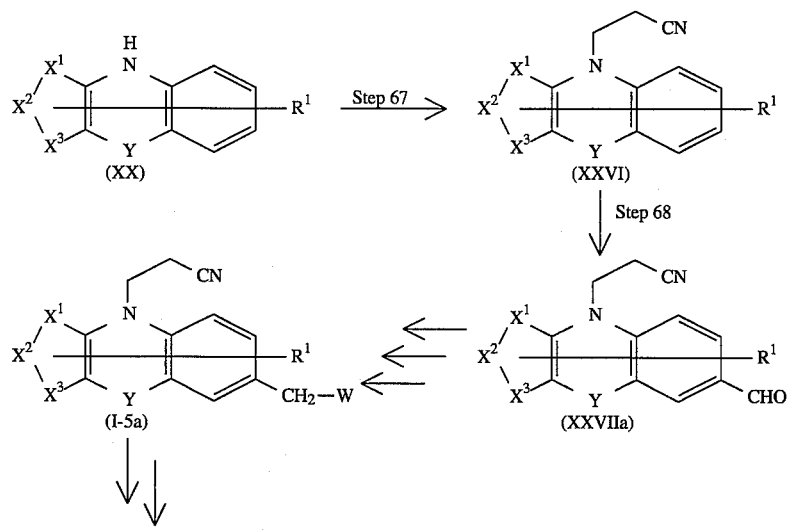

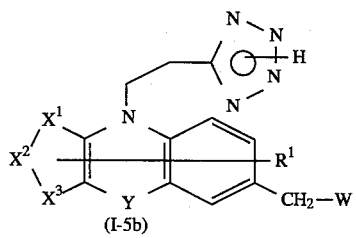

(I-5b)

(In the formulae, $R^1$, $X^1$—$X^2$—$X^3$, Y and W have the same meanings as defined above.)

(Step 67)

Compound (XXVI) can be obtained by reacting Compound (XX) with an equivalent to a large excess of acrylonitrile in the presence of a catalytic amount of Triton B in an inert solvent such as benzene or toluene at a temperature of room temperature to the boiling point of the solvent used for 0.5 to 24 hours [Yakugaku Zasshi, 76, 640(1956)].

(Step 68)

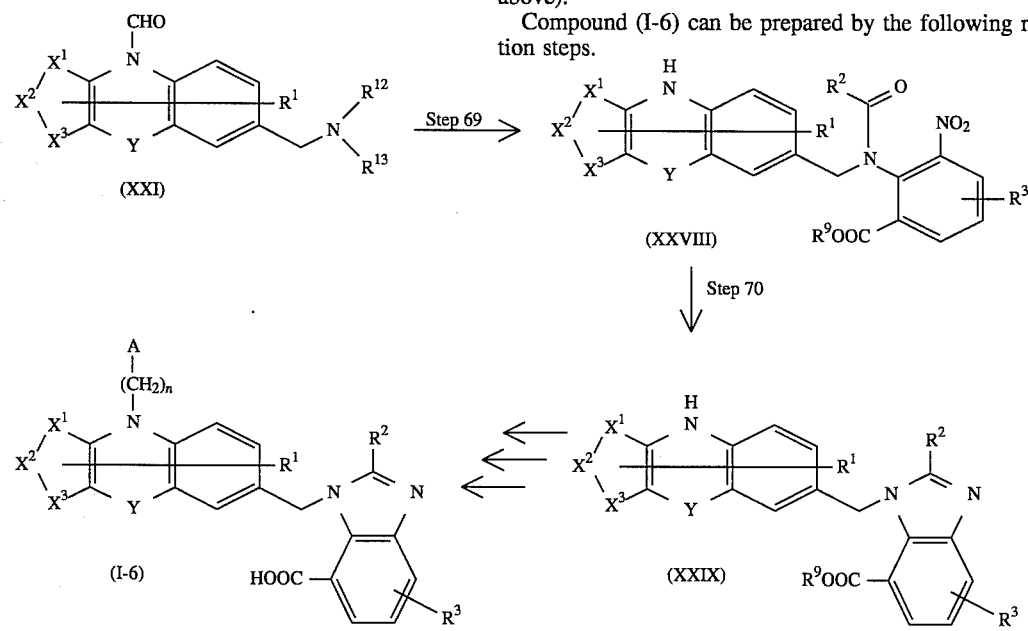

Compound (XXVIIa) can be obtained from Compound (XXVI) according to the method of Step 48.

Subsequently, Compound (I-5a) can be obtained according to the methods of Steps 39, 3 and 4, and Compound (I-5b) can be obtained from Compound (I-5a) according to the methods of Steps 14 and 15.

Process 6

Process for preparing Compound (I-6) which is Compound (I) wherein $Z^1$—$Z^2$ is N—$(CH_2)_n$—, m in V is 0, V is oriented at the para-position from the N atom in the tricyclic system, and W is

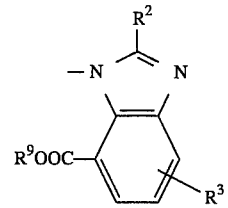

(wherein $R^2$, $R^3$ and $R^9$ have the same meanings as defined above).

Compound (I-6) can be prepared by the following reaction steps.

(In the formulae, $R^1$, $R^2$, $R^3$, $R^9$, $R^{12}$, $R^{13}$, $X^1$—$X^2$—$X^3$ and Y have the same meanings as defined above.)

(Step 69)

Compound (XXVIII) can be obtained from Compound (XXI) according to the method of Step 45 using a compound represented by the formula

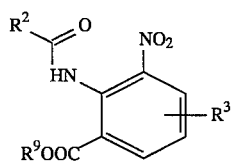

(wherein $R^2$, $R^3$ and $R^9$ have the same meanings as defined above), which can be obtained according to the method described in Japanese Published Unexamined Patent Application No. 9373/92, in place of the compound represented by the formula H—W.

(Step 70)

Compound (XXIX) can be obtained by subjecting Compound (XXVIII) to reaction in the presence of a transition metal catalyst used for catalytic hydrogenation (e.g. palladium carbon and platinum) in a hydrogen atmosphere of atmospheric pressure to 100 atm. in an inert solvent (e.g. ethanol, dioxane and acetic acid) at a temperature of 0° to 250° C. for 0.1 to 48 hours, or by heating Compound (XXVIII) under reflux in the presence of excess iron, tin, zinc, or the like in an inert solvent (e.g. hydrochloric acid and acetic acid) for 0.1 to 24 hours.

In cases where the reaction ceases after reduction and does not proceed to cyclization in the catalytic hydrogenation in a solvent such as ethanol or dioxane, the obtained intermediate is heated under reflux after addition of a small amount of an acid (e.g. hydrochloric acid and acetic acid), whereby the desired compound is obtained.

Subsequently, Compound (I-6) can be obtained according to the synthetic methods described above.

Process 7

Process for preparing Compound (I-7) which is Compound (I) wherein W is

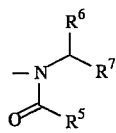

(wherein $R^5$, $R^6$ and $R^7$ have the same meanings as defined above).

Compound (I-7) can be prepared by the following reaction steps.

(Step 71)

Compound (XXXb) can be obtained by reacting Compound (XXXa) with a compound represented by the formula $H_2NR^6R^7$ (wherein $R^6$ and $R^7$ have the same meanings as defined above) in the presence of molecular sieves, and if necessary, in the presence of an acid such as p-toluenesulfonic acid in an inert solvent (e.g. THF and alcohol) at a temperature of room temperature to the boiling point of the solvent used for one hour to one week, and then treating the reaction mixture with an equivalent to a large excess of a reducing reagent such as sodium cyanoborohydride in the presence of an alcohol (e.g. methanol and ethanol) at a temperature of 0° C. to room temperature for one hour to 3 days.

(Step 72)

Compound (XXXc) can be obtained by reacting Compound (XXXb) with an acid halide (e.g. acetyl chloride and propionyl chloride) or an acid anhydride (e.g. acetic anhydride and propionic anhydride) in the presence of a base (e.g. pyridine, triethylamine and sodium hydride) in an inert solvent (e.g. dichloromethane, DMF, THF and toluene), or using the base per se as a solvent, at a temperature of 0° C. to the boiling point of the solvent used for 0.1 to 24 hours.

Subsequently, Compound (I-7) can be obtained according to the synthetic methods described above.

Process 8

Process for preparing Compound (I-8) which is Compound (I) wherein W is

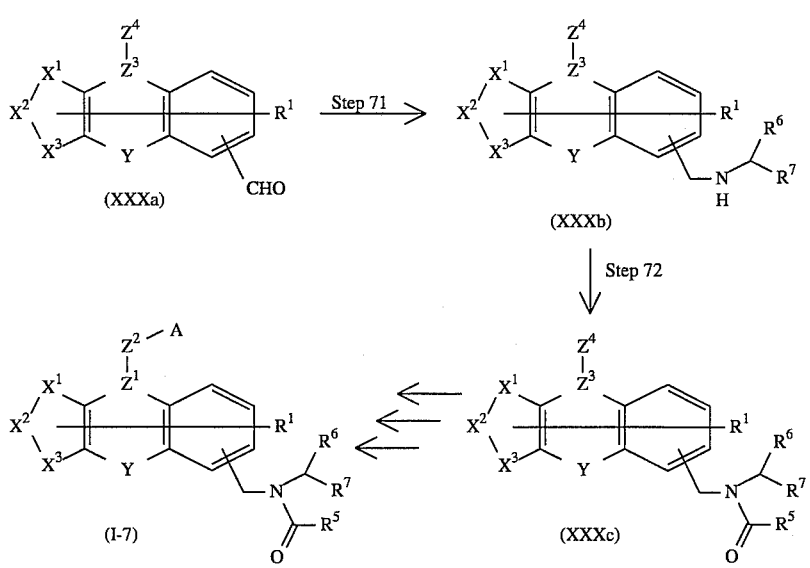

(In the formulae, $Z^3$—$Z^4$ represents $Z^1$—$Z^2$—A or its precursor; and $R^1$, $R^5$, $R^6$, $R^7$, A, $X^1$—$X^2$—$X^3$, Y and $Z^1$—$Z^2$ have the same meanings as defined above.)

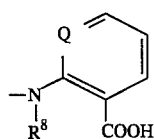

(wherein $R^8$ and Q have the same meanings as defined above)

Compound (I-8) can be prepared by the following reaction steps.

(wherein $R^8$, $R^9$ and Q have the same meanings as defined above) [J. Med. Chem., 35, 3714(1992)] in place of the compound represented by the formula H—W.

Subsequently, Compound (I-8) can be obtained according to the synthetic methods described above.

Alternatively, Compound (I-8) can be prepared by the following reaction steps.

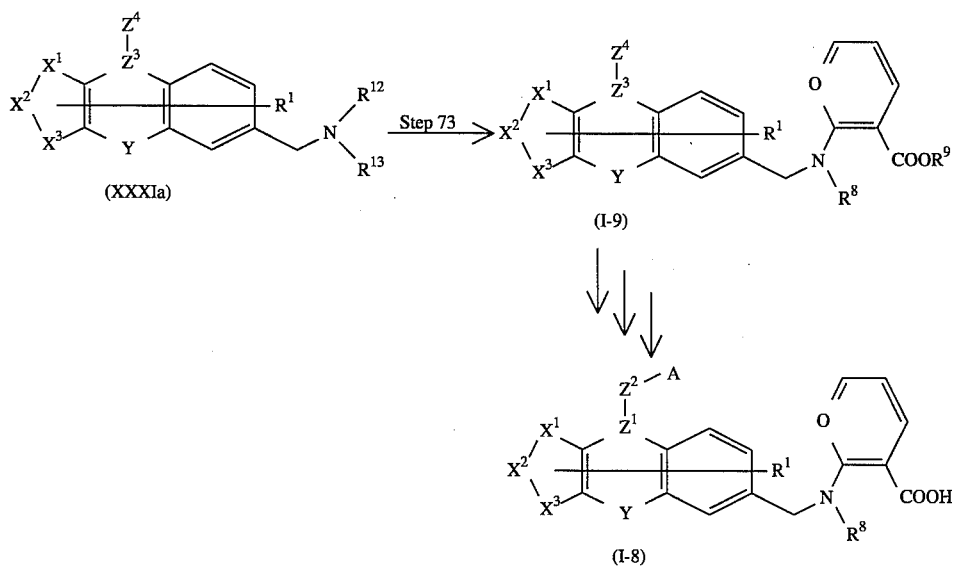

(In the formulae, $R^1$, $R^8$, $R^9$, $R^{12}$, $R^{13}$, Q, A, $X^1$—$X^2$—$X^3$, Y, $Z^1$—$Z^2$ and $Z^3$—$Z^4$ have same meanings as defined above.)

(Step 73)

Compound (I-9) can be obtained from Compound (XXXIa) according to the method of Step 45 using a compound represented by the formula

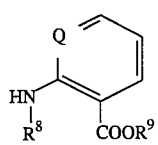

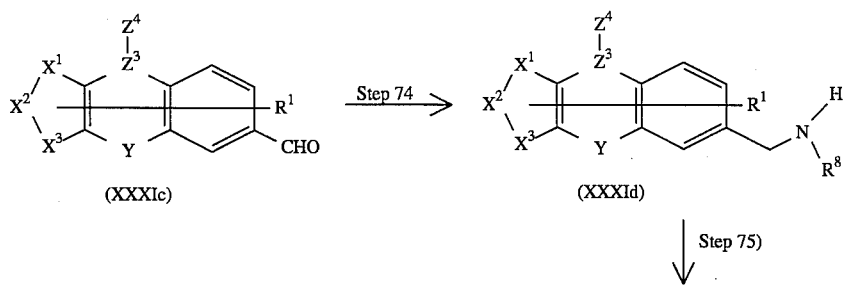

-continued

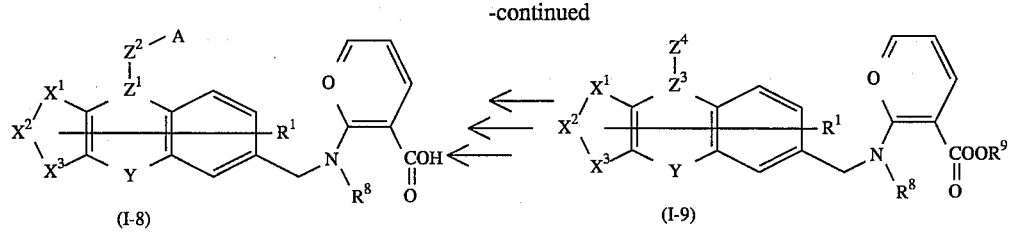

(In the formulae, $R^1$, $R^8$, $R^9$, Q, A, $X^1$—$X^2$—$X^3$, Y, $Z^1$—$Z^2$ and $Z^3$—$Z^4$ have the same meanings as defined above.)

(Step 74)

Compound (XXXId) can be obtained from Compound (XXXIc) according to the method of Step 71 using a compound represented by the formula $H_2NR^8$ (wherein $R^8$ has the same meaning as defined above) in place of the compound represented by the formula $H_2NR^6R^7$.

(Step 75)

Compound (I-9) can be obtained by reacting Compound (XXXId) with a compound represented by the formula

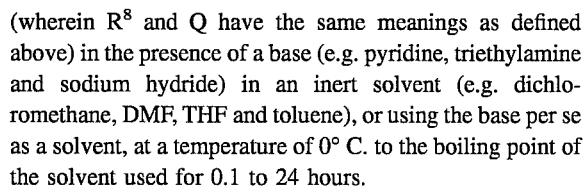

(wherein $R^8$ and Q have the same meanings as defined above) in the presence of a base (e.g. pyridine, triethylamine and sodium hydride) in an inert solvent (e.g. dichloromethane, DMF, THF and toluene), or using the base per se as a solvent, at a temperature of 0° C. to the boiling point of the solvent used for 0.1 to 24 hours.

Subsequently, Compound (I-8) can be obtained according to the synthetic methods described above.

In the above processes for producing Compounds (I), the order of the reaction steps may be varied.

In the case where a salt of Compound (I) is desired and it is produced in the form of the desired salt, it can be subjected to purification as such. In the case where Compound (I) is produced in the free state and its salt is desired, Compound (I) is treated with an acid or a base in an appropriate solvent, followed by isolation and purification.

The intermediates and the desired products in the processes described above can be isolated and purified by purification means conventionally used in organic synthetic chemistry, for example, filtration, extraction, washing, drying, concentration, recrystallization and various kinds of chromatography. The intermediates can be subjected to the subsequent reaction without particular purification.

There may be stereoisomers such as geometrical isomers and optical isomers for Compounds (I) and the present invention covers all possible isomers including the above-mentioned ones.

Compounds (I) and pharmaceutically acceptable salts thereof may be in the form of adducts with water or various solvents, which are also within the scope of the present invention.

Representative examples of Compounds (I) obtained by the present invention are shown in Table 1.

TABLE 1

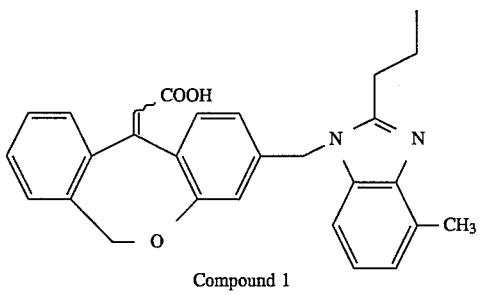

Compound 1

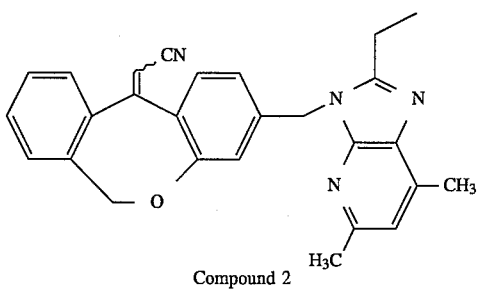

Compound 2

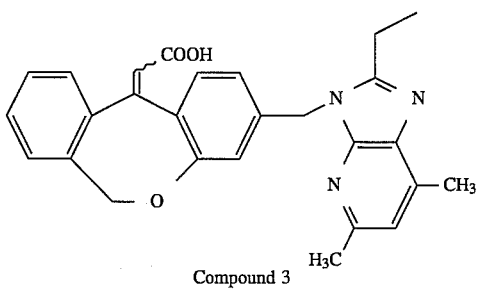

Compound 3

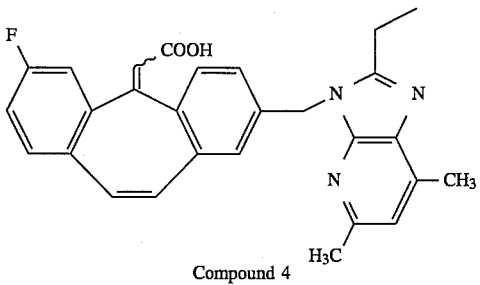

Compound 4

TABLE 1-continued
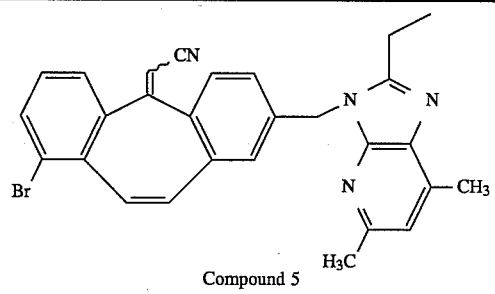
Compound 5
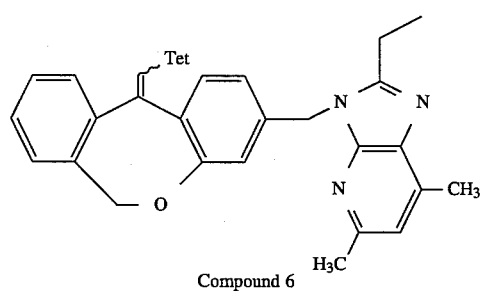
Compound 6
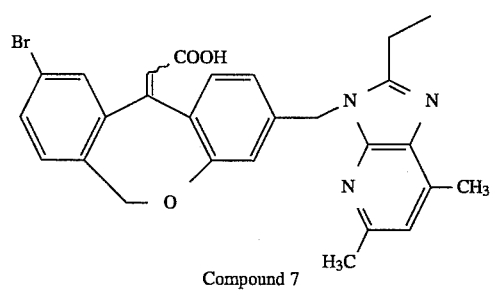
Compound 7
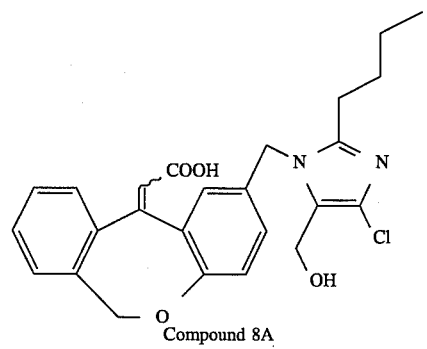
Compound 8A
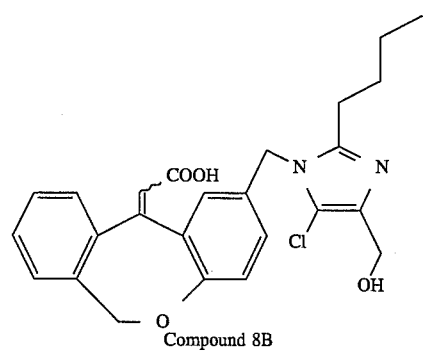
Compound 8B
TABLE 1-continued
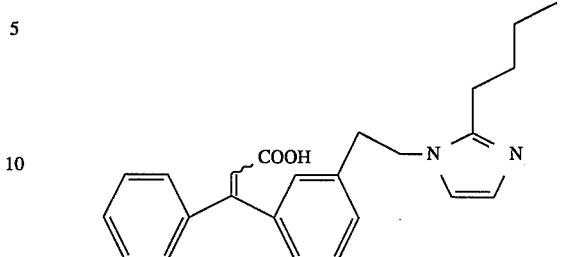
Compound 9
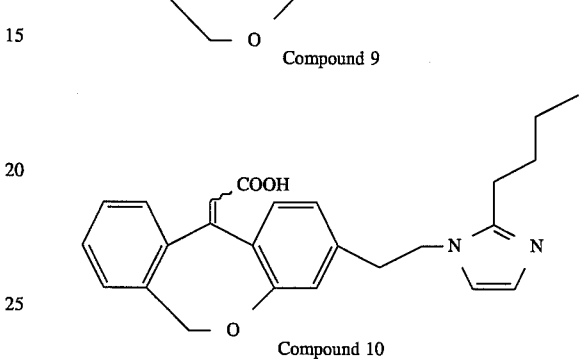
Compound 10
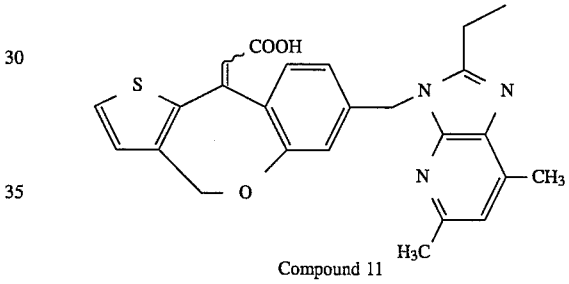
Compound 11
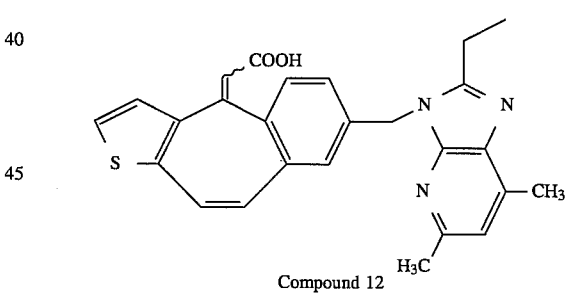
Compound 12
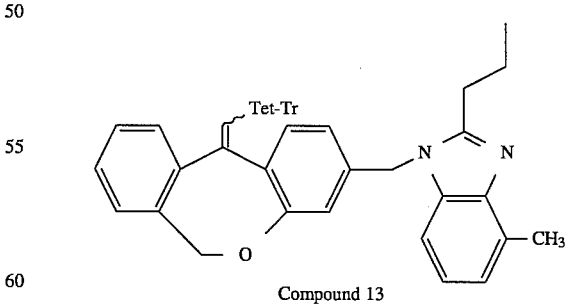
Compound 13

TABLE 1-continued
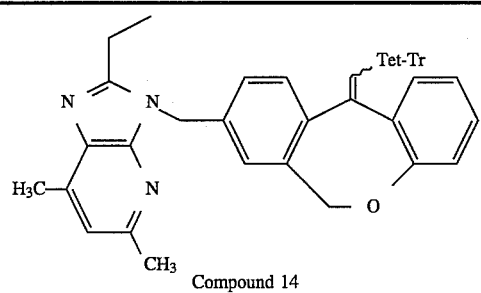
Compound 14
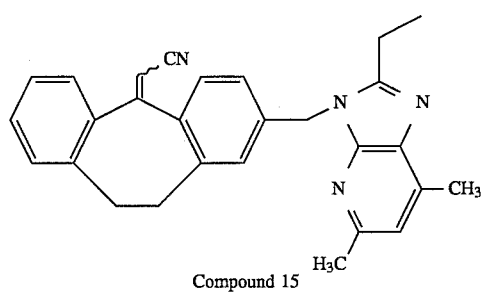
Compound 15
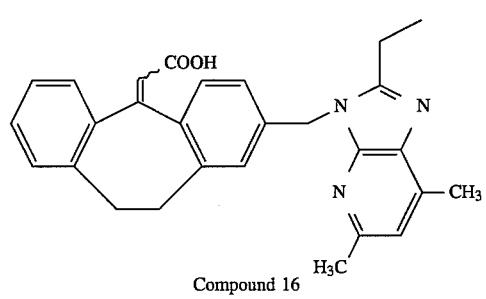
Compound 16
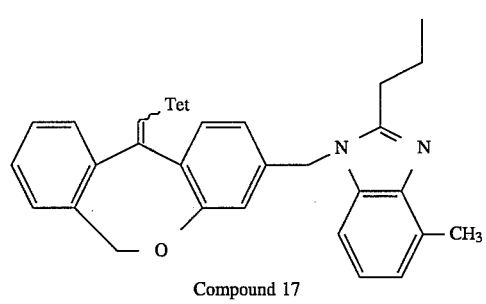
Compound 17
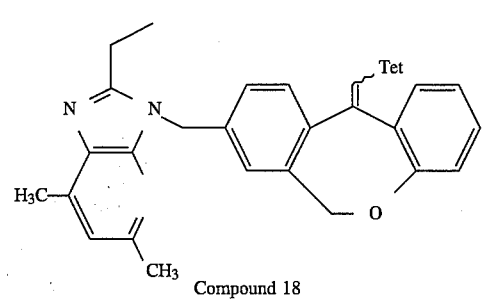
Compound 18
TABLE 1-continued
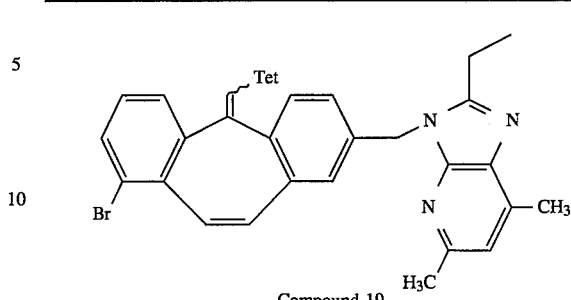
Compound 19
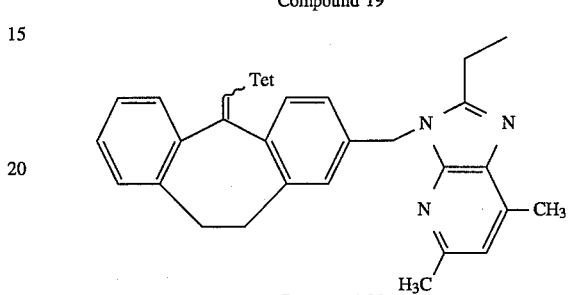
Compound 20
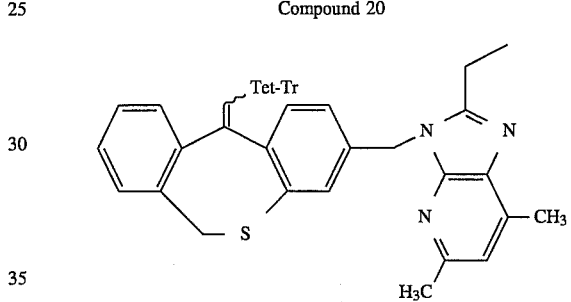
Compound 21
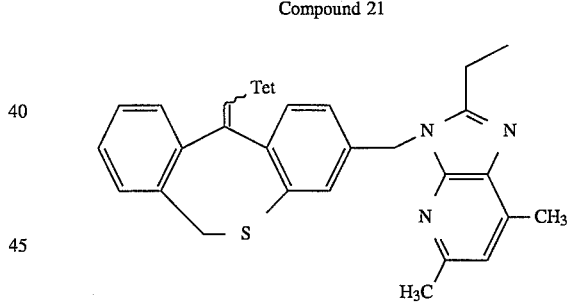
Compound 22
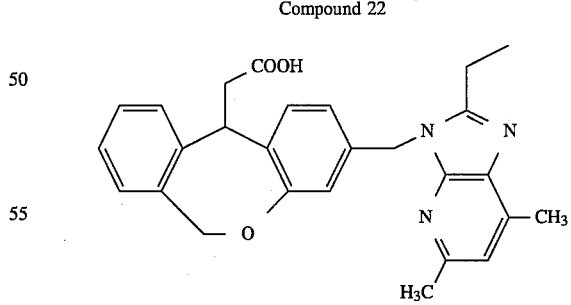

TABLE 1-continued
Compound 23
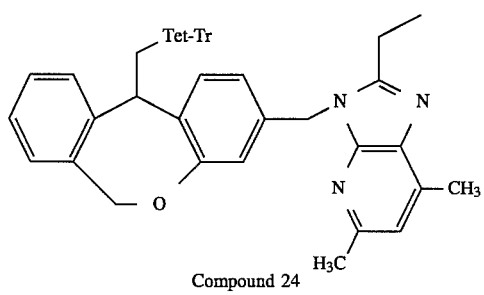
Compound 24
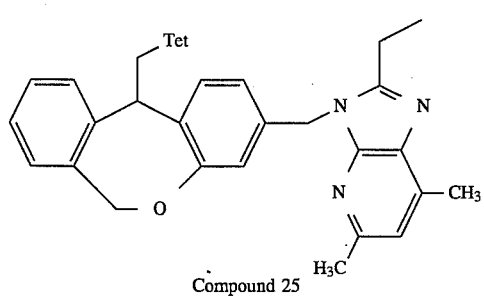
Compound 25
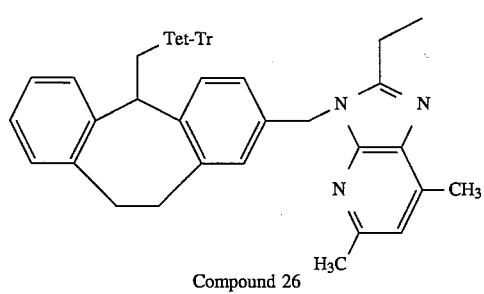
Compound 26
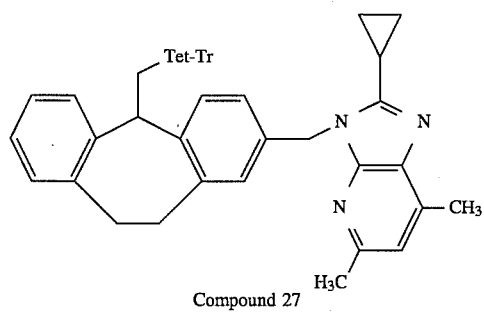
Compound 27
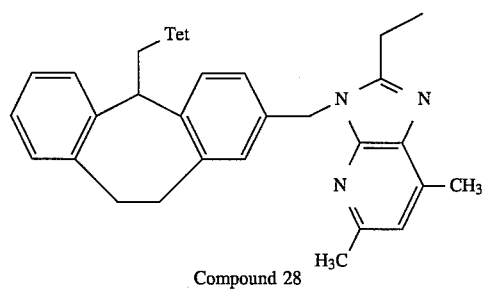
Compound 28
TABLE 1-continued
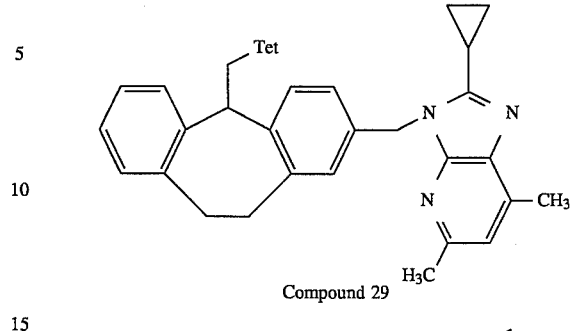
Compound 29
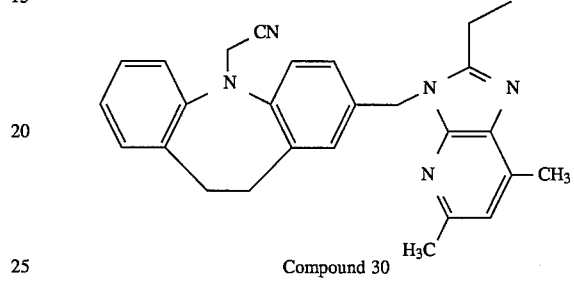
Compound 30
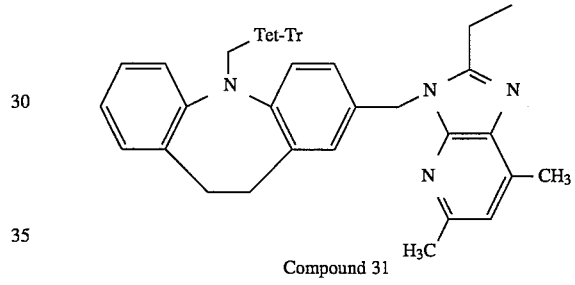
Compound 31
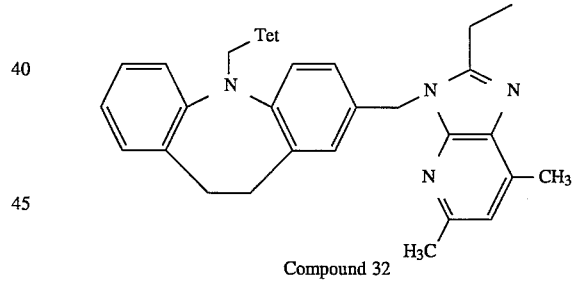
Compound 32
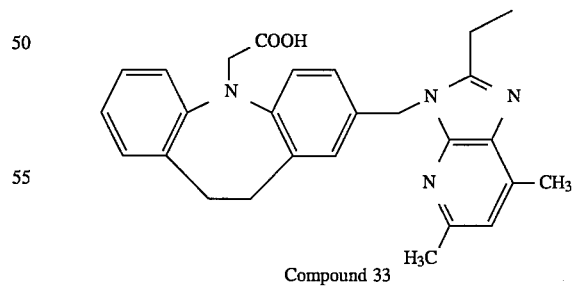
Compound 33

TABLE 1-continued
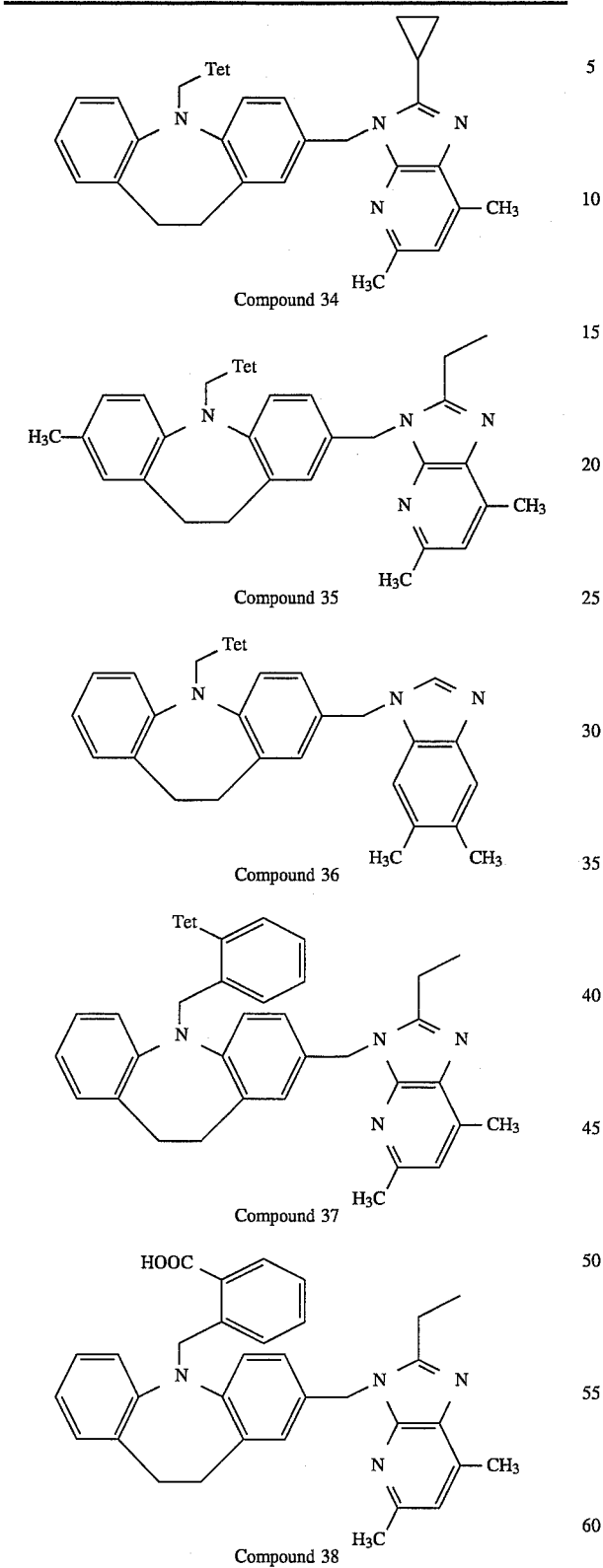
Compound 34
Compound 35
Compound 36
Compound 37
Compound 38
TABLE 1-continued
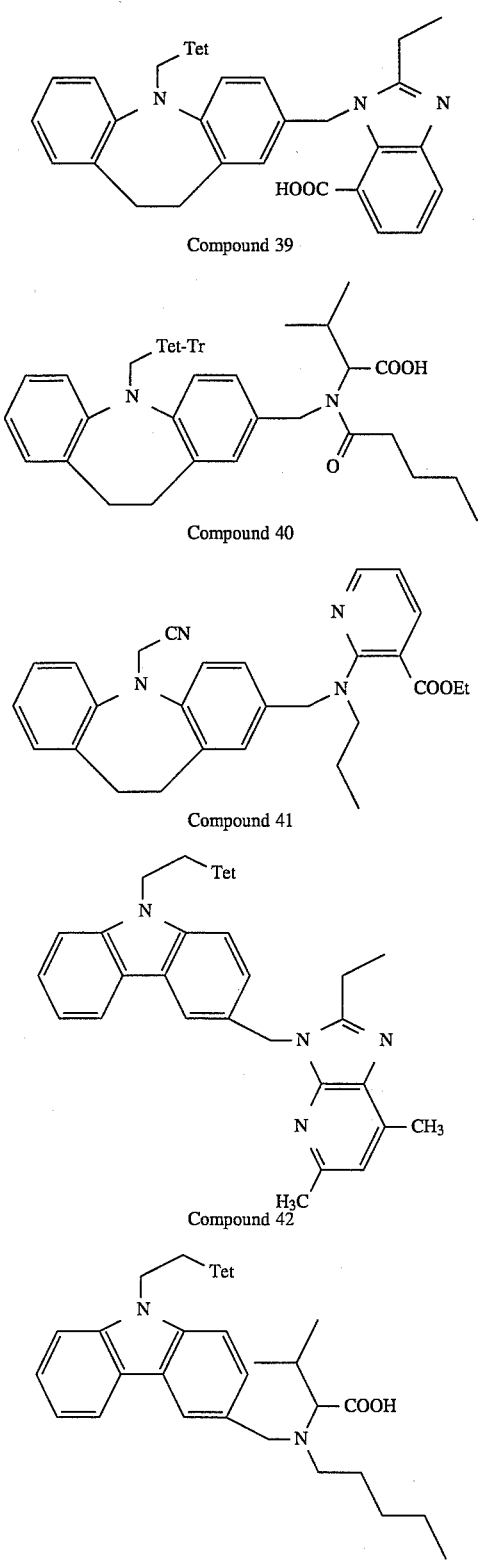
Compound 39
Compound 40
Compound 41
Compound 42

TABLE 1-continued

Compound 43

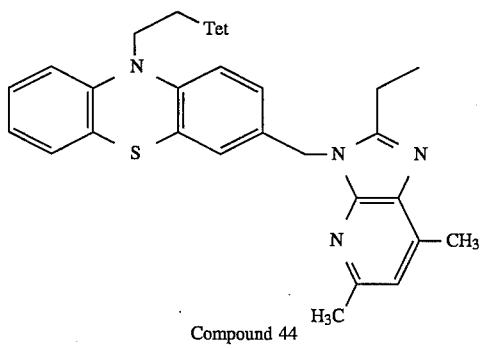

Compound 44

Tet represents tetrazolyl and Tr represents trityl.

The pharmacological activities of representative Compounds (I) are shown below by experimental examples.

EXPERIMENTAL EXAMPLE 1

Receptor binding test using bovine adrenal cortex

Tissue of bovine adrenal cortex was finely cut and suspended in a 0.25M sucrose solution containing NaHCO$_3$, ethylenediaminetetraacetic acid (EDTA), leupepsin, pepstatin A and phenylmethanesulfonyl fluoride, followed by homogenization. The homogenate was centrifuged at 3,000 rpm for 10 minutes and the supernatant was centrifuged at 9,000 rpm. Then, the supernatant was further centrifuged at 30,000 rpm for 60 minutes and the precipitate was suspended in NaHCO$_3$-EDTA solution, followed by centrifugation at 30,000 rpm for 60 minutes. The resulting precipitate was suspended in a phosphate buffer and the suspension was used for the binding test as an AII receptor source.

To a test compound or a solvent were added 250 µl of the AII receptor solution prepared above, 250 µl of Tris 50 mM buffer containing 0.2% bovine serum albumin (BSA), and 20 µl of [$^{125}$I]AII ($2.5 \times 10^{-10}$M). The mixture was allowed to stand at room temperature for 2 hours and then filtered through a glass fiber filter (GF/B Wattman). The filter was placed in a test tube and the radioactivity was measured using a gamma-counter.

The inhibitory activity (inhibition rate) of the test compound (0.1 µM) against the receptor binding of [$^{125}$I]AII was calculated by the following equation.

$$\text{Inhibition Rate (\%)} = \left\{ 1 - \frac{\left(\begin{array}{c}\text{Binding Amount in}\\ \text{the Presence of}\\ \text{a Test Compound}\end{array}\right) - \left(\begin{array}{c}\text{Nonspecific}\\ \text{Binding}\\ \text{amount}\end{array}\right)}{\left(\begin{array}{c}\text{Total Binding}\\ \text{Amount}\end{array}\right) - \left(\begin{array}{c}\text{Nonspecific}\\ \text{Binding Amount}\end{array}\right)} \right\} \times 100$$

The binding amount in the presence of a test compound is the amount of radioactivity of [$^{125}$I]AII bound in the presence of a test compound (0.1 µM).

The total binding amount is the amount of radioactivity of [$^{125}$I]AII bound in the absence of a test compound.

The nonspecific binding amount is the amount of radioactivity of [$^{125}$I]AII bound in the presence of 1 µM AII.

The results are shown in Table 2.

TABLE 2

| Compound Number | Inhibition Rate |
|---|---|
| 1* | 43 |
| 3* | 78 |
| 4* | 77 |
| 6-E | 87 |
| 6-Z* | 66 |
| 7* | 52 |
| 11 | 84 |
| 12 | 72 |
| 16 | 91 |
| 18-Z | 81 |
| 19* | 14 |
| 20A* | 70 |
| 20B* | 88 |
| 22-E* | 80 |
| 23 | 61 |
| 25* | 94 |
| 28* | 83 |
| 29* | 92 |
| 32 | 86 |
| 33* | 88 |
| 34* | 97 |
| 38* | 68 |
| 40* | 95 |
| 42* | 85 |

In the column of Compound Number in the table, E means the E form, Z means the Z form, A and B mean that they are geometrical isomers with respect to the stereochemistry of the double bond, and * means an adduct with a salt and/or a solvent. These symbols have the same meanings in the following description.

EXPERIMENTAL EXAMPLE 2

Inhibition test against hypertensive response to AII

Male Wistar rats were anesthetized with pentobarbital. A cannula for blood pressure measurement was inserted from the right femoral artery into the abdominal aorta and another cannula for AII injection was inserted into the right femoral vein. The cannulae were passed under skin and fixed after coming out of the back, and the blood pressure was recorded on a polygraph from the artery cannula using a voltage transformer.

On the day after operation, 0.3 µg/kg AII was intravenously injected into each animal and the change in the average artery blood pressure was examined as the control pressor response. Then, a test compound (1 mg/kg) was orally administered and after one hour, 0.3 µg/kg AII was injected again, followed by examination of the pressor response. The inhibitory effect of the test compound against the control pressor response was determined as the inhibition rate. Compound 32 exhibited the inhibition rate of 45%.

Though Compounds (I) and pharmaceutically acceptable salts thereof may be administered as they are, it is usually desirable to provide them in the form of various pharmaceutical preparations. Such pharmaceutical preparations can be used for both human beings and animals.

The pharmaceutical preparations in accordance with the present invention may contain Compound (I) or a pharmaceutically acceptable salt thereof, as an active ingredient, either solely or as a mixture with other therapeutically effective components. The pharmaceutical preparations may be prepared by any means which are well known in the technical field of pharmaceutics after mixing the active ingredient with one or more pharmaceutically acceptable carriers.

It is desired to use the administration route which is the most effective in therapy such as oral route or parenteral route (e.g. intrarectal, intrabuccal, subcutaneous, intramuscular and intravenous administrations).

Examples of dosage forms are capsules, tablets, granules, syrups, emulsions, suppositories and injections.

Liquid preparations suitable for oral administration such as emulsions and syrups can be prepared using water, sugars (e.g. sucrose, sorbitol and fructose), glycols (e.g. polyethyleneglycol and propyleneglycol), oils (e.g. sesame oil, olive oil and soybean oil), preservatives (e.g. p-hydroxybenzoates), flavors (e.g. strawberry flavor and peppermint), and the like. Capsules, tablets, powders, granules, etc. can be prepared using excipients (e.g. lactose, glucose, sucrose and mannitol), disintegrators (e.g. starch and sodium alginate), lubricants (e.g. magnesium stearate and talc), binders (e.g. polyvinyl alcohol, hydroxypropylcellulose and gelatin), surfactants (e.g. fatty acid esters), plasticizers (e.g. glycerin), and the like.

Preparations suitable for parenteral administration comprise sterilized aqueous preparations of the active compound which are preferably isotonic to the blood of the patient. For example, a solution for injection is prepared using a carrier such as a salt solution, a glucose solution or a mixture of a salt solution and a glucose solution. Preparations for intrarectal administration are prepared using a carrier such as cacao fat, hydrogenated fat or a hydrogenated carboxylic acid and are provided as suppositories.

These parenteral preparations may also contain one or more auxiliary components selected from the above-mentioned diluents, flavors, preservatives, excipients, disintegrators, lubricants, binders, surfactants and plasticizers.

The effective dose and the administration schedule of Compounds (I) or pharmaceutically acceptable salts thereof may vary depending upon the administration route, age and body weight of a patient and the type or degree of the disease to be treated, but usually, in the case of oral administration, the effective compound is administered in a dose of 0.01 mg to 1 g/person/day at one time or in several parts. In the case of parenteral administration such as intravenous injection, the effective compound is administered in a dose of 0.001 mg to 100 mg/person/day at one time or in several parts. It should, however, be noted that the dose may vary depending upon various conditions as given above.

Certain embodiments of the invention are illustrated in the following examples.

EXAMPLE 1

[3-(4-Methyl-2-propyl-1H-benzimidazol-1-yl)methyl-6,11-dihydrodibenz[b,e]oxepin-11-yliden]acetic acid (Compound 1)

(Step A)
Ethyl (3-carboxy-6,11-dihydrodibenz[b,e]oxepin-11-yliden)acetate (Compound 1-a)

A solution of LDA in THF was prepared by adding 11.9 ml of diisopropylamine and 49 ml of n-butyl lithium (1.65M hexane solution) to 300 ml of THF. To this solution was added 14 ml of ethyl (trimethylsilyl)acetate at −78° C. and the mixture was stirred for one hour. Under the same conditions, 300 ml of a solution of 6.5 g of 11-oxo-6,11-dihydrodibenz[b,e]oxepin-3-carboxylic acid in THF was added dropwise thereto. Then, the mixture was gradually brought to room temperature and was stirred for 3 hours, followed by addition of ice chips. After being adjusted to pH 5 with 4N aqueous hydrochloric acid, the mixture was extracted with ethyl acetate, and the organic layer was washed with a saturated aqueous solution of sodium chloride and dried over anhydrous magnesium sulfate. The solvent was distilled off under reduced pressure, and the residue was purified by silica gel column chromatography [eluent: chloroform/methanol (20/1)] to give 7.63 g (92%) of the product as a colorless oily substance.

NMR (CDCl$_3$; δ, ppm): 1.13(t, J=7.0 Hz, 2.1H; E form), 1.18 (t, J=7.0 Hz, 0.9H; Z form), 4.10(q, J=7.0 Hz, 1.4H; E form), 4.17(q, J=7.0 Hz, 0.6H; Z form), 5.26(bs, 2H), 6.10(s, 0.3H; Z form), 6.39(s, 0.7H; E form), 7.1–7.7(m, 7H)

(Step B)
Ethyl (3-hydroxymethyl-6,11-dihydrodibenz[b,e]oxepin-11-yliden) acetate (Compound 1-b)

Sodium borohydride (2.22 g) was dissolved in 300 ml of THF, and 7.45 g of iodine was added to the solution under ice cooling. Then, 300 ml of a solution of 7.63 g of Compound 1-a in THF was added under the same conditions and the mixture was stirred at room temperature overnight, followed by addition of ice chips. The mixture was then diluted with ethyl acetate, and the organic layer was washed with a saturated aqueous solution of sodium chloride and dried over anhydrous magnesium sulfate. The solvent was distilled off under reduced pressure, and the residue was purified by silica gel column chromatography [eluent: chloroform] to give 6.58 g (90.2%) of the product as a colorless oily substance.

NMR (CDCl$_3$; δ, ppm): 1.22(t, J=7.1 Hz, 3H), 4.05(q, J=7.1 Hz, 2H), 4.54(s, 2H), 5.17(bs, 2H), 6.00(s, 0.3H; Z form), 6.32(s, 0.7H; E form), 6.65–6.95(m, 2H), 7.1–7.45(m, 5H)

(Step C)
Ethyl (3-chloromethyl-6,11-dihydrodibenz[b,e]oxepin-11-yliden)acetate (Compound 1-c)

Compound 1-b (6.58 g) was dissolved in 200 ml of dichloromethane, and 6.2 ml of thionyl chloride and 6.9 ml of pyridine were added to the solution. The mixture was stirred at room temperature for 3 hours and then concentrated under reduced pressure. The obtained product was unstable and immediately subjected to the subsequent reaction without purification.

NMR (CDCl$_3$; δ, ppm): 1.12(t, J=7.0 Hz, 3H), 4.01(q, J=7.0 Hz, 2H), 4.41(s, 2H), 5.15(bs, 2H), 5.95(s, 0.3H; Z form), 6.26(s, 0.7H; E form), 6.7–7.0(m, 2H), 7.1–7.4(m, 5H)

(Step D)
Ethyl [3-(4-methyl-2-propyl-1H-benzimidazol-1-yl)methyl-6,11-dihydrodibenz[b,e]oxepin-11-yliden]acetate (Compound 1-d)

4-Methyl-2-propyl-1H-benzimidazole (464 mg) was dissolved in a mixture of 50 ml of DMF and 80 ml of toluene, and 106.4 mg of sodium hydride (60% oily) was added to the solution under ice cooling, followed by stirring for 30 minutes. To the mixture was added 732 mg of Compound 1-c, and the mixture was heated under reflux for 3 hours. After the solvent was distilled off under reduced pressure, the residue was diluted with ethyl acetate. The organic layer was washed with a saturated aqueous solution of sodium chloride and dried over anhydrous magnesium sulfate. The solvent was distilled off under reduced pressure, and the residue was purified by silica gel column chromatography [eluent: hexane/ethyl acetate/triethylamine (20/5/1)] to give 629 mg (61%) of the product.

NMR (CDCl$_3$; δ, ppm): 0.99(t, J=7.4 Hz, 3H), 1.12(t, J=7.1 Hz, 2.1H; E form), 1.18(t, J=7.1 Hz, 0.9H; Z form), 1.37–1.86(m, 2H), 2.67(s, 3H), 2.81(t, J=7.9 Hz, 2H), 4.05(q, J=7.1 Hz, 1.4H; E form), 4.14(q, J=7.1 Hz, 0.6H; Z form), 5.16(bs, 2H), 5.21(s, 2H), 6.00(s, 0.3H; Z form), 6.29(s, 0.7H; E form), 6.48(s, 1H), 6.53–6.56(m, 1H), 6.94–7.09(m, 3H), 7.16–7.37(m, 5H)

(Step E)
Compound 1(0.4 hydrate)

A mixture of 628 mg of Compound 1-d, 224 mg of sodium hydroxide, 30 ml of methanol and 10 ml of water was heated under reflux for 3 hours. After cooling, the mixture was diluted with water, and adjusted to pH 5 with 4N aqueous hydrochloric acid. The resulting precipitate was separated from the mixture by filtration and washed with water to give 504 mg (85%) of the product.

The product was a 5:2 mixture of geometrical isomers with respect to the stereochemistry of the double bond.

Melting point: 272° C. (decomposition) NMR (DMSO-$d_6$; δ, ppm): 0.94(t, J=7.4 Hz, 3H), 1.67–1.80(m, 2H), 2.51(s, 3H), 2.76(t, J=7.4 Hz, 2H), 5.14(bs, 2H), 5.38(s, 2H), 5.96(s, 0.3H; Z form), 6.29(s, 0.7H; E form), 6.40(s, 1H), 6.55–6.62(m, 1H), 6.93–7.04(m, 2H), 7.14–7.44(m, 6H), 12.39(bs, 1H) IR(KBr; cm$^1$): 2964, 1704, 1611, 1456, 1421, 1183, 1031, 752 Elemental analysis (%): $C_{28}H_{26}N_2O_3 \cdot 0.4H_2O$ Found: C 75.47, H 6.12, N 6.15 Calcd.: C 75.45, H 6.06, N 6.28

EXAMPLE 2

[3-(5,7-Dimethyl-2-ethyl-3H-imidazo[4,5-b]pyridin-3-yl)methyl-6,11-dihydrodibenz[b,e]oxepin-11-yliden]-acetonitrile (Compound 2)

(Step A)
(3-Ethoxycarbonyl-6,11-dihydrodibenz[b,e]oxepin-11-yliden)acetonitrile (Compound 2-a)

Diethyl (cyanomethyl)phosphonate (52 ml) was dissolved in 200 ml of THF, and 12.8 g of sodium hydride (60% oily) was added to the solution under ice cooling, followed by stirring for one hour. To the mixture was added 200 ml of a solution of 17.3 g of ethyl 11-oxo-6,11-dihydrodibenz[b,e]oxepin-3-carboxylate in THF, and the mixture was heated under reflux for 3 hours. After cooling, ice chips were added to the reaction mixture, and the mixture was then diluted with ethyl acetate. The organic layer was washed with a saturated aqueous solution of sodium chloride and dried over anhydrous magnesium sulfate. After the solvent was distilled off under reduced pressure, the residue was purified by silica gel column chromatography [eluent: hexane/ethyl acetate (2/1)] to give 11.5 g (58%) of the product as a colorless oily substance.

NMR (CDCl$_3$; δ, ppm): 1.34(t, J=7.1 Hz, 3H), 4.33(q, J=7.1 Hz, 2H), 5.17(s, 2H), 5.54(s, 0.33H; Z form), 5.88(s, 0.67H; E form), 7.2–7.8(m, 7H)

(Step B)
(3-Hydroxymethyl-6,11-dihydrodibenz[b,e]oxepin-11-yliden)acetonitrile (Compound 2-b)

Compound 2-a (7.78 g) was dissolved in 500 ml of THF, and 2.75 g of lithium borohydride was added in small portions to the solution under ice cooling. The mixture was stirred at room temperature for 2 days, followed by further addition of 2.84 g of lithium borohydride. The mixture was stirred at room temperature for 4 days, and ice chips were added thereto. The reaction mixture was diluted with ethyl acetate and then adjusted to pH 5.5 with 4N aqueous hydrochloric acid. The organic layer was washed with a saturated aqueous solution of sodium chloride and dried over anhydrous magnesium sulfate. The solvent was distilled off under reduced pressure, and the resulting crude crystals were recrystallized from isopropanol to give 4.26 g (63%) of the product.

Melting point: 169.5°–171° C. (isopropanol) NMR (DMSO-$d_6$; δ, ppm): 4.47(s, 0.5H; Z form), 4.53(s, 1.5H; E form), 5.15(s, 2H), 5.59(s, 0.25H; Z form), 5.99(s, 0.75H; E form), 6.8–7.0(m, 2H), 7.2–7.8(m, 5H)

(Step C)
(3-Chloromethyl-6,11-dihydrodibenz[b,e]oxepin-11-yliden)acetonitrile (Compound 2-c)

The desired compound (2.3 g, 90%) was obtained from 2.4 g of Compound 2-b according to the same procedure as in Step C of Example 1.

NMR (CDCl$_3$; δ, ppm): 4.47(s, 2H), 5.13(s, 2H), 5.45(s, 0.25H; Z form), 5.80(s, 0.75H; E form), 6.8–7.1(m, 2H), 7.2–7.7(m, 5H)

(Step D)
Compound 2

The same procedure as in Step D of Example 1 was repeated using 2.17 g of Compound 2-c and 1.38 g of 5,7-dimethyl-2-ethyl-3H-imidazo[4,5-b]pyridine, and recrystallization from isopropanol gave 2.25 g (70%) of the product as a white solid.

Melting point: 177°–179.5° C.

NMR (CDCl$_3$; δ, ppm): 1.31(t, J=7.4 Hz, 3H), 2.56(s, 3H), 2.62(s, 3H), 2.75(q, J=7.4 Hz, 2H), 5.10(s, 2H), 5.37(s, 2H), 5.81(s, 1H), 6.57(d, J=1.5 Hz, 1H), 6.70(dd, J=8.4 Hz, 1.5 Hz, 1H), 6.88(s, 1H), 7.23(d, J=8.4 Hz, 1H), 7.35–7.48(m, 3H), 7.52–7.57(m, 1H) Elemental analysis (%): $C_{27}H_{24}N_4O$ Found: C 76.82, H 5.97, N 12.88 Calcd.: C 77.12, H 5.75, N 13.32

EXAMPLE 3

[3-(5,7-Dimethyl-2-ethyl-3H-imidazo[4,5-b]pyridin-3-yl)methyl-6,11-dihydrodibenz[b,e]oxepin-11-yliden]acetic acid [Compound 3(0.5 hydrate)]

A mixture of 88 mg of Compound 2, 2 ml of a 1N aqueous solution of sodium hydroxide and 5 ml of ethyleneglycol was heated under reflux for 48 hours. After cooling, the mixture was diluted with water and washed with ether, and the aqueous layer was adjusted to pH 4 with 4N aqueous hydrochloric acid. The resulting precipitate was separated from the mixture by filtration and washed with water to give 44.7 mg (49%) of the product as a white solid.

The product was a 2:1 mixture of geometrical isomers with respect to the stereochemistry of the double bond.

Melting point: 145°–148° C. NMR (DMSO-$d_6$; δ, ppm): 1.23(t, J=7.4 Hz, 3H), 2.48(s, 3H), 2.51(s, 3H), 2.73(q, J=7.4 Hz, 2H), 5.15(bs, 2H), 5.37(s, 2H), 5.97(s, 0.33H; Z form), 6.29(s, 0.67H; E form), 6.45(s, 1H), 6.60–6.68(m, 1H), 6.93(s, 1H), 7.14–7.45(m, 5H)

IR(KBr; cm$^{-1}$): 2932, 2884, 1726, 1633, 1480, 1437, 1404, 1306, 1270, 1054, 765 Elemental analysis (%): $C_{28}H_{26}N_2O_3 \cdot 0.5H_2O$ Found: C 72.16, H 5.83, N 9.32 Calcd.: C 72.30, H 5.84, N 9.37

EXAMPLE 4

[2-(5,7-Dimethyl-2-ethyl-3H-imidazo[4,5-b]pyridin-3-yl)methyl-7-fluoro-5H-dibenzo[a,d]cyclohepten-5-yliden]acetic acid (Compound 4)

(Step A)
Ethyl (7-fluoro-2-methyl-5H-dibenzo[a,d]cyclohepten-5-yliden)acetate (Compound 4-a)

Ethyl diethylphosphonoacetate (1.3 ml) was dissolved in 30 ml of THF, and 0.26 g of sodium hydride (60% oily) was added to the solution under ice cooling, followed by stirring under the same conditions for 30 minutes. To the mixture was added dropwise 20 ml of a solution of 0.3 g of 7-fluoro-2-methyl-5-oxo-5H-dibenzo[a,d]cycloheptene in THF, and the mixture was heated under reflux for 2 hours. After cooling, water and ethyl acetate were added to the mixture, and the organic layer was washed with a saturated aqueous solution of sodium chloride and dried over anhydrous magnesium sulfate. The solvent was distilled off under reduced pressure, and the residue was purified by silica gel column chromatography [eluent: hexane/ethyl acetate (10/1)] to give 0.38 g (98%) of the product as a yellow oily substance.

NMR (CDCl$_3$; δ, ppm): 1.10(t, J=7.0 Hz, 3H), 2.35(s, 3H), 4.03(q, J=7.0 Hz, 2H), 5.88 and 5.90(s for each, total 1H), 6.8–7.5(m, 8H)

(Step B)

Ethyl (2-bromomethyl-7-fluoro-5H-dibenzo[a,d]cyclohepten-5-yliden)acetate (Compound 4-b)

Compound 4-a (0.24 g) was dissolved in 20 ml of carbon tetrachloride, and 0.14 g of NBS and catalytic amount of benzoyl peroxide were added to the solution, followed by heating under reflux for 4 hours. After cooling, insoluble matters were filtered off and the filtrate was diluted with dichloromethane. The dilution of the filtrate was washed with a saturated aqueous solution of sodium chloride and dried over anhydrous magnesium sulfate, and the solvent was distilled off under reduced pressure. The obtained product was unstable and subjected to the subsequent reaction without particular purification.

NMR (CDCl$_3$; δ, ppm): 1.10(t, J=7.0 Hz, 3H), 4.02(q, J=7.0 Hz, 2H), 4.48(s, 2H), 5.90 and 5.93(s for each, total 1H), 6.7–8.1(m, 8H)

(Step C)

Ethyl [2-(5,7-dimethyl-2-ethyl-3H-imidazo[4,5-b]pyridin-3-yl)methyl-7-fluoro-5H-dibenzo[a,d]cyclohepten-5-yliden]acetate (Compound 4-c)

The same procedure as in Step D of Example 1 was repeated using 0.34 g of Compound 4-b and 5,7-dimethyl-2-ethyl-3H-imidazo[4,5-b]pyridine to give 60 mg (14%) of the product.

NMR (CDCl$_3$; δ, ppm): 1.05 and 1.09(t for each, J=7.0 Hz, total 6H), 1.32(t, J=7.4 Hz, 3H), 2.57(s, 3H), 2.63(s, 3H), 2.77(q, J=7.4 Hz, 2H), 3.96 and 4.03 (q for each, J=7.0 Hz, total 4H), 5.46(s, 2H), 5.85 and 5.90(s for each, total 1H), 6.7–7.4(m, 9H)

(Step D)

Compound 4(0.8 hydrate)

Compound 4-c (50 mg) was hydrolyzed according to the same procedure as in Step E of Example 1 to give 19.8 mg (42%) of the product as a white solid.

Melting point: 144°–145° C. (decomposition) MS: 453 (M$^+$) Elemental analysis (%): C$_{28}$H$_{24}$FN$_3$O$_2$·0.8H$_2$O Found: C 71.62, H 5.34, N 9.12 Calcd.: C 71.87, H 5.51, N 8.98

EXAMPLE 5

[1-Bromo-8-(5,7-dimethyl-2-ethyl-3H-imidazo[4,5-b]-pyridin-3-yl)methyl-5H-dibenzo[a,d]cyclohepten-5-yliden]acetonitrile (Compound 5)

(Step A)

(1-Bromo-8-methyl-5H-dibenzo[a,d]cyclohepten-5-yl)acetonitrile (Compound 5-a)

The same procedure as in Step A of Example 2 was repeated using 0.86 g of 1-bromo-8-methyl-5-oxo-5H-dibenzo[a,d]cycloheptene and 1.4 ml of diethyl (cyanomethyl)phosphonate to give 0.64 g (69%) of the product as an oily substance.

MS: 321 (M$^+$), 323 (M$^+$+2) NMR (CDCl$_3$; δ, ppm): 2.38(s, 3H), 5.41(s, 1H), 6.8–7.7(m, 8H)

(Step B)

Compound 5

The same procedures as in Steps B and C of Example 4 were repeated using 0.64 g of Compound 5-a to give 0.51 g (52%) of the product as an oily substance.

MS: 494 (M$^+$), 496 (M$^+$+2) NMR (CDCl$_3$; δ, ppm): 1.33(t, J=7.4 Hz, 3H), 2.58(s, 3H), 2.65(s, 3H), 2.80(q, J=7.4 Hz, 2H), 5.44(s, 1H), 5.50(s, 2H), 6.8–7.7(m, 9H)

EXAMPLE 6

3-(5,7-Dimethyl-2-ethyl-3H-imidazo[4,5-b]pyridin-3-yl)methyl-11-(1H-tetrazol-5-yl)methylene-6,11-dihydrodibenz[b,e]oxepin (Compound 6)

(Step A)

3-(5,7-Dimethyl-2-ethyl-3H-imidazo[4,5-b]pyridin-3-yl)methyl-11-(N-triphenylmethyltetrazol-5-yl)methylene-6,11-dihydrodibenz[b,e]oxepin (Compound 6-a)

A mixture of 753 mg of Compound 2,582 mg of sodium azide, 480 mg of ammonium chloride and 50 ml of DMF was stirred overnight at 110° C. Then, 1.76 g of sodium azide and 1.44 g of ammonium chloride were added thereto and the mixture was stirred under the same conditions for six days. After insoluble matters were filtered off, the filtrate was concentrated under reduced pressure, followed by addition of a 1N aqueous solution of sodium hydroxide and ethyl acetate. The aqueous layer was adjusted to pH 5 with 4N aqueous hydrochloric acid, and the resulting precipitate (350 mg) was separated from the mixture by filtration.

The obtained crude product (296 mg) was then dissolved in a mixture of 12 ml of DMF and 0.11 ml of triethylamine, and 216 mg of trityl chloride was added to the solution, followed by stirring at room temperature for three hours. The solvent was distilled off under reduced pressure and the residue was diluted with ethyl acetate. The organic layer was washed with a saturated aqueous solution of sodium chloride and dried over anhydrous magnesium sulfate. After the solvent was distilled off under reduced pressure, the resulting residue was purified by repeating preparative thin layer chromatography [eluent: hexane/ethyl acetate/triethylamine (10/10/1)] to give 236 mg (52%) of the E form (6-a-E) and 51.7 mg (12%) of the Z form (6-a-Z) as oily substances.

6-a-E: NMR (CDCl$_3$; δ, ppm): 1.32(t, J=7.6 Hz, 3H), 2.56(s, 3H), 2.63(s, 3H), 2.77(q, J=7.6 Hz, 2H), 4.7–5.7(br, 2H), 5.37(s, 2H), 6.51(s, 1H), 6.69(d, J=6.6 Hz, 1H), 6.88–7.42(m, 22H)

6-a-Z: NMR (CDCl$_3$; δ, ppm): 1.24(t, J=7.4 Hz, 3H), 2.56(s, 3H), 2.64(s, 3H), 2.67(q, J=7.4 Hz, 2H), 5.20(bs, 2H), 5.30(s, 2H), 6.30(dd, J=7.9 Hz, 1.5 Hz, 1H), 6.49(d, J=1.5 Hz, 1H), 6.73(s, 1H), 6.88(s, 1H), 6.90–7.08(m, 7H), 7.23–7.43(m, 13H)

(Step B)

Compound 6-E

A mixture of 337 mg of Compound 6-a-E, 4 ml of 4N aqueous hydrochloric acid, 25 ml of dioxane and 25 ml of water was stirred at 50°–60° C. for 10 minutes. The solvent was distilled off under reduced pressure and the residue was diluted with a 1N aqueous solution of sodium hydroxide. The aqueous layer was washed with ethyl acetate and then adjusted to pH 5.2 with 4N aqueous hydrochloric acid. The resulting precipitate was separated from the mixture by filtration, washed with water and dried to give 140 mg (63%) of the product as a white solid.

Melting point: 224° C. (decomposition) NMR (DMSO-d$_6$; δ, ppm): 1.24(t, J=7.4 Hz, 3H), 2.48(s, 3H), 2.51(s, 3H), 2.75(q, J=7.4 Hz, 2H), 5.20(bs, 2H), 5.39(s, 2H), 6.50(s, 1H), 6.73(d, J=7.2 Hz, 1H), 6.95(s, 1H), 7.00(s, 1H), 7.01(d, J=7.2 Hz, 1H), 7.22–7.27(m, 1H), 7.34–7.39(m, 1H), 7.47–7.50(m, 2H) IR(KBr; cm$^{-1}$):2936, 1631, 1462, 1440, 1408, 1318, 1051, 772 Elemental analysis (%): $C_{27}H_{25}N_7O$ Found: C 69.63, H 5.22, N 20.92 Calcd.: C 69.96, H 5.44, N 21.15

(Step C)

Compound 6-Z (monohydrate)

The same procedure as in the above Step B was repeated using 46 mg of Compound 6-a-Z to give 18 mg (59%) of the product as a white solid.

Melting point: 222° C. (decomposition) NMR (DMSO-$d_6$; δ, ppm): 1.24(t, J=7.2 Hz, 3H), 2.48(s, 3H), 2.51(s, 3H), 2.75(q, J=7.2 Hz, 2H), 5.20(bs, 2H), 5.39(s, 2H), 6.49(s, 1H), 6.73(d, J=7.3 Hz, 1H), 6.94(s, 1H), 6.99(s, 1H), 7.02(d, J=1 1.9 Hz, 1H), 7.24–7.49(m, 4H) IR(KBr; cm$^{-1}$): 2944, 1460, 1438, 1404, 1321, 1050, 771 Elemental analysis (%): $C_{27}H_{25}N_7O \cdot H_2O$ Found: C 67.12, H 5.38, N 19.98 Calcd.: C 67.11, H 5.71, N 19.99

EXAMPLE 7

[9-Bromo-3-(5,7-dimethyl-2-ethyl-3H-imidazo[4,5-b]-pyridin-3-yl)methyl-6,11-dihydrodibenz[b,e]oxepin-11-yliden]acetic acid [Compound 7(0.5 hydrate)]

The same procedure as in Example 1 was repeated using 0.81 g of 9-bromo-11-oxo-6,11-dihydrodibenz[b,e]oxepin-3-carboxylic acid and 5,7-dimethyl-2-ethyl-3H-imidazo[4,5-b]pyridine, and recrystallization from isopropanol gave 0.1 g (10%) of the product as a white solid.

The product was a 23:77 mixture of geometrical isomers with respect to the stereochemistry of the double bond.

Melting point: 241°–242° C.

EXAMPLE 8

[2-(2-Butyl-4-chloro-5-hydroxymethyl-1H-imidazol-1-yl)methyl-6,11-dihydrodibenz[b,e]oxepin-11-yliden]acetic acid (Compound 8A) and

[2-(2-butyl-5-chloro-4-hydroxymethyl-1H-imidazol-1-yl)methyl-6,11-dihydrodibenz[b,e]oxepin-11-yliden]acetic acid (Compound 8B)

The same procedure as in Example 1 was repeated using 11-oxo-6,11-dihydrodibenz[b,e]oxepin-2-carboxylic acid and 2-butyl-4-chloro-5-hydroxymethyl-1H-imidazole to give Compound 8A and Compound 8B.

Compound 8A: Melting point: 170° C. (decomposition) (acetonitrile)

Compound 8B: Melting point: 106° C. (decomposition) (diisopropyl ether)

EXAMPLE 9

[2-(2-Butyl-1H-imidazol-1-yl)ethyl-6,11-dihydrodibenz[b,e]oxepin-11-yliden]acetic acid (Compound 9)

The same procedure as in Example 1 was repeated using 11-oxo-6,11-dihydrodibenz[b,e]oxepin-2-acetic acid and 2-butyl-1H-imidazole to give the product.

Melting point: 156°–157° C. (isopropanol)

EXAMPLE 10

[3-(2-Butyl-1H-imidazol-1-yl)ethyl-6,11-dihydrodibenz[b,e]oxepin-11-yliden]acetic acid (Compound The same procedure as in Example 1 was repeated using 11-oxo-6,11-dihydrodibenz[b,e]oxepin-3-acetic acid and 2-butyl-1H-imidazole to give the product.

Melting point: 237°–238° C. (isopropanol)

EXAMPLE 11

[7-(5,7-Dimethyl-2-ethyl-3H-imidazo[4,5-b]pyridin-3-yl)methyl-4,10-dihydrothieno[3,2-c][1]benzoxepin-10-yliden]acetic acid (Compound 11)

The same procedure as in Example 1 was repeated using 1.2 g of 10-oxo-4,10-dihydrothieno[3,2-c][1]benzoxepin-7-carboxylic acid and 5,7-dimethyl-2-ethyl-3H-imidazo[4,5-b]pyridine, and recrystallization from acetonitrile gave 0.1 g (5%) of the product as a white solid.

The product was a 9:1 mixture of geometrical isomers with respect to the stereochemistry of the double bond.

Melting point: 163°–166° C.

EXAMPLE 12

[7-(5,7-Dimethyl-2-ethyl-3H-imidazo[4,5-b]pyridin-3-yl)methyl-4H-benzo[4,5]cyclohepta[1,2-b]thiophen-4-yliden]acetic acid (Compound 12)

(Step A)

Compound 12

The same procedure as in Example 4 was repeated using 7-methyl-4-oxo-4H-benzo[4,5]cyclohepta[1,2-b]thiophene and 5,7-dimethyl-2-ethyl-3H-imidazo[4,5b]pyridine to give the product as an oily substance.

MS: 441 (M$^+$) NMR (CDCl$_3$; δ, ppm): 1.38(t, J=7.4 Hz, 3H), 2.58(s, 3H), 2.63(s, 3H), 2.75(q, J=7.4 Hz, 2H), 5.48(s, 2H), 5.82 and 5.97(s for each, total 1H), 6.7–7.5(m, 8H)

(Step B)

Sodium salt of Compound 12

Compound 12(0.18 g) was dissolved in 20 ml of methanol, and 0.077 ml of 28% sodium methoxide solution in methanol was added to the solution, followed by stirring at room temperature for 2 hours. The solvent was distilled off under reduced pressure and the residue was solidified with diisopropyl ether to give 0.18 g (95%) of the product.

The product was a 1:1 mixture of geometrical isomers with respect to the stereochemistry of the double bond.

Melting point: (not measurable because of hygroscopicity) Elemental analysis (%): $C_{26}H_{22}N_3O_2SNa \cdot 2H_2O$ Found: C 62.62, H 5.34, N 8.12 Calcd.: C 62.51, H 5.25, N 8.41

EXAMPLE 13

3-(4-Methyl-2-propyl-1H-benzimidazol-1-yl)methyl-11-(N-triphenylmethyltetrazol-5-yl)methylene-6,11-dihydrodibenz [b,e]oxepin (Compound 13)

The same procedures as in Example 2 and Step A of Example 6 were repeated using methyl 11-oxo-6,11-dihydrodibenz[b,e]oxepin-3-carboxylate and 4-methyl-2-propyl-1H-benzimidazole to give the product as an amorphous solid.

NMR (CDCl$_3$; δ, ppm): 1.00(t, J=7.4 Hz, 3H), 1.7–1.9(m, 2H), 2.68(s, 3H), 2.83(t, J=7.9 Hz, 2H), 4.6–5.0(br, 1H), 5.23(s, 2H), 5.3–5.7(br, 1H), 6.48(s, 1H), 6.59(d, J=8.4 Hz, 1H), 6.9–7.2(m, 12H), 7.2–7.4(m, 11H), 7.41(d, J=7.9 Hz, 1H)

EXAMPLE 14

8-(5,7-Dimethyl-2-ethyl-3H-imidazo[4,5-b]pyridin-3-yl)methyl-11-(N-triphenylmethyltetrazol-5-yl)-methylene- 6,11-dihydrodibenz[b,e]oxepin (Compound 14)

The same procedures as in Example 2 and Step A of Example 6 were repeated using methyl 11-oxo-6,11-dihydrodibenz[b,e]oxepin-8-carboxylate and 5,7-dimethyl-2-ethyl-3H-imidazo[4,5-b]pyridine to give the product, followed by separation and purification of both geometrical isomers by preparative thin layer chromatography [eluent: hexane/ethyl acetate/triethylamine (10/12.5/1)].

14-E NMR (CDCl$_3$; δ, ppm): 1.24(t, J=7.4 Hz, 3H), 2.56(s, 3H), 2.65(s, 3H), 2.66(q, J=7.4 Hz, 2H), 4.6–5.8(br, 2H), 5.39(s, 2H), 6.7–6.8(m, 2H), 6.9–7.0(m, 10H), 7.0–7.1(m, 2H), 7.1–7.4(m, 9H), 7.45(dd, J=7.9 Hz, 1.5 Hz, 1H)

14-Z NMR (CDCl$_3$; δ, ppm): 1.32(t, J=7.6 Hz, 3H), 2.58(s, 3H), 2.65(s, 3H), 2.79(q, J=7.6 Hz, 2H), 5.14(bs, 2H), 5.46(s, 2H), 6.5–6.6(m, 1H), 6.83(dd, J=8.3 Hz, 1.0 Hz, 1H), 6.91(s, 1H), 6.9–7.0(m, 9H), 7.0–7.2(m, 2H), 7.2–7.4(m, 9H), 7.38(d, J=7.9 Hz, 1H)

EXAMPLE 15

[2-(5,7-Dimethyl-2-ethyl-3H-imidazo[4,5-.b]pyridin-3-yl)methyl-10,11-dihydro-5H-dibenzo[a,d]cyclohepten-5-yliden]acetonitrile (Compound 15)

The same procedure as in Example 2 was repeated using methyl 5-oxo-10,11-dihydro-5H-dibenzo[a,d]cycloheptene-2-carboxylate and 5,7-dimethyl-2-ethyl-3H-imidazo[4,5-b]pyridine to give the product.

The product was a 1:1 mixture of geometrical isomers with respect to the stereochemistry of the double bond.

NMR (CDCl$_3$; δ, ppm): 1.29(t, J=7.6 Hz, 1.5H), 1.32(t, J=7.6 Hz, 1.5H), 2.56(s, 1.5H), 2.58(s, 1.5H), 2.63(s, 1.5H), 2.64(s, 1.5H), 2.7–2.8(m, 2H), 3.0–3.1(br, 4H), 5.41(s, 1H), 5.45(s, 1H), 5.66(s, 0.5H), 5.68(s, 0.5H), 6.8–6.9(m, 2H), 7.04(dd, J=7.9 Hz, 2.0 Hz, 0.5H), 7.12(d, J=7.4 Hz, 0.5H), 7.1–7.3(m, 4H), 7.4–7.5(m, 1H)

EXAMPLE 16

[2-(5,7-Dimethyl-2-ethyl-3H-imidazo[4,5-b]pyridin-3-yl)methyl-10,11-dihydro-5H-dibenzo[a,d]cyclohepten-5-yliden]acetic acid (Compound 16)

Compound 15 was hydrolyzed according to the same procedure as in Example 3, and recrystallization from acetonitrile gave 0.09 g (6%) of the product as a white solid.

The product was a 31:69 mixture of geometrical isomers with respect to the stereochemistry of the double bond.

Melting point: 207°–208° C.

EXAMPLE 17

3-(4-Methyl-2-propyl-1H-benzimidazol-1-yl)methyl-11-(1H-tetrazol-5-yl)methylene-6,11-dihydrodibenz[b,e]oxepin [Compound 17(monohydrate)]

The same procedure as in Step B of Example 6 was repeated using 1.8 g of Compound 13 to give 0.28 g (14%) of the product (E form) as a white solid.

Melting point: 150°–153° C. NMR (DMSO-d$_6$; δ, ppm): 0.95(t, J=7.4 Hz, 3H), 1.68–1.79(m, 2H), 2.50(s, 3H), 2.79(t, J=7.6 Hz, 2H), 5.20(bs, 2H), 5.42(s, 2H), 6.45(s, 1H), 6.67(d, J=8.4 Hz, 1H), 6.95–7.06(m, 4H), 7.17–7.26(m, 2H), 7.33–7.38(m, 1H), 7.46–7.49(m, 2H) IR(KBr; cm$^{-1}$): 2934, 1630, 1510, 1471, 1434, 1317, 1172, 1046, 758 Elemental analysis (%): C$_{28}$H$_{26}$N$_6$O.H$_2$O Found: C 70.10, H 5.77, N 17.59. Calcd.: C 69.98, H 5.87, N 17.49

EXAMPLE 18

8-(5,7-Dimethyl-2-ethyl-3H-imidazo[4,5-b]pyridin-3-yl)methyl-11-(1H-tetrazol-5-yl)methylene-6,11-dihydrodibenz[b,e]oxepin (Compound 18)

The same procedure as in Step B of Example 6 was repeated using Compound 14 to give the E form (18-E) and the Z form (18-Z).

18-E (0.8 hydrate): Melting point: 162° C. (decomposition) Elemental analysis (%): C$_{27}$H$_{25}$N$_7$O.0.8H$_2$O Found: C 67.71, H 5.69, N 20.56 Calcd.: C 67.85, H 5.61, N 20.51

18-Z: Melting point: 155° C. (decomposition)

EXAMPLE 19

1-Bromo-8-(5,7-dimethyl-2-ethyl-3H-imidazo[4,5-b]-pyridin-3-yl)methyl-5-(1H-tetrazol-5-yl)methylene-5H-dibenzo[a,d]cycloheptene [Compound 19 (0.5 diisopropyl ether adduct 0.5 hydrate)]

The same procedure as in Example 6 was repeated using 510 mg of Compound 5, and recrystallization from diisopropyl ether gave 14.2 mg (2.6%) of the product as a white solid.

The product was a single geometrical isomer with respect to the stereochemistry of the double bond.

Melting point: 159°–161° C. NMR (DMSO-d$_6$; δ, ppm): 1.29(t, J=7.4 Hz, 3H), 2.56(s, 3H), 2.61(s, 3H), 2.79(q, J=7.4 Hz, 2H), 5.43(s, 1H), 6.70–7.65(m, 9H) Elemental analysis (%): C$_{28}$H$_{24}$BrN$_7$.0.5C$_6$H$_{14}$O.0.5H$_2$O Found: C 61.80, H 4.94, N 15.99 Calcd.: C 62.21, H 5.39, N 16.38

EXAMPLE 20

2-(5,7-Dimethyl-2-ethyl-3H-imidazo[4,5-b]pyridin-3-yl)methyl-5-(1H-tetrazol-5-yl)methylene-10,11-dihydro-5H-dibenzo[[a,d]cycloheptene (Compound 20)

The same procedure as in Example 6 was repeated using 0.61 g of Compound 15 to give two compounds (hereinafter referred to as Compound 20A and Compound 20B) which were geometrical isomers with respect to the stereochemistry of the double bond.

Compound 20A (0.2 diethyl ether adduct.1.2 hydrate): Yield: 0. 016 g (2.4%) Melting point : 167°–169° C. (decomposition) NMR (DMSO-$d_6$; δ, ppm): 1.22(t, J=7.4 Hz, 3H), 2.50(s, 3H), 2.74(q, J=7.4 Hz, 3H), 3.12–3.84(m, 4H), 5.42(s, 2H), 6.72–7.29(m, 8H), 7.41(d, J=7.4 Hz, 1H) Elemental analysis (%): $C_{28}H_{27}N_7 \cdot 0.2C_4H_{10}O \cdot 1.2H_2O$ Found: C 69.35, H 5.99, N 19.58 Calcd.: C 69.46, H 6.35, N 19.69

Compound 20B (0.2 diethyl ether adduct.0.5 hydrate): Yield: 0.05 g (7.5%) Melting point: 218°–220° C. (decomposition) NMR (DMSO-$d_6$; δ, ppm): 1.24(t, J=7.4 Hz, 3H), 2.49(s, 3H), 2.51(s, 3H), 2.77(q, J=7.4 Hz, 2H), 3.12–3.84(m, 4H), 5.42(s, 2H), 6.79–7.37(m, 8H), 7.37(d, J=7.9 Hz, 1H) Elemental analysis (%): $C_{28}H_{27}N_7 \cdot 0.2C_4H_{10}O \cdot 0.5H_2O$ Found: C 71.19, H 5.99, N 20.07 Calcd.: C 71.26, H 6.23, N 20.20

EXAMPLE 21

3-(5,7-Dimethyl-2-ethyl-3H-imidazo[4,5-b]pyridin-3-yl)methyl-11-(N-triphenylmethyltetrazol-5-yl)-methylene-6,11-dihydrodibenzo[b,e]thiepin (Compound 21)

(Step A)
(3-Methoxycarbonyl-6,11-dihydrodibenzo[b,e]thiepin-11-yliden)acetonitrile (Compound 21-a)

The same procedure as in Step A of Example 2 was repeated using methyl 11-oxo-6,11-dihydrodibenzo[b,e]thiepin-3-carboxylate to give the product (97%) as a pale yellow solid.

The product was a 1:1 mixture of geometrical isomers with respect to the stereochemistry of the double bond.

NMR (CDCl$_3$; δ, ppm): 3.89(s, 1.5H), 3.90(s, 1.5H), 4.0–4.2(br, 2H), 5.62(s, 0.5H), 5.89(s, 0.5H), 7.2–7.5(m, 4.5H), 7.62(dd, J=8.0 Hz, 1.1 Hz, 0.5H), 7.7–7.9(m, 2H)

(Step B)
Methyl 11-(N-triphenylmethyltetrazol-5-yl)methylene-6,11-dihydrodibenzo[b,e]thiepin-3-carboxylate (Compound 21-b)

The same procedure as in Step A of Example 6 was repeated using Compound 21-a to give the product (47%) as an oily substance.

The product was a 1:1 mixture of geometrical isomers with respect to the stereochemistry of the double bond.

NMR (CDCl$_3$; δ, ppm): 3.40(d, J=14.0 Hz, 0.5H; E form) 3.6–3.7(br, 0.5H; Z form), 3.88(s, 3H), 4.7–4.8(br, 0.5H; Z form), 4.85(d, J=14.0 Hz, 0.5H; E form), 6.8–7.0(m, 7H), 7.0–7.1(m, 1H), 7.1–7.6(m, 14H), 7.7–7.8(m, 1H)

(Step C)
3-Hydroxymethyl-11-(N-triphenylmethyltetrazol-5-yl)methylene-6,11-dihydrodibenzo[b,e]thiepin (Compound 21-c)

Compound 21-b (3.8 g, 6.4 mmol) was dissolved in a mixture of 80 ml of ether and 40 ml of THF, and 250 mg (6.6 mmol) of lithium aluminium hydride was added to the solution under ice cooling, followed by stirring at room temperature for one hour and a half. To the mixture was added 1 ml of a saturated aqueous solution of sodium sulfate and insoluble matters were filtered off. The filtrate was diluted with ethyl acetate, and the organic layer was washed with a saturated aqueous solution of sodium chloride and dried over anhydrous magnesium sulfate. The solvent was distilled off under reduced pressure, and the residue was purified by silica gel column chromatography [eluent: hexane/ethyl acetate (5/1)] to give the E form (21-c-E; 40%) and the Z form (21-c-Z; 41%) as colorless oily substances.

21-c-E: NMR (CDCl$_3$; δ, ppm): 3.38(d, J=13.9 Hz, 1H) 4.58(bs, 2H), 4.84(d, J=13.9 Hz, 1H), 6.8–7.1(m, 7H), 7.08(dd, J=7.9 Hz, 1.6 Hz, 1H), 7.1–7.4(m, 14H), 7.46(d, J=7.9 Hz, 1H)

21-c-Z: NMR (CDCl$_3$; δ, ppm): 3.5–3.7(br, 1H), 4.47(bs, 2H), 4.7–4.9(br, 1H), 6.63(dd, J=7.9 Hz, 1.6 Hz, 1H), 6.80(s, 1H), 6.9–7.0(m, 5H), 7.02(d, J=7.9 Hz, 1H), 7.15(d, J=1.6 Hz, 1H), 7.2–7.4(m, 14H)

(Step D)
3-Bromomethyl-11-(N-triphenylmethyltetrazol-5-yl)methylene-6,11-dihydrodibenzo[b,e]thiepin (E form; Compound 21-d-E)

Compound 21-c-E (1.46 g, 2.6 mmol) was dissolved in 50 ml of dichloromethane, and 0.61 ml of 2,6-lutidine, 1.37 g of triphenylphosphine, and 1.74 g of carbon tetrabromide were added to the solution under ice cooling, followed by stirring for one hour. To the mixture was added a phosphate buffer, and the organic layer was dried over anhydrous magnesium sulfate. The solvent was distilled off under reduced pressure, and the residue was purified by silica gel column chromatography [eluent: hexane/ethyl acetate (4/1)] to give 1.51 g (93%) of the product as a white solid. The obtained product was subjected to the subsequent reaction without further purification.

(Step E)
3-Bromomethyl-11-(N-triphenylmethyltetrazol-5-yl)methylene-6,11-dihydrodibenzo[b,e]thiepin (Z form; Compound 21-d-Z)

The same procedure as in the above Step D was repeated using 1.48 g of Compound 21-c-Z to give 1.3 g (79%) of the product as a pale yellow solid. The obtained product was subjected to the subsequent reaction without further purification.

(Step F)
Compound 21-E

The same procedure as in Step D of Example 1 was repeated using 1.51 g of Compound 21-d-E to give 1.43 g (82%) of the product as an oily substance.

NMR (CDCl$_3$; δ, ppm): 1.32(t, J=7.4 Hz, 3H), 2.56(s, 3H), 2.62(s, 3H), 2.74(q, J=7.4 Hz, 2H), 3.35(d, J=13.9 Hz, 1H), 4.80(d, J=13.9 Hz, 1H), 5.33(s, 2H), 6.7–7.0(m, 11H), 7.1–7.4(m, 14H)

(Step G)
Compound 21-Z

The same procedure as in Step D of Example 1 was repeated using 1.3 g of Compound 21-d-Z to give 1.13 g (76%) of the product as an oily substance.

NMR (CDCl$_3$; δ, ppm): 1.23(t, J=7.6 Hz, 3H), 2.54(s, 3H), 2.62(q, J=7.6 Hz, 2H), 2.62(s, 3H), 3.4–3.6(br, 1H), 4.7–4.9(br, 1H), 5.24(s, 2H), 6.43(dd, J=7.9 Hz, 1.2 Hz, 1H), 6.76(s, 1H), 6.85(d, J=1.2 Hz, 1H), 6.87(s, 1H), 6.9–7.0(m, 6H), 7.1–7.4(m, 14H)

EXAMPLE 22

3-(5,7-Dimethyl-2-ethyl-3H-imidazo[4,5-b]pyridin-3-yl)methyl-11-(1H-tetrazol-5-yl)methylene-6,11-dihydrodibenzo[b,e]thiepin (Compound 22)

(Step A)
Compound 22-E (0.6 hydrate)

The same procedure as in Step B of Example 6 was repeated using 1.43 g of Compound 21-E to give 0.77 g (81%) of the product as a white solid.

Melting point: 155° C. (decomposition) NMR (CDCl$_3$; δ, ppm): 1.28(t, J=7.6 Hz, 3H), 2.56(s, 6H), 2.74(q, J=7.6 Hz, 2H), 3.40(d, J=14.0 Hz, 1H), 4.73(d, J=14.0 Hz, 1H), 5.34(s, 2H), 6.8–6.9(m, 2H), 6.89(s, 1H), 6.99(s, 1H), 7.10(d, J=7.6 Hz, 1H), 7.2–7.4(m, 4H) Elemental analysis (%): $C_{27}H_{25}N_7 \cdot 0.6H_2O$ Found: C 66.18, H 5.44, N 19.66 Calcd.: C 66.13, H 5.38, N .19.99

(Step B)
Compound 22-Z (0.6 hydrate)

The same procedure as in Step B of Example 6 was repeated using 1.13 g of Compound 21-Z to give 0.64 g (84%) of the product as a white solid.

Melting point: 160° C. (decomposition) NMR (CDCl$_3$; δ, ppm): 1.20(t, J=7.6 Hz, 3H), 2.52(s, 6H), 2.56(q, J=7.6 Hz, 2H), 3.37(bd, J=13.7 Hz, 1H), 4.61(bd, J=13.7 Hz, 1H), 5.19(d, J=16.0 Hz, 1H), 5.38(d, J=16.0 Hz, 1H), 6.77(d, J=7.9 Hz, 1H), 6.79(s, 1H), 6.86(s, 1H), 6.89(s, 1H), 7.02(d, J=7.9 Hz, 1H), 7.1–7.2(m, 1H), 7.3–7.4(m, 3H) Elemental analysis (%): $C_{27}H_{25}N_7$·0.6H$_2$O Found: C 66.27, H 5.41, N 19.85 Calcd.: C 66.13, H 5.38, N 19.99

EXAMPLE 23

[3-(5,7-Dimethyl-2-ethyl-3H-imidazo[4,5-b]pyridin-3-yl)methyl-6,11-dihydrodibenz[b,e]oxepin-11-yl]acetic acid (Compound 23)

(Step A)
Diethyl (3-hydroxymethyl-6,11-dihydrodibenz[b,e]oxepin-11-yl)malonate (Compound 23-a)

Titanium tetrachloride (0.2 ml) was added to a mixture of 420 mg of 3-acetoxymethyl-11-methoxy-6,11-dihydrodibenz[b,e]oxepin, 0.32 ml of diethyl malonate, 0.37 ml of diisopropylethylamine and 50 ml of benzene under ice cooling, and the mixture was stirred at room temperature for 6 hours. Methanol (5 ml) was added thereto, and the mixture was diluted with ethyl acetate. The organic layer was washed with a saturated aqueous solution of sodium chloride and dried over anhydrous magnesium sulfate, and the solvent was distilled off under reduced pressure.

To the resulting crude product were added 20 ml of methanol and 0.5 ml of 5% potassium hydroxide solution in methanol, followed by stirring at room temperature for one hour. The solvent was distilled off under reduced pressure and the residue was diluted with ethyl acetate. The organic layer was washed with a saturated aqueous solution of sodium chloride and dried over anhydrous magnesium sulfate. The solvent was distilled off under reduced pressure, and the residue was purified by silica gel column chromatography [eluent: chloroform/methanol (20/1)] to give 368 mg (68%) of the product as a colorless oily substance.

NMR (CDCl$_3$; δ, ppm): 0.90(t, J=7.3 Hz, 6H), 2.80(bs, 1H), 3.90(q, J=7.3 Hz, 4H), 4.52(s, 2H), 4.45–4.68(m, 2H), 4.95 and 5.53(AB, J=16.6 Hz, 2H), 6.75–7.26(m, 7H)

(Step B)
Diethyl [3-(5,7-dimethyl-2-ethyl-3H-imidazo[4,5-b]pyridin-3-yl)methyl-6,11-dihydrodibenz[b,e]oxepin-11-yl]malonate (Compound 23-b)

The same procedures as in Steps C and D of Example 1 were repeated using 367 mg of Compound 23-a and 250 mg of 5,7-dimethyl-2-ethyl-3H-imidazo[4,5-b]pyridine to give 150 mg (31%) of the product as an oily substance.

NMR (CDCl$_3$; δ, ppm): 1.00(t, J=7.5 Hz, 3H), 1.22(t, J=7.3 Hz, 3H), 1.25(t, J=7.3 Hz, 3H), 2.55(s, 3H), 2.59(s, 3H), 2.70(q, J=7.5 Hz, 2H), 3.90(q, J=7.3 Hz, 4H), 4.45–4.64(m, 2H), 5.32(s, 2H), 4.89 and 5.50(AB, J=16.7 Hz, 2H), 6.65–7.32(m, 8H)

(Step C)
[3-(5,7-Dimethyl-2-ethyl-3H-imidazo[4,5-b]pyridin-3-yl)methyl-6,11-dihydrodibenz[b,e]oxepin-11-yl]malonic acid (Compound 23-c)

The same procedure as in Step E of Example 1 was repeated using 150 mg of Compound 23-b to give 70 mg of a mixture of the desired compound and the decarboxylated compound (23) described below.

The mixture was subjected to the reaction of the next Step D without purification.

(Step D)
Compound 23

The mixture (70 mg) obtained in Step C was mixed with 0.02 ml of piperidine and 5 ml of pyridine, and the resulting mixture was heated under reflux for 2.5 hours. The solvent was distilled off under reduced pressure and the residue was diluted with water, followed by addition of 4N aqueous hydrochloric acid to adjust the pH to 5.4. The resulting precipitate was separated from the mixture by filtration and recrystallized from acetonitrile to give 41 mg (65%) of the product as a white solid.

Melting point: 199°–201° C. (decomposition) NMR (DMSO-d$_6$; δ, ppm): 1.22(t, J=7.4 Hz, 3H), 2.49(s, 3H), 2.51(s, 3H), 2.74(q, J=7.4 Hz, 2H), 2.88–3.04(m, 2H), 4.41(t, J=7.4 Hz, 1H), 4.98 and 5.43(AB, J=14.3 Hz, 2H), 5.37(s, 2H), 6.63(s, 1H), 6.69(d, J=7.9 Hz, 1H), 6.92(s, 1H), 7.12–7.25(m, 5H) Elemental analysis (%): $C_{27}H_{27}N_3O_3$ Found: C 73.37, H 6.18, N 9.70 Calcd.: C 73.45, H 6.16, N 9.52

EXAMPLE 24

3-(5,7-Dimethyl-2-ethyl-3H-imidazo[4,5-b]pyridin-3-yl)methyl-11-(N-triphenylmethyltetrazol-5-yl)-methyl-6,11-dihydrodibenz[b,e]oxepin (Compound 24)

(Step A)
Ethyl (3-methoxycarbonyl-6,11-dihydrodibenz[b,e]oxepin-11-yl)cyanoacetate (Compound 24-a)

Titanium tetrachloride (2.3 ml) was added to a mixture of 4.95 g of methyl 11-methoxy-6,11-dihydrodibenz[b,e]oxepin-3-carboxylate, 2.8 ml of ethyl cyanoacetate, 4.6 ml of diisopropylethylamine and 400 ml of benzene under ice cooling, and the mixture was stirred at room temperature for 2 days. Methanol (5 ml) was added thereto, and the mixture was diluted with ethyl acetate. The solution was washed with a saturated aqueous solution of sodium chloride and dried over anhydrous magnesium sulfate. The solvent was distilled off under reduced pressure, and the residue was purified by silica gel column chromatography [eluent: hexane/ethyl acetate (3/1)] to give 0.72 g (11%) of the product.

NMR (CDCl$_3$; δ, ppm): 1.02 and 1.06(t for each, J=7.3 Hz, total 3H), 3.90(s, 3H), 3.8–4.5(m, 4H), 5.05 and 5.56(ABsyst, J=15.7 Hz, 2H), 6.8–7.9(m, 7H)

(Step B)
Methyl 11-cyanomethyl-6,11-dihydrodibenz[b,e]oxepin-3-carboxylate (Compound 24-b)

Compound 24-a was hydrolyzed and subjected to decarboxylation according to the same procedures as in Steps C and D of Example 23 to give the product (85%) as an oily substance.

NMR (CDCl$_3$; δ, ppm): 3.18(d, J=7.9 Hz, 2H), 3.90(s, 3H), 4.16(t, J=7.9 Hz, 1H), 5.02 and 5.46(ABsyst, J=15.5 Hz, 2H), 6.9–7.4(m, 5H), 7265–7.85(m, 2H)

(Step C)
Methyl 11-(N-triphenylmethyltetrazol-5-yl)methyl-6,11-dihydrodibenz[b,e]oxepin-3-carboxylate (Compound 24-c)

The same procedure as in Step A of Example 6 was repeated using Compound 24-b to give the product (60%) as an oily substance.

NMR (CDCl$_3$; δ, ppm): 3.86(s, 3H), 4.47(t, J=7.9 Hz, 1H), 5.02 and 5.52(ABsyst, J=15.4 Hz, 2H), 6.9–7.7(m, 22H)

(Step D)
Compound 24

The same procedures as in Steps C and D of Example 21 and Step D of Example 1 were repeated using Compound 24-c to give the product (85%) as an oily substance.

NMR (CDCl$_3$; δ, ppm): 1.25(t, J=7.3 Hz, 3H), 2.57 and 2.62(s for each, total 6H), 2.65(q, J=7.3 Hz, 2H), 3.70(d, J=8.1 Hz, 2H), 4.42(t, J=8.1 Hz, 1H), 4.90 and 5.50(ABsyst, J=15.2 Hz, 2H), 5.35(s, 2H), 6.7–7.4(m, 23H)

EXAMPLE 25

3-(5,7-Dimethyl-2-ethyl-3H-imidazo[4,5-b]pyridin-3-yl)methyl-11-(1H-tetrazol-5-yl)methyl-6,11-dihydro-dibenz[b,e]oxepin (Compound 25)

(Step A)
Compound 25(0.2 ethyl acetate adduct.0.4 hydrate)

The same procedure as in Step B of Example 6 was repeated using 0.9 g of Compound 24 to give 0.45 g (77%) of the product as a solid.

Melting point: 136°–137° C. NMR (CDCl$_3$; δ, ppm): 1.16(t, J=7.4 Hz, 3H), 2.37 and 2.53(s for each, total 6H), 2.67(q, J=7.4 Hz, 2H), 3.64(d, J=7.9 Hz, 2H), 4.38(t, J=7.9 Hz, 1H), 4.69 and 5.0 1(ABsyst, J=15.3 Hz, 2H), 5.23(s, 2H), 6.57(s, 1H), 6.73–7.27(m, 7H) Elemental analysis (%): $C_{27}H_{27}N_7O.0.2C_4H_8O_2.0.4H_2O$ Found: C 6 8.18, H 6.06, N 20.10 Calcd.: C 6 8.09, H 6.04, N 19.99

(Step B)
Potassium salt of Compound 25(1.75 hydrate)

A mixture of 34.3 mg of Compound 25, 7.8 mg of potassium tert-butoxide and 10 ml of isopropanol was stirred at room temperature for one hour. The solvent was distilled off under reduced pressure and the residue was solidified with ether to give 26.1 mg (70%) of the product as a white solid.

Melting point: (not measurable because of hygroscopicity) Elemental analysis (%): $C_{27}H_{26}N_7OK.1.75H_2O$ Found: C 60.72, H 5.64, N 18.32 Calcd.: C 60.60, H 5.56, N 18.32

EXAMPLE 26

2-(5,7-Dimethyl-2-ethyl-3H-imidazo[4,5-b]pyridin-3-yl)methyl-5-(N-triphenylmethyltetrazol-5-yl)methyl-10,11-dihydro-5H-dibenzo[a,d]cycloheptene (Compound 26)

(Step A)
Ethyl (2-methoxycarbonyl-10,11-dihydro-5H-dibenzo[a,d]cyclohepten-5-yl)cyanoacetate (Compound 26-a)

Methyl 5-hydroxy-10,11-dihydro-5H-dibenzo[a,d]cycloheptene-2-carboxylate (6.11 g) was dissolved in 100 ml of dichloromethane, and 5 ml of thionyl chloride was added to the solution under ice cooling, followed by stirring at room temperature for 2 hours. The solvent was distilled off under reduced pressure, and the residue was dissolved in 50 ml of DMF (Solution A). A mixture of 3.6 ml of ethyl cyanoacetate, 1.1 g of sodium hydride (60% oily) and 200 ml of DMF was stirred for one hour, and to the resulting solution was added dropwise Solution A under ice cooling. After the mixture was stirred overnight at room temperature, the solvent was distilled off under reduced pressure and the residue was diluted with ethyl acetate. The solution was washed with a saturated aqueous solution of sodium chloride and dried over anhydrous magnesium sulfate. The solvent was distilled off under reduced pressure, and the residue was purified by silica gel column chromatography [eluent: toluene/ethyl acetate (20/1)] to give 5.58 g (67%) of the product as an oily substance.

The product was a mixture of diastereomers.

NMR (CDCl$_3$; δ, ppm): 1.04(t, J=7.2 Hz, 1.5H), 1.05(t, J=7.2 Hz, 1.5H), 3.0–3.2(br, 2H), 3.3–3.5(br, 2H), 3.90(s, 3H), 3.9–4.0(m, 2H), 4.31(d, J=11.1 Hz, 0.5H), 4.33(d, J=11.1 Hz, 0.5H), 4.61(d, J=11.1 Hz, 1H), 7.1–7.3(m, 4H), 7.4–7.5(m, 1H), 7.7–7.9(m, 2H)

(Step B)
Compound 26

The same procedures as in Steps B–D of Example 24 were repeated using Compound 26-a to give the product (39%) as an oily substance.

NMR (CDCl$_3$; δ, ppm): 1.25(t, J=7.6 Hz, 3H), 2.57(s, 3H), 2.64(s, 3H), 2.71(q, J=7.6 Hz, 2H), 2.9–3.1(br, 2H), 3.2–3.4(br, 2H), 3.67(d, J=8.3 Hz, 2H), 4.72(t, J=8.3 Hz, 1H), 5.35(s, 2H), 6.73(d, J=7.9 Hz, 1H), 6.83(s, 1H), 6.89(s, 1H), 6.9–7.1(m, 11H), 7.2–7.4(m, 9H)

EXAMPLE 27

2-(5,7-Dimethyl-2-cyclopropyl-3H-imidazo[4,5-b]-pyridin-3-yl)methyl-5-(N-triphenylmethyltetrazol-5-yl)methyl-10,11-dihydro-5H-dibenzo[a,d]cycloheptene (Compound 27)

The same procedure as in Example 26 was repeated using 5,7-dimethyl-2-cyclopropyl-3H-imidazo[4,5-b]pyridine to give the product as an oily substance.

NMR (CDCl$_3$; δ, ppm): 0.8–0.9(m, 2H), 1.0–1.1(m, 2H), 1.7–1.8(m, 1H), 2.55(s, 3H), 2.58(s, 3H), 2.9–3.1(br, 2H), 3.2–3.4(br, 2H), 3.67(d, J=8.3 Hz, 2H), 4.72(t, J=8.3 Hz, 1H), 5.45(s, 2H), 6.80(dd, J=7.9 Hz, 2.0 Hz, 1H), 6.85(s, 1H), 6.9–7.1(m, 11H), 7.07(s, 1H), 7.2–7.4(m, 9H)

EXAMPLE 28

2-(5,7-Dimethyl-2-ethyl-3H-imidazo[4,5-b]pyridin-3-yl)methyl-5-(1H-tetrazol-5-yl)methyl-10,11-dihydro-5H-dibenzo[a,d]cycloheptene (Compound 28)

(Step A)
Compound 28(0.5 hydrate)

The same procedure as in Step B of Example 6 was repeated using Compound 26 to give the product (92%) as a solid.

Melting point: 160° C. (decomposition) NMR(CDCl$_3$; δ, ppm): 1.17(t, J=7.6 Hz, 3H), 2.46(s, 3H), 2.53(s, 3H), 2.68(q, J=7.6 Hz, 2H), 2.6–2.8(br, 2H), 2.9–3.1(br, 2H), 3.53(d, J=8.3 Hz, 2H), 4.58(t, J=8.3 Hz, 1H), 5.31(s, 2H), 6.65(s, 1H), 6.68(d, J=7.9 Hz, 1H), 6.84(d, J=7.9 Hz, 1H), 6.92(s, 1H), 6.9–7.1(m, 4H) Elemental analysis (%): $C_{28}H_{29}N_7.0.5H_2O$ Found: C 71.00, H 6.49, N 20.60 Calcd.: C 71.16, H 6.40, N 20.75

(Step B)
Potassium salt of Compound 28(1.3 hydrate)

The same procedure as in Step B of Example 25 was repeated using Compound 28 to give the product (90%) as a white solid.

Melting point: (not measurable because of hygroscopicity)

Elemental analysis (%): $C_{28}H_{28}N_7K.1.3H_2O$ Found: C 64.12, H 5.98, N 18.55 Calcd.: C 64.05, H 5.87, N 18.67

EXAMPLE 29

2-(5,7-Dimethyl-2-cyclopropyl-3H-imidazo[4,5-b]-pyridin-3-yl)methyl-5-(1H-tetrazol-5-yl)methyl-10,11-dihydro-5H-dibenzo[a,d]cycloheptene [Compound 29(0.4 hydrate)]

The same procedure as in Step B of Example 6 was repeated using Compound 27 to give the product (33%) as a white solid.

Melting point: 155° C. (decomposition) NMR (CDCl$_3$; δ, ppm): 0.9–1.0(m, 2H), 1.1–1.2(m, 2H), 1.7–1.8(m, 1H), 2.44(s, 3H), 2.52(s, 3H), 2.5–2.7(br, 2H), 2.9–3.1(br, 2H), 3.4–3.6(br, 2H), 4.4–4.6(br, 1H), 5.42(d, J=16.0 Hz, 1H), 5.45(d, J=16.0 Hz, 1H), 6.72(s, 1H), 6.78(s, 1H), 6.9–7.1(m, 6H) Elemental analysis (%): $C_{29}H_{29}N_7 \cdot 0.4H_2O$ Found: C 72.07, H 6.48, N 20.18 Calcd.: C 72.14, H 6.22, N 20.31

EXAMPLE 30

5-Cyanomethyl-2-(5,7-dimethyl-2-ethyl-3H-imidazo-[4,5-b]pyridin-3-yl)methyl-10,11-dihydro-5H-dibenz[b,f]azepine (Compound 30)

(Method 1)

(Step 1A)
2-(4-Methylpiperazino)methyl-10,11-dihydro-5H-dibenz[b,f]azepine (Compound 30-1a)

10,11-Dihydro-5H-dibenz[b,f]azepine (250 g) was suspended in a mixture of 600 ml of dichloroethane and 600 ml of acetic acid, and 155 ml of 1-methylpiperazine was added dropwise to the suspension To the mixture was added 42 g of paraformaldehyde at 50° C. followed by stirring for 6 hours The solvent was distilled off under reduced pressure and the residue was diluted with ethyl acetate. The solution was washed with a saturated aqueous solution of sodium chloride and dried over anhydrous magnesium sulfate, and the solvent was distilled off under reduced pressure to give the product (91%). The obtained product was subjected to the subsequent reaction without particular purification.

(Step 1B)
5-Formyl-2-(4-methylpiperazino)methyl-10,11-dihydro-5H-dibenz[b,f]azepine (Compound 30-1b)

Formic acid (99%; 300 ml) was added dropwise to 600 ml of acetic anhydride, the internal temperature being maintained at 45° C., followed by stirring for one hour. To this solution was added, in small portions, a suspension of 375 g of Compound 30-1a in 500 ml of dichloroethane under ice cooling, followed by stirring at room temperature for 8 hours. After cooling, 400 ml of methanol was added, and the solvent was distilled off under reduced pressure. The residue was diluted with water, and adjusted to pH 9–10 with a 10N aqueous solution of sodium hydroxide. The organic layer was extracted with ethyl acetate, and the extract was washed with a saturated aqueous solution of sodium chloride and dried over anhydrous magnesium sulfate. The solvent was distilled off under reduced pressure, and the residue was purified by silica gel column chromatography [eluent: ethyl acetate/methanol/triethylamine (300/20/1)] to give 106.8 g (23%) of the product as an oily substance.

NMR (CDCl$_3$; δ, ppm): 2.27(s, 3H), 2.45(brs, 8H), 2.7–3.5(m, 4H), 3.45(s, 2H), 6.8–7.4(m, 7H), 8.55(s, 1H)
(Step 1C)
5-Formyl-2-(5,7-dimethyl-2-ethyl-3H-imidazo[4,5-b]pyridin-3-yl)methyl-10,11-dihydro-5H-dibenz[b,f]azepine (Compound 30-1c)

Compound 30-1b (50 g) was dissolved in 500 ml of dichloromethane, and 21.5 ml of ethyl chloroformate was added dropwise to the solution under ice cooling, followed by stirring at room temperature for one hour and a half. The mixture was washed with a saturated aqueous solution of sodium chloride and dried over anhydrous magnesium sulfate, and the solvent was distilled off under reduced pressure. The residue was dissolved in 100 ml of DMF, and this solution was added dropwise to a mixture of 26.1 g of 5,7-dimethyl-2-ethyl-3H-imidazo[4,5-b]pyridine, 16.7 g of potassium tert-butoxide and 80 ml of DMF, followed by stirring at room temperature for 30 minutes. The solvent was distilled off under reduced pressure and the residue was diluted with dichloromethane. The solution was washed with a saturated aqueous solution of sodium chloride and dried over anhydrous magnesium sulfate, and the solvent was distilled off under reduced pressure to give 80 g of the product. The obtained product was subjected to the subsequent reaction without particular purification.

NMR (CDCl$_3$; δ, ppm): 1.32(t, J=7.4 Hz, 3H), 2.56 and 2.61(s for each, total 6H), 2.78(q, J=7.4 Hz, 2H), 2.8–3.6(m, 4H), 5.40(s, 2H), 6.60–7.40(m, 8H), 8.50(s, 1H)
(Step 1D)
2-(5,7-Dimethyl-2-ethyl-3H-imidazo[4,5-b]pyridin-3-yl)methyl-10,11-dihydro-5H-dibenz[b,f]azepine (Compound 30-1d)

The crude Compound 30-1c (80 g) was mixed with 58 ml of 28% sodium methoxide solution in methanol and 500 ml of ethanol, and the mixture was heated under reflux for one hour. The solvent was distilled off under reduced pressure and the residue was solidified with methanol to give 40.1 g (70%) of the product as a white solid.

Melting point: 191°–192° C. (decomposition) NMR (CDCl$_3$; δ, ppm): 1.31(t, J=7.6 Hz, 3H), 2.60 and 2.63(s for each, total 6H), 2.81(q, J=7.6 Hz, 2H), 5.35(s, 2H), 6.06(s, 1H), 6.60–7.10(m, 8H)
(Step 1E)
Compound 30

Compound 30-1d (55.4 g) was dissolved in 500 ml of acetic acid and the solution was cooled to 10° C. To this solution were added 11 g of KCN and 4.6 g of paraformaldehyde, followed by stirring at room temperature for 24 hours. Then, the reaction mixture was added slowly to a mixture of 900 ml of a 10N aqueous solution of sodium hydroxide, 1.1 of ice and 1 l of dichloromethane. The organic layer was washed with a 0.1N aqueous solution of sodium hydroxide and then with a saturated aqueous solution of sodium chloride, and dried over anhydrous magnesium sulfate. The solvent was distilled off under reduced pressure, and the residue was purified by silica gel column chromatography [eluent: hexane/ethyl acetate/triethylamine (10/10/1)] to give 39 g (64%) of the product as an amorphous solid.

NMR (CDCl$_3$; δ, ppm): 1.31(t, J=7.4 Hz, 3H), 2.58 and 2.62(s for each, total 6H), 2.77(q, J=7.4 Hz, 2H), 3.06(s, 4H), 4.50(s, 2H), 5.36(s, 2H), 6.8–7.3(m, 7H)

(Method 2)

(Step 2A)
5-Cyanomethyl-10,11-dihydro-5H-dibenz[b,f]azepine (Compound 30-2a)

The same procedure as in Step 1E of Example 30 was repeated using 50 g of 5H-10,11-dihydrodibenz[b,f]azepine to give 59 g (98%) of the product.

NMR (CDCl$_3$; δ, ppm): 3.13(s, 4H), 4.53(s, 2H), 6.8–7.3(m, 8H)

(Step 2B)
5-Cyanomethyl-2-(4-methylpiperazino)-10,11-dihydro-5H-dibenz[b,f]azepine (Compound 30–2b)

The same procedure as in Step 1A of Example 30 was repeated using 5.0 g of Compound 30-2a to give 3.7 g (51%) of the product as an oily substance.

NMR (CDCl$_3$; δ, ppm): 2.27(s, 3H), 2.44(brs, 8H), 3.12(s, 4H), 3.41(s, 2H), 4.52(s, 2H)

(Step 2C)
Compound 30

The same procedure as in Step 1C of Example 30 was repeated using 3.0 g of Compound 30-2b to give 2.34 g (64%) of the product.

EXAMPLE 31

2-(5,7-Dimethyl-2-ethyl-3-imidazo[4,5-b]pyridin-3-yl)methyl-5-(N-triphenylmethyltetrazol-5-yl)-methyl-10,11-dihydro- 5H-dibenz[b,f]azepine (Compound 31)

(Method 1)

A mixture of 8.65 g of Compound 30, 20 ml of tri-n-butyltin chloride, 4.8 g of sodium azide and 250 ml of toluene was heated under reflux at 100°–110° C. for 4 days. After ice cooling, 150 ml of water and 20 ml of a 10N aqueous solution of sodium hydroxide was added to the mixture. The aqueous layer was washed with ethyl acetate, and adjusted to pH 5 with 4N aqueous hydrochloric acid. The resulting precipitate was separated from the mixture by filtration and dried to give 7.4 g (78%) of crude Compound 32 (described below). This crude compound was subjected to N-triphenylmethylation according to the same procedure as in Step A of Example 6 to give 9.07 g (81%) of the desired compound as an amorphous solid.

NMR (CDCl$_3$; δ, ppm): 1.25(t, J=7.4 Hz, 3H), 2.56 and 2.62(s for each, total 6H), 2.71(q, J=7.4 Hz, 2H), 3.00(s, 4H), 5.19(s, 2H), 5.32(s, 2H), 6.6–7.5(m, 22H)

(Method 2)

(Step 2A)
2-Hydroxymethyl-10,11-dihydro-5H-dibenz[b,f]azepine (Compound 31–2a)

5-Benzyl-2-formyl-10,11-dihydro-5H-dibenz[b,f]azepine (3.29 g) was dissolved in 200 ml of ethanol, and 0.5 g of sodium borohydride was added to the solution, followed by stirring at room temperature for 30 minutes. The solvent was distilled off under reduced pressure, and the residue was diluted with dichloromethane. The mixture was washed with 1N aqueous hydrochloric acid and a saturated aqueous solution of sodium chloride, and dried over anhydrous magnesium sulfate. After the solvent was distilled off under reduced pressure, the residue was dissolved in 300 ml of ethanol. To the solution was added 300 mg of 10% palladium carbon and the mixture was stirred in a stream of hydrogen for 4 days. The catalyst was filtered off, and the filtrate was concentrated under reduced pressure. The residue was purified by silica gel column chromatography [eluent: hexane/ethyl acetate (2/1)] to give 1.0 g (42%) of the product.

NMR (CDCl$_3$; δ, ppm): 2.26(bs, 1H), 2.98(s, 4H), 4.45(s, 2H), 6.04(bs, 1H), 6.53–7.01(m, 7H)

(Step 2B)
2-(tert-Butyldimethylsilyloxymethyl)-10,11-dihydro-5H-dibenz[b,f]azepine (Compound 31-2b)

A mixture of 1.0 g of Compound 31-2a, 1.5 g of imidazole, 1.5 g of tert-butyldimethylsilyl chloride and 30 ml of DMF was stirred overnight at room temperature, followed by addition of ice chips and further stirring. After the solvent was distilled off under reduced pressure, the residue was diluted with ethyl acetate, washed with a saturated aqueous solution of sodium bicarbonate and a saturated aqueous solution of sodium chloride, and then dried over anhydrous magnesium sulfate. The solvent was distilled off under reduced pressure, and the residue was purified by silica gel column chromatography [eluent: hexane/ethyl acetate (10/1)] to give 1.34 g (89%) of the product as a colorless oily substance.

NMR (CDCl$_3$; δ, ppm): 0.10(s, 6H), 0.92(s, 9H), 3.06(s, 4H), 4.63(s, 2H), 6.65–7.06(m, 7H)

(Step 2C)
2-(tert-Butyldimethylsilyloxymethyl)-5-(N-triphenylmethyltetrazol-5-yl)methyl-10,11-dihydro-5H-dibenz[b,f]azepine (Compound 31-2c)

A mixture of 1.3 g of Compound 31-2b, 2.0 g of 5-chloromethyl-N-triphenylmethyltetrazole, 0.6 g of sodium iodide, 0.2 g of sodium hydride (60% oily) and 50 ml of DMF was stirred at 80° C. for 15 hours. The solvent was distilled off under reduced pressure, and the residue was diluted with ethyl acetate. The organic layer was washed with a saturated aqueous solution of sodium bicarbonate and a saturated aqueous solution of sodium chloride, and then dried over anhydrous magnesium sulfate. The solvent was distilled off under reduced pressure, and the residue was purified by silica gel column chromatography [eluent: hexane/ethyl acetate (10/1)] to give 1.05 g of an oily substance containing the desired compound.

The product contained impurities, but was subjected to the subsequent reaction without further purification.

NMR (CDCl$_3$; δ, ppm): 0.07(s, 6H), 0.85(s, 9H), 2.99(s, 4H), 4.62(s, 2H), 5.23(s, 2H), 6.7–7.7(m, 22H)

(Step 2D)
2-Hydroxymethyl-5-(N-triphenylmethyltetrazol-5-yl)methyl-10,11-dihydro-5H-dibenz[b,f]azepine (Compound 31-2d)

The substance obtained in Step 2C. was dissolved in 50 ml of THF, and 6 ml of 1M tetrabutylammonium fluoride/THF solution was added to the solution, followed by stirring at room temperature for 2 hours. The solvent was distilled off under reduced pressure and the residue was diluted with ether. The organic layer was washed with a saturated aqueous solution of sodium chloride and dried over anhydrous magnesium sulfate. The solvent was distilled off under reduced pressure, and the residue was purified by silica gel column chromatography [eluent: chloroform/methanol (50/1)] to give 0.23 g (26%) of the product as a yellow oily substance.

NMR (CDCl$_3$; δ, ppm): 2.05(s, 1H), 2.98(s, 4H), 4.43(s, 2H), 5.13(s, 2H), 6.75–7.19(m, 22H) IR(CHCl$_3$; cm$^{-1}$): 3400, 2924, 1702, 1598, 1491

(Step 2E)
Compound 31

The same procedures as in Steps C and D of Example 1 were repeated using 0.21 g of Compound 31-2d and 180 mg of 5,7-dimethyl-2-ethyl-3H-imidazo[4,5-b]pyridine to give 0.1 g (38%) of the product.

EXAMPLE 32

2-(5,7-Dimethyl-2-ethyl-3H-imidazo[4,5-b]pyridin-3-yl)methyl-5-(1H-tetrazol-5-yl)methyl-10,11-dihydro-5H-dibenz[b,f]azepine (Compound 32)

A mixture of 43.6 g of Compound 31, 50 ml of 4N aqueous hydrochloric acid, 200 ml of water and 300 ml of dioxane was stirred at room temperature for one hour. The solvent was distilled off under reduced pressure, and the residue was diluted with water and a 10N aqueous solution of sodium hydroxide to be adjusted to pH 12. After washing with ethyl acetate, the aqueous layer was adjusted to pH 5 with 4N aqueous hydrochloric acid. The resulting precipitate was separated from the mixture by filtration and recrystallized from acetone to give 18.2 g (64%) of the product as a white solid.

Melting point: 177°–179° C. NMR (DMSO-$d_6$; δ, ppm): 1.18(t, J=7.4 Hz, 3H), 2.49(s, 6H), 2.69(q, J=7.4 Hz, 2H), 3.09(s, 4H), 5.23(s, 2H), 5.31(s, 2H), 6.78–7.20(m, 8H) Elemental analysis (%): $C_{27}H_{28}N_8$ Found: C 70.17, H 6.25, N.23.80

Calcd.: C 69.80, H 6.08, N 24.12

EXAMPLE 33

5-Carboxymethyl-2-(5,7-dimethyl-2-ethyl-3H-imidazo[4,5-b]pyridin-3-yl)methyl-10,11-dihydro-5H-dibenz[b,f]azepine [Compound 33(0.3 hydrate)]

Compound 30(1.0 g) was hydrolyzed according to the same procedure as in Example 3 to give 0.98 g (94%) of the product as a white solid.

Melting point: 114°–115° C. NMR (DMSO-$d_6$; δ, ppm): 1.23(t, J=7.4 Hz, 3H), 2.50(s, 6H), 2.76(q, J=7.4 Hz, 2H), 3.05(brs, 4H), 4.40(s, 2H), 5.32(s, 2H), 6.63–7.08(m, 8H) Elemental analysis (%): $C_{27}H_{28}N_4 \cdot 0.3H_2O$ Found: C 72.98, H 6.65, N 12.51 Calcd.: C 72.72, H 6.46, N 12.56

EXAMPLE 34

2-(5,7-Dimethyl-2-cyclopropyl-3H-imidazo[4,5-b]-pyridin-3-yl)methyl-5-(1H-tetrazol-5-yl)methyl-10,11-dihydro-5H-dibenz[b,f]azepine (Compound 34)

(Step A)
Compound 34
The same procedures as in Examples 30–32 were repeated using 5,7-dimethyl-2-cyclopropyl-3H-imidazo[4,5-b]pyridine to give the crude product as a solid.

Melting point:. 172° C. (diisopropyl ether) NMR (DMSO-$d_6$; δ, ppm): 1.00(t, J=7.4 Hz, 3H), 1.03(brs, 4H), 2.11(m, 1H), 2.43 and 2.48(s for each, total 6H), 3.04(brs, 4H), 4.88(s, 2H), 5.39(s, 2H), 6.75–7.30(m, 8H)
(Step B)
Potassium salt of Compound 34
The same procedure as in Step B of Example 25 was repeated using Compound 34 to give the product.

Melting point: 167°–169° C. (ether) Elemental analysis (%): $C_{28}H_{27}N_8K$ Found: C 65.12, H 5.51, N 21.62 Calcd.: C 65.34, H 5.29, N 21.77

EXAMPLE 35

2-(5,7-Dimethyl-2-ethyl -3H-imidazo[4,5-b]pyridin-3-yl)methyl-8-methyl-5-(1H-tetrazol-5-yl)-methyl-10,11-dihydro-5H-dibenz[b,f]azepine (Compound 35)

(Step A)
8-Methyl-10,11-dihydro-5H-dibenz[b,f]azepine (Compound 35-a)

Compound 35-a was obtained as a by-product in Step 2A of Example 31.

Melting point: 72°–74° C. NMR (CDCl$_3$; δ, ppm): 2.15(s, 3H), 3.00(s, 4H), 5.80(brs, 1H), 6.50–7.20(m, 7H)
(Step B)
Compound 35(monohydrate)
The same procedures as in Examples 30–32 were repeated using Compound 35-a to give the product as a white solid.

Melting point: 136°–137° C. (ether) NMR (DMSO-$d_6$; δ, ppm): 1.19(t, J=7.4 Hz, 3H), 2.15(s, 3H), 2.49(s, 6H), 2.72(q, J=7.4 Hz, 2H), 3.06(s, 4H), 5.18(s, 2H), 5.30(s, 2H), 6.75–7.20(m, 7H) Elemental analysis (%): $C_{28}H_{30}N_8 \cdot H_2O$ Found: C 69.63, H 6.58, N 23.18 Calcd.: C 69.48, H 6.37, N 23.15

EXAMPLE 36

2-(5,6-Dimethyl-1H-benzimidazol-1-yl)methyl-5-(1H-tetrazol-5-yl)methyl-10,11-dihydro-5H-dibenz-[b,f]azepine (Compound 36)

The same procedures as in Examples 30–32 were repeated using 5,6-dimethyl-1H-benzimidazole to give the product as a white solid.

Melting point: 188°–189° C. (acetonitrile) Elemental analysis (%): $C_{26}H_{25}N_7$ Found: C 71.93, H 5.97, N 22.23 Calcd.: C 71.70, H 5.79, N 22.51

EXAMPLE 37

2-(5,7-Dimethyl-2-ethyl-3H-imidazo[4,5-b]pyridin-3-yl)methyl-5-[2-(1H-tetrazol-5-yl)phenyl]methyl-10,11-dihydro- 5H-dibenz[b,f]azepine (Compound 37)

(Step A)
5-(2-Cyanophenyl)methyl-10,11-dihydro-5H-dibenz[b,f]azepine (Compound 37-a)

Iminodibenzyl (10 g) was dissolved in THF, and 32 ml of n-butyl lithium (1.6M hexane solution) was added to the solution under ice cooling, followed by stirring under the same conditions for 30 minutes. To the mixture was added 180 ml of a solution of (2-cyanophenyl)benzylbromide in THF, and the mixture was stirred overnight at room temperature. Then, the mixture was diluted with ethyl acetate, washed with a saturated aqueous solution of sodium chloride, and dried over anhydrous magnesium sulfate. The solvent was distilled off under reduced pressure, and the residue was purified by silica gel column chromatography [eluent: hexane/ethyl acetate (9/1)] to give 9.92 g (63%) of the product.

NMR (CDCl$_3$; δ, ppm): 3.24(s, 4H), 5.17(s, 2H), 6.7–7.7(m, 2H)
(Step B)
2-Formyl-5-(2-cyanophenyl)methyl-10,11-dihydro-5H-dibenz[b,f]azepine (Compound 37-b)

DMF (5 ml) was added dropwise to 5 ml of phosphorus oxychloride with cooling. To the solution was added dropwise 40 ml of a solution of 7.0 g of Compound 37-a in DMF, followed by stirring at 70° C. for 6 hours. The reaction mixture was poured onto ice, and extracted with ethyl acetate. The organic layer was washed with a saturated aqueous solution of sodium chloride and dried over anhydrous magnesium sulfate. The solvent was distilled off under reduced pressure, and the residue was purified by silica gel column chromatography [eluent: hexane/ethyl acetate (2/1)]

to give 5.83 g (75%) of the product as a yellow amorphous solid.

NMR (CDCl$_3$; δ, ppm): 3.26(s, 4H), 5.24(s, 2H), 6.9–7.7(m, 7H), 9.80(s, 1H)

(Step C)
2-Hydroxymethyl-5-(2-cyanophenyl)methyl-10,11-dihydro-5H-dibenz[b,f]azepine (Compound 37-c)

The same procedure as in Step 2A of Example 31 was repeated using Compound 37-b to give the product (98%) as a yellow amorphous solid.

NMR (CDCl$_3$; δ, ppm): 3.24(s, 4H), 4.54(brs, 2H), 5.16(s, 2H), 6.7–7.7(m, 11H)

(Step D)
2-(5,7-Dimethyl-2-ethyl-3H-imidazo[4,5-b]pyridin-3-yl)methyl-5-(2-cyanophenyl)methyl-10,11-dihydro-5H-dibenz[b,f]azepine (Compound 37-d)

The same procedures as in Steps C and D of Example 1 were repeated using Compound 37-c to give the product (27%) as an oily substance.

NMR (CDCl$_3$; δ, ppm): 1.25(t, J=7.4 Hz, 3H), 2.57 and 2.61(s for each, total 6H), 2.70(q, J=7.4 Hz, 2H), 3.15(s, 4H), 5.12(s, 2H), 5.30(s, 2H), 6.85–7.61(m, 12H)

(Step E)
Compound 37(0.2 diisopropyl ether adduct.0.3 hydrate)

The same procedures as in Method 1 of Example 31 and Step B of Example 6 were repeated using Compound 37-d, followed by solidification with diisopropyl ether to give the product (48%) as a white solid.

Melting point: 133°–135° C. NMR (CDCl$_3$; δ, ppm): 1.11(t, J=7.4 Hz, 3H), 2.54 and 2.56(s for each, total 6H), 2.73(q, J=7.4 Hz, 2H), 2.9–3.1(m, 4H), 5.29(s, 2H), 5.32(s, 2H), 6.5–7.6(m, 11H) Elemental analysis (%): C$_{26}$H$_{25}$N$_7$.0.2C$_6$H$_{14}$O.0.3H$_2$O Found: C 72.40, H 6.14, N 19.73 Calcd.: C 72.51, H 6.29, N 19.78

EXAMPLE 38

2-[[2-(5,7-Dimethyl-2-ethyl-3H-imidazo[4,5-b]pyridin-3-yl)methyl-10,11-dihydro-5H-dibenz[b,f]azepin-5-yl]methyl]benzoic acid [Compound 38 (0.4 diisopropyl ether adduct.1.5 hydrate)]

Compound 37-d was hydrolyzed according to the same procedure as in Example 3, followed by solidification with diisopropyl ether to give the product (50%).

Melting point: 137° C. (decomposition) NMR (DMSO-d$_6$; δ, ppm): 1.18(t, J=7.4 Hz, 3H), 2.49(s, 6H), 2.71(q, J=7.4 Hz, 2H), 3.05(s, 4H), 5.20(s, 2H), 5.29(s, 2H), 6.75(d, J=7.9 Hz, 1H), 6.85(d, J=7.4 Hz, 1H), 6.90(s, 1H), 6.97–7.14(m, 5H), 7.22(t, J=7.4 Hz, 1H), 7.35(t, J=7.4 Hz, 1H), 7.54(d, J=7.4 Hz, 1H) IR(KBr tablet; cm$^{-1}$): 1598, 1477, 1221 Elemental analysis (%): C$_{33}$H$_{32}$N$_4$O$_2$.0.4C$_6$H$_{14}$O.1.5H$_2$O Found: C 72.85, H 6.70, N 9.35 Calcd.: C 72.74, H 7.00, N 9.58

EXAMPLE 39

2-(4-Carboxy-2-ethyl-3H-benzimidazol-3-yl)methyl-5-(1H-tetrazol-5-yl)methyl-10,11-dihydro-5H-dibenz[b,f]azepine (Compound 39)

(Step A)
N-[(5-Formyl-10,11-dihydro-5H-dibenz[b,f]azepin-2-yl)methyl]-N-[3-(methoxycarbonyl)nitrobenzen-2-yl]propionamide (Compound 39-a)

The same procedure as in Step 1C of Example 30 was repeated using N-[3-(methoxycarbonyl)nitrobenzen-2-yl]propionamide to give the product (22%) as a yellow amorphous solid.

NMR (CDCl$_3$; δ, ppm): 1.13(t, J=7.4 Hz, 3H), 2.11(q, J=7.4 Hz, 2H), 2.6–3.4(m, 4H), 3.44 and 3.48(s for each, total 3H), 4.34 and 4.98(ABsyst, J=12.2 Hz, 2H), 6.8–8.2(m, 10H), 8.50 and 8.52(s for each, total 1H)

(Step B)
2-(2-Ethyl-4-methoxycarbonyl-3H-benzimidazol-3-yl)methyl-5-formyl-10,11-dihydro-5H-dibenz[b,f]azepine (Compound 39-b)

A mixture of 1.5 g of Compound 39-a, 2.9 g of tin, 3 ml of conc. aqueous hydrochloric acid and methanol was heated under reflux for one hour and a half. The mixture was diluted with ethyl acetate, washed with a saturated aqueous solution of sodium chloride, and dried over anhydrous magnesium sulfate. The solvent was distilled off under reduced pressure, and the residue was purified by silica gel column chromatography [eluent: hexane/ethyl acetate/triethylamine (10/10/1)] to give 0.12 g (8%) of the product as a yellow oily substance.

NMR (CDCl$_3$; δ, ppm): 1.25(t, J=7.1 Hz, 3H), 2.6–3.7(m, 6H), 3.69(s, 3H), 4.12(q, J=7.1 Hz, 2H), 5.74(s, 2H), 6.6–8.3(m, 10H), 8.50(s, 1H)

(Step C)
Compound 39

The same procedures as in Steps 1D and 1E of Example 30, Method 1 of Example 31, and Step B of Example 6 were repeated using Compound 39-b to give the product as a solid.

Melting point: 145°–146° C. NMR (DMSO-d$_6$; δ, ppm): 1.26(t, J=7.1 Hz, 3H), 2.6–3.2(m, 6H), 5.18(s, 2H), 5.57(s, 2H), 6.7–7.90(m, 10H) Elemental analysis (%): C$_{27}$H$_{25}$N$_7$O$_2$ Found: C 67.77, H 5.33, N 20.12 Calcd.: C 67.63, H 5.25, N 20.45

EXAMPLE 40

N-[[5-(1H-Tetrazol-5-yl)methyl-10,11-dihydro-5H-dibenz[b,f]azepin-2-yl]methyl]-N-valerylvaline (Compound 40)

(Step A) 5-Cyanomethyl-2-formyl-10,11-dihydro-5H-dibenz[b,f]azepine (Compound 40-a)

The same procedure as in Step B of Example 37 was repeated using 1.0 g of Compound 30-2a to give 0.27 g (24%) of the product as an oily substance.

NMR (CDCl$_3$; δ, ppm): 3.07(s, 4H), 4.4(s, 2H), 6.8–7.7(m, 7H), 9.77(s, 1H)

(Step B)
N-[(5-Cyanomethyl-10,11-dihydro-5H-dibenz[b,f]azepin-2-yl)methyl]valine (Compound 40-b)

A mixture of 1.0 g of Compound 40-a, 0.7 g of valine methylester hydrochloride, 0.5 g of molecular sieves and 15 ml of THF was stirred at room temperature for 2 days. After ice cooling, 3 ml of methanol and subsequently 0.4 g of sodium cyanoborohydride were added to the mixture. After the mixture was stirred overnight, insoluble matters were filtered off, and the filtrate was concentrated. The residue was diluted with dichloromethane, washed with a saturated aqueous solution of sodium chloride, and dried over anhydrous magnesium sulfate. The Solvent was distilled off under reduced pressure, and the residue was purified by silica gel column chromatography [eluent: hexane/ethyl acetate (1/1)] to give 1.2 g (82%) of the product as a yellow oily substance.

NMR (CDCl$_3$; $\delta$, ppm): 0.92 and 0.94(d for each, J=6.8 Hz, total 6H), 1.7–2.1(m, 1H), 3.0(d, J=8.4 Hz, 1H), 3.12(s, 4H), 3.50 and 3.75(ABsyst, J=12.8 Hz, 2H), 3.70(s, 3H), 4.53(s, 2H), 6.8–7.3(m, 7H)

(Step C)

N-[(5-Cyanomethyl-10,11-dihydro-5H-dibenz[b,f]azepin-2yl)methyl]-N-valerylvaline (Compound 40-c)

Compound 40-b (1.2 g) was dissolved in a mixture of 30 ml of dichloromethane and 0.6 ml of diisopropylethylamine, and 0.4 ml of valeryl chloride was added to the solution under ice cooling, followed by stirring at room temperature for 5 hours. Then, ice was added thereto, and the mixture was stirred for some time. The mixture was diluted with dichloromethane, washed with a saturated aqueous solution of sodium bicarbonate and a saturated aqueous solution of sodium chloride, and dried over anhydrous magnesium sulfate. The solvent was distilled off under reduced pressure, and the residue was purified by silica gel column chromatography [eluent: hexane/ethyl acetate (5/1)] to give 1.4 g (96%) of the product as a yellow oily substance.

NMR (CDCl$_3$; $\delta$, ppm): 0.8–2.6(m, 17H), 3.11(s, 4H), 3.45(s, 3H), 4.54(brs, 2H), 5.29(s, 2H), 6.8–7.3(m, 7H)

(Step D)

Compound 40(0.5 diisopropyl ether adduct.0.5 hydrate)

The same procedures as in Method 1 of Example 31 and Step E of Example 1 were repeated using 1.4 g of Compound 40-c, followed by solidification with diisopropyl ether to give 0.38 g (25%) of the product as a pale yellow solid.

Melting point: 82° C. NMR (CDCl$_3$; $\delta$, ppm): 0.85–1.70(m, 15H), 2.41(t, J=7.4 Hz, 2H), 2.9–3.2(m, 4H), 4.24 and 4.71(ABsyst, J=16.8 Hz, 2H), 5.08 and 5.15(ABsyst, J=15.1 Hz, 2H), 6.85–7.15(m, 7H) Elemental analysis (%): $C_{27}H_{34}N_6O_3 \cdot 0.5C_6H_{14} \cdot 0.5H_2O$ Found: C 65.77, H 7.80, N 15.09 Calcd.: C 65.43, H 7.69, N 15.26

EXAMPLE 41

N-[(5-Cyanomethyl-10,11-dihydro-5H-dibenz[b,f]-azepin-2-yl)methyl]-N-(3-ethoxycarbonylpyridin-2-yl)propylamine (Compound 41)

The same procedure as in Method 1c of Example 30 was repeated using Compound 30-2b and N-(3-ethoxycarbonylpyridin-2-yl)propylamine to give the product.

NMR (CDCl$_3$; $\delta$, ppm): 0.99(t, J=7.0 Hz, 3H), 1.2–1.8(m, 5H), 3.01(t, J=7.9 Hz, 2H), 3.14(s, 4H), 3.47(q, J=7.0 Hz, 2H), 4.54(s, 2H), 5.20(s, 2H), 6.46(dd, J=7.9 Hz, 5.1 Hz, 1H), 6.8–7.3(m, 7H), 8.0–8.3(m, 2H)

EXAMPLE 42

3-(5,7-Dimethyl-2-ethyl-3H-imidazo[4,5-b]pyridin-3-yl)methyl-9-[2-(1H-tetrazol-5-yl)ethyl]carbazole (Compound 42)

(Step A)

9-(2-Cyanoethyl) carbazole (Compound 42-a)

Carbazole (8.0 g) was suspended in 100 ml of toluene, and 4 ml of acrylonitrile and subsequently 0.5 ml of Triton B were added to the suspension, whereby the suspension was solidified. Then, the reaction mixture was allowed to stand for one hour, and methanol was added thereto, followed by filtration to give 4.41 g (42%) of the product as a white solid.

NMR (CDCl$_3$; $\delta$, ppm): 2.84(t, J=7.3 Hz, 2H), 4.65(t, J=7.3 Hz, 2H), 7.1–7.6(m, 6H), 8.10(dd, J=7.5 Hz, 1.1 Hz, 2H)

(Step B)

9-(2-Cyanoethyl)-3-formylcarbazole (Compound 42-b)

The same procedure as in Step B of Example 37 was repeated using 6.3 g of Compound 42-a to give 5.08 g (72%) of the product as an oily substance.

NMR (CDCl$_3$; $\delta$, ppm): 2.90(t, J=6.7 Hz, 2H), 4.75(t, J=6.7 Hz, 2H), 7.3–8.2(m, 7H), 8.62(s, 1H)

(Step C)

9-(2-Cyanoethyl)-3-hydroxymethylcarbazole (Compound 42-c)

The same procedure as in Step 2A of Example 31 was repeated using 2.8 g of Compound 42-b to give 1.8 g (65%) of the product as an oily substance.

NMR (CDCl$_3$; $\delta$, ppm): 2.79(t, J=7.1 Hz, 2H), 4.60(t, J=7.1 Hz, 2H), 4.84(s, 2H), 7.1–7.6(m, 4H), 7.9–8.2(m, 2H)

(Step D)

9-(2-Cyanoethyl)-3-(5,7-dimethyl-2-ethyl-3H-imidazo[4,5-b]pyridin-3-yl)methylcarbazole (Compound 42-d)

The same procedures as in Steps C and D of Example 1 were repeated using 1.8 g of Compound 42-c to give 0.53 g (18%) of the product as an oily substance.

NMR (CDCl$_3$; $\delta$, ppm): 1.30(t, J=7.4 Hz, 3H), 2.62 and 2.64(s for each, total 6H), 2.6–3.0(m, 4H), 4.60(t, J=7.0 Hz, 2H), 5.63(s, 2H), 6.91(s, 1H), 7.1–7.4(m, 4H), 7.8–8.1(m, 2H)

(Step E)

Compound 42(0.75 hydrate)

The same procedures as in Method 1 of Example 31 and Step B of Example 6 were repeated using 0.53 g of Compound 42-d, followed by solidification with diisopropyl ether to give 0.16 g (48%) of the product.

Melting point: 180°–181° C. NMR (CDCl$_3$; $\delta$, ppm): 1.11(t, J=7.4 Hz, 3H), 2.50 and 2.61(s for each, total 6H), 2.67(q, J=7.4 Hz, 2H), 3.30(t, J=6.9 Hz, 2H), 4.60(t, J=6.9 Hz, 2H), 5.52(s, 2H), 6.88(s, 1H), 6.85–7.30(m, 5H), 7.63–7.66(m, 2H) Elemental analysis (%): $C_{26}H_{26}N_8 \cdot 0.75H_2O$ Found: C 67.25, H 5.91, N 24.17 Calcd.: C 67.29, H 5.97, N 24.15

EXAMPLE 43

N-[[9-[2-(1H-Tetrazol-5-yl)ethyl]carbazol-3-yl]methyl]-N-valerylvaline [Compound 43 (0.1 diisopropyl ether adduct.0.6 hydrate)]

The same procedures as in Steps B–D of Example 40 were repeated using Compound 42-b to give the product.

Melting point: 111°–112° C. (diisopropyl ether) NMR (CDCl$_3$; $\delta$, ppm): 0.75–1.8(m, 15H), 2.30–2.70(m, 3H), 3.44(t, J=7.2 Hz, 2H), 4.70(t, J=7.2 Hz, 2H), 4.85 and 4.95(ABsyst, J=15.6 Hz, 2H), 7.1–7.5(m, 5H), 7.93(s, 1H), 8.02(dd, J=11.6 Hz, 7.7 Hz, 1H) Elemental analysis (%): $C_{26}H_{32}N_6O_3 \cdot 0.1C_6H_{14} \cdot 0.6H_2O$ Found: C 64.03, H 6.94, N 16.79 Calcd.: C 64.21, H 7.01, N 16.89

EXAMPLE 44

3-(5,7-Dimethyl-2-ethyl-3H-imidazo[4,5-b]pyridin-3-yl)methyl-10-[2-(1H-tetrazol-5-yl)ethyl]phenothiazine [Compound 44(0.25 hydrate)]

The same procedure as in Example 42 was repeated using phenothiazine to give the product.

Melting point: 121°–122° C. (diisopropyl ether) NMR (CDCl$_3$; δ, ppm): 1.31(t, J=7.4 Hz, 3H), 2.59 and 2.61(s for each, total 6H), 2.84(q, J=7.4 Hz, 2H), 3.41(t, J=6.9 Hz, 2H), 4.27(brs, 2H), 5.38(s, 2H), 6.8–7.3(m, 8H) Elemental analysis (%): C$_{26}$H$_{26}$N$_8$S·0.25H$_2$O Found: C 64.30, H 5.46, N 22.09 Calcd.: C 64.11, H 5.48, N 23.00

EXAMPLE 45

Tablets

Tablets each having the following composition are prepared in a conventional manner.

| | |
|---|---|
| Compound 6-E | 50 mg |
| Lactose | 60 mg |
| Potato starch | 50 mg |
| Polyvinyl alcohol | 2 mg |
| Magnesium stearate | 1 mg |
| Tar pigment | trace |

EXAMPLE 46

Powder

Powder having the following composition is prepared in a conventional manner.

| | |
|---|---|
| Compound 32 | 50 mg |
| Lactose | 250 mg |

What is claimed is:

1. A tricyclic compound represented by the following formula (I):

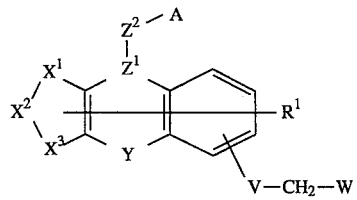

wherein R$^1$ represents hydrogen, halogen or lower alkyl; A represents cyano, carboxyl, tetrazolyl, cyano-substituted phenyl, carboxyl-substituted phenyl or terazolyl-substituted phenyl; V represents —(CH$_2$)$_m$— (wherein m is an integer of 0 to 2): W represents

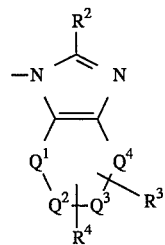

(wherein R$^2$, R$^3$ and R$^4$ independently represent hydrogen, halogen, lower alkyl, cycloalkyl, halogenated lower alkyl, hydroxy, lower alkoxy, amino, lower alkylamino, carboxyl or lower alkoxycarbonyl; and Q$^1$—Q$^2$—Q$^3$—Q$^4$ represents N=CH—CH=CH; X$^1$—X$^2$—X$^3$ represents CH=CH—CH=CH, S—CH=CH or CH=CH—S; Y represents a single bond, CH$_2$, O, S, CH$_2$O, OCH$_2$, CH$_2$S, SCH$_2$, CH$_2$CH$_2$ or CH=CH; and Z$^1$—Z$^2$ represents C=CH, CH—CH$_2$ or CH—CH(COOH)— or a pharmaceutically acceptable salt thereof.

2. The tricyclic compound as claimed in claim 1, wherein R$^1$ is H; X$^1$—X$^2$—X$^3$ is CH=CH—CH=CH; m in V is 0; and V is oriented at the para-position from the Z$^1$ atom in the tricyclic system.

3. The tricyclic compound as claimed in claim 2, wherein A is tetrazolyl.

4. The tricyclic compound as claimed in claim 3, wherein Y is CH$_2$CH$_2$.

5. The tricyclic compound as claimed in claim 4, wherein Z$^1$—Z$^2$ is CH—CH$_2$.

6. The tricyclic compound as claimed in claim 5, wherein W is 5,7-dimethyl-2-ethyl-3H-imidazo[4,5-b]pyridin-3-yl.

7. The tricyclic compound as claimed in claim 4, wherein Z$^1$—Z$^2$ is C=CH.

8. The tricyclic compound as claimed in claim 7, wherein W is 5,7-dimethyl-2-ethyl-3H-imidazo[4,5-b]pyridin-3-yl.

9. The tricyclic compound as claimed in claim 3, wherein Y is CH$_2$O.

10. The tricyclic compound as claimed in claim 9, wherein Z$^1$—Z$^2$ is CH—CH$_2$.

11. The tricyclic compound as claimed in claim 10, wherein W is 5,7-dimethyl-2-ethyl-3H-imidazo[4,5-b]pyridin-3-yl.

12. A pharmaceutical composition comprising a pharmaceutical carrier and as an active ingredient, an effective amount of the compound as defined by claim 1.

* * * * *

UNITED STATES PATENT AND TRADEMARK OFFICE
CERTIFICATE OF CORRECTION

PATENT NO. : 5,478,840

DATED : December 26, 1995

INVENTOR(S): ETSUO OHSHIMA ET AL.

Page 1 of 4

It is certified that error appears in the above-identified patent and that said Letters Patent is hereby corrected as shown below:

Title page,

AT [56] REFERENCES CITED

Other Publications, "Chiar." should read --Chim.--.

COLUMN 2

Line 4, "$R^3$" should read --$R^2$--.

COLUMN 14

Line 10, "0.01" should read --0.1--.

COLUMN 16

Line 54, "carboxy -substituted" should read --carboxy-substituted--.

COLUMN 22

Line 19, "(Xvd)" should read --(XVd)--.

COLUMN 52

Line 56, "N⎯⎯" should read -- 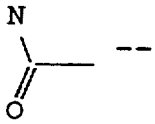 --.

UNITED STATES PATENT AND TRADEMARK OFFICE
CERTIFICATE OF CORRECTION

PATENT NO. : 5,478,840

DATED : December 26, 1995

INVENTOR(S): ETSUO OHSHIMA ET AL.

It is certified that error appears in the above-identified patent and that said Letters Patent is hereby corrected as shown below:

COLUMN 60

Line 17, "Compound 2,582" should read --Compound 2, 582--.

COLUMN 62

Line 4, "(Compound" should read --(Compound 10)--.

COLUMN 64

Line 41, "adduct 0.5" should read --adduct·0.5--.

COLUMN 68

Line 58, "7265-7.85" should read --7.65-7.85--.

COLUMN 71

Line 11, "$_5$," should read --$\delta$,--.
    Line 35, "hours" should read --hours.--.

COLUMN 73

Line 24, "Compound 30,20" should read --Compound 30, 20--.

UNITED STATES PATENT AND TRADEMARK OFFICE
CERTIFICATE OF CORRECTION

PATENT NO. : 5,478,840

DATED : December 26, 1995

INVENTOR(S) : ETSUO OHSHIMA ET AL.

It is certified that error appears in the above-identified patent and that said Letters Patent is hereby corrected as shown below:

COLUMN 74

Line 12, "1)]to" should read --1)] to--.
LIne 58, "$_5$," should read --$\delta$,--.

COLUMN 78

Line 63, "Solvent" should read --solvent--.

COLUMN 79

Line 1, "$_5$," should read --$\delta$,--.

COLUMN 80

Line 22, "$_5$," should read --$\delta$,--.

UNITED STATES PATENT AND TRADEMARK OFFICE
CERTIFICATE OF CORRECTION

PATENT NO. : 5,478,840

DATED : December 26, 1995

INVENTOR(S) : ETSUO OHSHIMA ET AL.

It is certified that error appears in the above-identified patent and that said Letters Patent is hereby corrected as shown below:

COLUMN 81

Line 48, "terazolyl-substituted" should read --tetrazolyl-substituted--.

Signed and Sealed this

Twenty-fourth Day of September, 1996

Attest:

BRUCE LEHMAN

Attesting Officer      Commissioner of Patents and Trademarks